(12) United States Patent
Yu et al.

(10) Patent No.: US 11,161,933 B2
(45) Date of Patent: Nov. 2, 2021

(54) CONJUGATED POLYMER AND USE THEREOF IN ORGANIC ELECTRONIC DEVICE

(71) Applicant: GUANGZHOU CHINARAY OPTOELECTRONIC MATERIALS LTD., Guangdong (CN)

(72) Inventors: Mingquan Yu, Guangdong (CN); Xi Yang, Guangdong (CN); Junyou Pan, Guangdong (CN)

(73) Assignee: Guangzhou Chinaray Optoelectronic Materials Ltd., Guangzhou (CN)

( * ) Notice: Subject to any disclaimer, the term of this patent is extended or adjusted under 35 U.S.C. 154(b) by 0 days.

(21) Appl. No.: 16/469,473

(22) PCT Filed: Dec. 13, 2017

(86) PCT No.: PCT/CN2017/115982
§ 371 (c)(1),
(2) Date: Jun. 13, 2019

(87) PCT Pub. No.: WO2018/108108
PCT Pub. Date: Jun. 21, 2018

(65) Prior Publication Data
US 2020/0109236 A1    Apr. 9, 2020

(30) Foreign Application Priority Data

Dec. 13, 2016 (CN) .......... 201611147725.9

(51) Int. Cl.
*C08G 61/12* (2006.01)
*C07D 209/86* (2006.01)
(Continued)

(52) U.S. Cl.
CPC ......... *C08G 61/124* (2013.01); *C07D 209/86* (2013.01); *C07D 209/88* (2013.01);
(Continued)

(58) Field of Classification Search
CPC .................................................. C08G 61/124
See application file for complete search history.

(56) References Cited

U.S. PATENT DOCUMENTS 3,567,450 A    3/1971   Brantly et al.
3,615,404 A    10/1971  Price et al.
(Continued)

FOREIGN PATENT DOCUMENTS

CN    1583691 A      2/2005
CN    102282150 A    12/2011
(Continued)

OTHER PUBLICATIONS

PCT/CN2017/115982, "International Search Report", dated Mar. 14, 2018, 2 pages.
(Continued)

*Primary Examiner* — William D Young
(74) *Attorney, Agent, or Firm* — Cozen O'Connor

(57) ABSTRACT

A conjugated polymer comprises repeating units as represented by formula (I), $$\pm A\text{-}B\pm_p \qquad (I)$$

p is the number of the repeating units, and p is an integer more than or equal to 1; and A has a structure as represented by formula (II), and B has a structure as represented by formula (II) or formula (III).

(Continued)

-continued

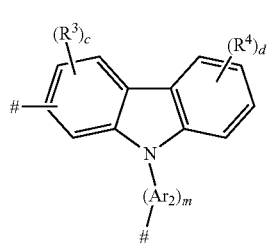

(III)

The described conjugated polymer has a higher triplet energy level and a higher charge transfer property.

8 Claims, 1 Drawing Sheet

(51) Int. Cl.
    *C07D 209/88*     (2006.01)
    *C07F 5/04*     (2006.01)
    *H01L 51/00*     (2006.01)
    *H01L 51/05*     (2006.01)
    *H01L 51/42*     (2006.01)
    *H01L 51/50*     (2006.01)

(52) U.S. Cl.
    CPC ............ *C07F 5/04* (2013.01); *H01L 51/0035* (2013.01); *C08G 2261/11* (2013.01); *C08G 2261/1412* (2013.01); *C08G 2261/18* (2013.01); *C08G 2261/228* (2013.01); *C08G 2261/312* (2013.01); *C08G 2261/3241* (2013.01); *C08G 2261/512* (2013.01); *C08G 2261/514* (2013.01); *C08G 2261/516* (2013.01); *C08G 2261/522* (2013.01); *C08G 2261/524* (2013.01); *C08G 2261/91* (2013.01); *C08G 2261/92* (2013.01); *C08G 2261/94* (2013.01); *C08G 2261/95* (2013.01); *H01L 51/0003* (2013.01); *H01L 51/0004* (2013.01); *H01L 51/0558* (2013.01); *H01L 51/42* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

| | | | |
|---|---|---|---|
| 4,720,432 A | 1/1988 | VanSlyke et al. | |
| 4,769,292 A | 9/1988 | Tang et al. | |
| 5,061,569 A | 10/1991 | VanSlyke et al. | |
| 5,121,029 A | 6/1992 | Hosokawa et al. | |
| 5,130,603 A | 7/1992 | Tokailin et al. | |
| 6,020,078 A | 2/2000 | Chen et al. | |
| 6,251,531 B1 | 6/2001 | Enokida et al. | |
| 6,824,895 B1 | 11/2004 | Sowinski et al. | |
| 6,830,828 B2 | 12/2004 | Thompson et al. | |
| 6,835,469 B2 | 12/2004 | Kwong et al. | |
| 7,029,766 B2 | 4/2006 | Huo et al. | |
| 7,250,226 B2 | 7/2007 | Tokito et al. | |
| 7,250,532 B2 | 7/2007 | Iwakuma et al. | |
| 2001/0053462 A1 | 12/2001 | Mishima | |
| 2005/0258742 A1 | 11/2005 | Tsai et al. | |
| 2006/0210830 A1 | 9/2006 | Funahashi et al. | |
| 2006/0222886 A1 | 10/2006 | Kwong et al. | |
| 2007/0087219 A1 | 4/2007 | Ren et al. | |
| 2007/0092753 A1 | 4/2007 | Begley et al. | |
| 2007/0252517 A1 | 11/2007 | Owczarczyk et al. | |
| 2008/0027220 A1 | 1/2008 | Stossel et al. | |
| 2008/0113101 A1 | 5/2008 | Inoue et al. | |
| 2009/0061681 A1 | 3/2009 | McMunigal et al. | |
| 2009/0134784 A1 | 5/2009 | Lin et al. | |
| 2012/0004407 A1 | 1/2012 | Stoessel et al. | |
| 2012/0217869 A1 | 8/2012 | Adachi et al. | |
| 2016/0111663 A1* | 4/2016 | Kim ................... H01L 51/0058 257/40 |
| 2019/0097137 A1* | 3/2019 | Radu ..................... C08L 101/04 |
| 2019/0165293 A1* | 5/2019 | Ishitsuka ................ H01L 51/50 |

FOREIGN PATENT DOCUMENTS

| | | |
|---|---|---|
| CN | 102668152 A | 9/2012 |
| CN | 103221406 A | 7/2013 |
| CN | 103483332 A | 1/2014 |
| CN | 103889952 A | 6/2014 |
| CN | 105529406 A | 4/2016 |
| CN | 105586030 A | 5/2016 |
| DE | 102005058557 A1 | 6/2007 |
| EP | 1191613 B1 | 3/2006 |
| EP | 1957606 A1 | 8/2008 |
| EP | 1191614 B1 | 5/2009 |
| EP | 1191612 B1 | 9/2009 |
| JP | 2913116 B2 | 6/1999 |
| JP | 200853397 A | 3/2008 |
| TW | 201309696 A | 3/2013 |
| TW | 201309778 A | 3/2013 |
| TW | 201343874 A | 11/2013 |
| TW | 201350558 A | 12/2013 |
| WO | 0070655 A2 | 11/2000 |
| WO | 2001021729 A1 | 3/2001 |
| WO | 200141512 A1 | 6/2001 |
| WO | 200202714 A2 | 1/2002 |
| WO | 200215645 A1 | 2/2002 |
| WO | 2004/084260 A2 | 9/2004 |
| WO | 2005019373 A2 | 3/2005 |
| WO | 2005033244 A1 | 4/2005 |
| WO | 2006/000388 A1 | 1/2006 |
| WO | 2006/000389 A1 | 1/2006 |
| WO | 2006/058737 A1 | 6/2006 |
| WO | 2006/122630 A1 | 11/2006 |
| WO | 2007/065549 A1 | 6/2007 |
| WO | 2007095118 A2 | 8/2007 |
| WO | 2007/115610 A1 | 10/2007 |
| WO | 2007/140847 A1 | 12/2007 |
| WO | 2008/006449 A1 | 1/2008 |
| WO | 2009118087 A1 | 10/2009 |
| WO | 2009146770 A2 | 12/2009 |
| WO | 2010015307 A1 | 2/2010 |
| WO | 2010031485 A1 | 3/2010 |
| WO | 2010034125 A1 | 4/2010 |
| WO | 2010054728 A1 | 5/2010 |
| WO | 2010054731 A1 | 5/2010 |
| WO | 2010086089 A1 | 8/2010 |
| WO | 2010099852 A1 | 9/2010 |
| WO | 2010102709 A1 | 9/2010 |
| WO | 2010135519 A1 | 11/2010 |
| WO | 2011110277 A1 | 9/2011 |
| WO | 2011157339 A1 | 12/2011 |
| WO | 2012007086 A1 | 1/2012 |
| WO | 2012007087 A1 | 1/2012 |
| WO | 2013133359 A1 | 9/2013 |
| WO | 2013154064 A1 | 10/2013 |
| WO | 2016/036207 A | 3/2016 |
| WO | 2017092476 A | 6/2017 |

OTHER PUBLICATIONS

Baldo, et al., "High-efficiency fluorescent organic light-emitting devices using a phosphorescent sensitizer", Nature vol. 403, (2000), pp. 750-753.

Adachi et al., "High-efficiency red electrophosphorescence devices", Appl. Phys. Lett. vol. 78 (2001), pp. 1622-1624.

(56) References Cited

OTHER PUBLICATIONS

Kido et al., "Bright red lightemitting organic electroluminescent devices having a europium complex as an emitter", Appl. Phys. Lett. vol. 65 (1994), p. 2124-2126.

Kido et al., "Electroluminescence in a Terbium Complex", Chem. Lett. (1990) pp. 657-660.

Johnson et al., "Luminescent Iridium(I), Rhodium(I), and Platinum(II) Dithiolate Complexes", JACS (1983) vol. 105, pp. 1795-1802.

Wrighton et al., "The Nature of the Lowest Excited State in Tricarbonylchloro-1, 10-phenanthrolinerhenium(I) and Related Complexes", JACS vol. 96 (1974) pp. 998-1003.

Ma, et al., "Electroluminescence from triplet metal-ligand charge-transfer excited state of transition metal complexes", Synth. Metals vol. 94 (1998) pp. 245-248.

Endo et al., "Thermally Activated Delayed Fluorescence from Sn4p-Porphyrin Complexes and Their Application to Organic Light-Emitting Diodes—A Novel Mechanism for Electroluminescence", Adv. Mater., vol. 21 (2009) pp. 4802-4806.

Endo et al., "Efficient up-conversion of triplet excitons into a singlet state and its application for organic light emitting diodes", Appl. Phys. Lett., vol. 98 (2011) pp. 083302-01-083302-03.

Lee et al., "High-efficiency organic light-emitting diodes utilizing thermally activated delayed fluorescence from triazine-based donor-acceptor hybrid molecules", vol. 101 Appl. Phys. Lett., vol. 101 (2012) 093306-01-093306-04.

Tanaka, "Efficient green thermally activated delayed fluorescence (TADF) from a phenoxazine-triphenyltriazine (PXZ-TRZ) derivative", Chem. Commun. vol. 48 (2012) 11392-11394.

Goushi et.al., "Organic light-emitting diodes employing efficient reverse intersystem crossing for triplet-to-singlet state conversion", Nature Photonics, vol. 6 (2012) pp. 253-258.

Uoyama et al., "Highly efficient organic light-emitting diodes from delayed fluorescence", Nature, vol. 492 (2012) pp. 234-238.

Zhang et.al., "Design of Efficient Thermally Activated Delayed Fluorescence Materials for Pure Blue Organic Light Emitting Diodes", J. Am. Chern. Soc, vol. 134 (2012) pp. 14706-14709.

Mehes et.al., "Enhanced Electroluminescence Efficiency in a Spiro-Acridine Derivative through Thermally Activated Delayed Fluorescence", Angew. Chem. Int. Ed, vol. 51 (2012) pp. 11311-11315.

Nakagawa et.al., "Electroluminescence based on thermally activated delayed fluorescence generated by a spirobifluorene donor-acceptor structure", Chem. Commun., vol. 48 (2012) 9580-9582.

Nasu et.al., "A highly luminescent spiro-anthracenone-based organic light-emitting diode exhibiting thermally activated delayed fluorescence", Chem. Commun., vol. 49 (2013), 10385-10387.

Li et.al., "Highly Efficient Organic Light-Emitting Diode Based on a Hidden Thermally Activated Delayed Fluorescence Channel in a Heptazine Derivative", Adv. Mater., vol. 25 (2013) pp. 1-5.

Dias et.al., "Triplet Harvesting with 100% Efficiency by Way of Thermally Activated Delayed Fluorescence in Charge Transfer OLED Emitters", Adv. Mater., vol. 25 (2013) pp. 3707-3714.

Komino et.al., "Suppression of Efficiency Roll-Off Characteristics in Thermally Activated Delayed Fluorescence Based Organic Light-Emitting Diodes Using Randomly Oriented Host Molecules", Chem. Mater., vol. 25 (2013) pp. 3038-2047.

Tanaka et.al., "Twisted Intramolecular Charge Transfer State for Long-Wavelength Thermally Activated Delayed Fluorescence", Chem. Mater., vol. 25, (2013) pp. 3766-3771.

Lee et.al., "Oxadiazole- and triazole-based highly-efficient thermally activated delayed fluorescence emitters for organic light-emitting diodes", J. Mater. Chem. C., vol. 1 (2013) pp. 4599-4605.

Ishimatsu et.al., "Solvent Effect on Thermally Activated Delayed Fluorescence by 1,2,3,5-Tetrakis(carbazol-9-yl)-4,6-dicyanobenzene", J. Phys. Chem. A., vol. 117 (2013) pp. 5607-5612.

Kipphan (Handbook of Print Media: Technologies and Production Methods), ISBN 3-540-67326-1,Chapter 1.3, pp. 40-67, Chapter 1.5, pp. 117-144, Chapter 5.5, pp. 711-730.

Bulovic et. al., "Transparent light-emitting devices", Nature, vol. 380 (1996) p. 29.

Gu et. al., "Transparent organic light emitting device", Appl. Phys. Lett. vol. 68 (1996) pp. 2606-2608.

\* cited by examiner

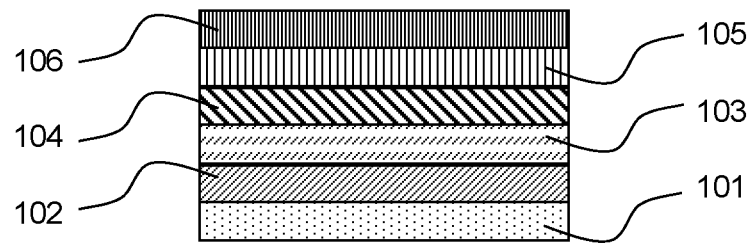

CONJUGATED POLYMER AND USE THEREOF IN ORGANIC ELECTRONIC DEVICE

CROSS-REFERENCE TO RELATED APPLICATIONS

The present application is the national phase of International Application PCT/CN2017/115982, filed on Dec. 13, 2017, which claims priority to Chinese Application No. 201611147725.9, filed on Dec. 13, 2016, both of which are incorporated herein by reference in their entireties.

TECHNICAL FIELD

The present disclosure relates to the field of optoelectronic technology, and particularly to a conjugated polymer and use thereof in an organic electronic device.

BACKGROUND

In conventional organic electroluminescent devices, application of small molecular materials, such as phosphorescent emitters, is a very mature technology. Organic electroluminescent devices (SMOLEDs) constructed from small molecular materials have a high luminous efficiency, long lifetime, and relatively low operating voltage. However, one of the major drawbacks of preparing devices from small molecular materials is that the preparation process is very complicated. For example, the complicated vacuum thermal evaporation process required to deposit a layer of small molecular material, which greatly limits the maximum size of a device that can be prepared.

With the development of technology, many conjugated polymers with functions corresponding to small molecular materials have been applied in optoelectronic technology, and can be used to prepare devices by spin coating or inkjet printing which is very cheap, simple and convenient, thereby conjugated polymers have become materials with great application potential in organic light-emitting devices (OLEDs).

An OLED constructed from a polymer as a main material is often referred to a PLED (PLED=polymer light-emitting device). There are two ways to construct a PLED: 1. only one layer of polymer which includes the functions (charge injection, charge transporting, charge recombination, photon emission) of an OLED as many as possible; 2. a variety of polymers forming different functional layers with each having only one single function, or only a few multifunctional layers. In order to form a polymer having a specific function, different polymers need to be polymerized with monomers having corresponding functions. For example, in order to produce light of three colors, it is usually necessary to introduce specific monomers into the polymer to achieve emission of three colors of red, green and blue. In order to obtain a high luminous efficiency, it is preferred to use a triplet emitter (phosphorescence) rather than a singlet emitter (fluorescence). However, most conjugated polymers reported so far have a lower triplet energy level and may quench the emission of any exciton with higher triplet energy (relatively shorter wavelength), and thereby, most conjugated polymers are only suitable for use as a host material in a triplet emitter of red light or yellow light, and not suitable for use as a host material in a triplet emitter of light color having a higher triplet energy (a blue or green triplet emitter).

A non-conjugated or partially conjugated polymer can avoid the above-mentioned triplet exciton quenching problem due to its relatively high triplet energy level. However, it must be pointed out that a lifetime of PLEDs formed from such high molecules is very short. For example, poly-N-vinylcarbazole (PVK) (see U.S. Pat. No. 7,250,226B2) is a typical host of a green phosphorescent device. Optoelectronic devices constructed from PVK-based polymers have a very short lifetime, and due to the non-conjugated backbone of the polymer, charge transporting in the devices suffers from additional resistance, resulting in a very high operating voltage.

WO2004/084260A2 describes a structure having a longer lifetime than a single layer PLED, and in such structure, an intermediate layer is introduced between the hole injection layer and the light-emitting layer. Such intermediate layer usually has hole transporting, electron blocking and exciton blocking functions, and electron blocking and exciton blocking functions are particularly important which functions can limit excitons in the light-emitting layer, thereby improving the luminous efficiency. Such a device with an intermediate layer is also used in a solution processed small molecular OLED device in which the light-emitting layer is composed of soluble small molecules. However, the high molecule of the intermediate layer needs to satisfy very demanding conditions, such as the need for a suitable HOMO, and additionally, a high triplet energy level and LUMO are also necessary. The intermediate layer high molecule known to date does not have the properties as described above, especially its triplet energy level is not high enough, and the LUMO is very low.

Therefore, it is very necessary to develop a conjugated polymer having a suitable HOMO energy level, a high triplet state, and excellent electron blocking ability.

SUMMARY

A conjugated polymer includes a repeating unit represented by general formula (I):

$$\text{--}(\text{A-B})_p\text{--} \qquad (I)$$

wherein p is the number of the repeating units and is an integer greater than or equal to 1;

A has a structure represented by general formula (II), and B has a structure represented by general formula (II) or general formula (III);

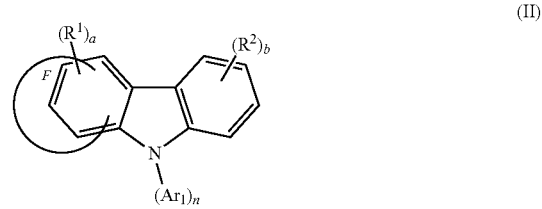

(II)

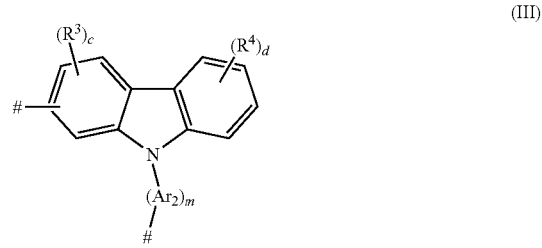

(III)

wherein ring F is an aromatic ring system containing 5 to 20 ring atoms or a heteroaromatic ring system containing 5 to 20 ring atoms;

$Ar_1$, $Ar_2$ are each independently an aromatic ring system containing 5 to 40 ring atoms or a heteroaromatic ring system containing 5 to 40 ring atoms;

$R^1$, $R^2$, $R^3$ and $R^4$ are each independently selected from the group consisting of H, D, F, CN, an alkyl chain, a fluoroalkyl chain, an aromatic ring, a heteroaromatic ring, an amino group, a silicon group, a methyl germanium group, an alkoxy group, an aryloxy group, a fluoroalkoxy group, a siloxane, a siloxy group, a crosslinkable group; the hydrogen atoms of said alkyl chain, fluoroalkyl chain, aromatic ring, heteroaromatic ring, amino group, silicon group, methyl germanium group, alkoxy group, aryloxy group, fluoroalkoxy, siloxane, siloxy group are optionally substituted with one or more deuterium atoms;

the adjacent $R^1$, $R^2$, $R^3$, $R^4$ may form a monocyclic or polycyclic aliphatic or aromatic ring system with each other or with a ring bonded to said groups;

a is 0, 1, 2, 3, 4, 5, 6, 7, 8, 9, or 10;

b, c and d are each independently 0, 1, 2, 3 or 4;

m and n are each independently 0 or 1;

The linking way of the general formula (II) is as shown in general formula (II-1) or general formula (II-2):

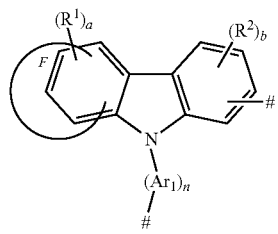

(II-1)

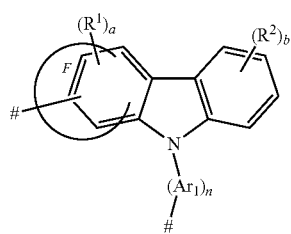

(II-2)

# is the linking point of the unit to other functional groups in the conjugated polymer.

A polymeric monomer has any one structure selected from formulas (X-1) to (X-8):

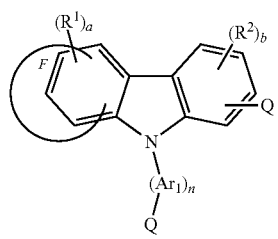

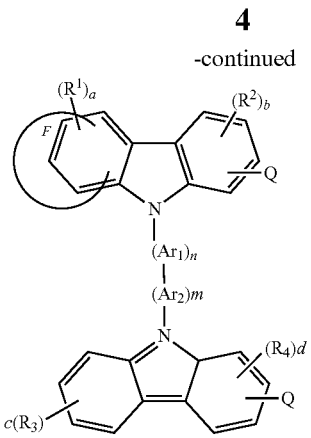

-continued

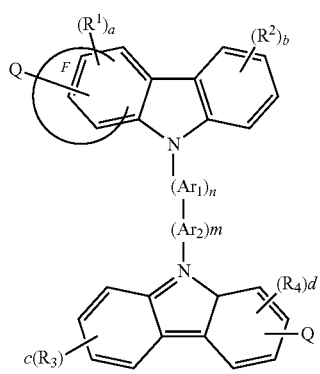

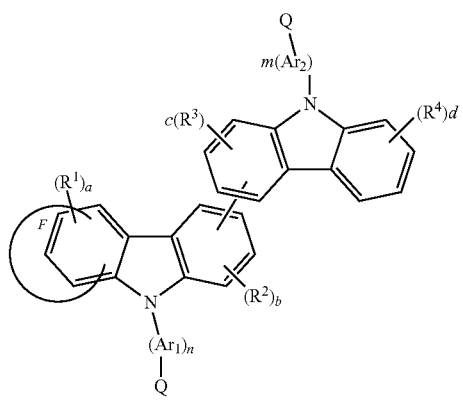

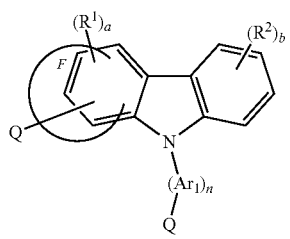

-continued wherein Q is a leaving group;

$R^1$, $R^2$, $R^3$, $R^4$, a, b, c, d, m, n, $Ar^1$, $Ar^2$, F are defined similarly as above.

A mixture includes the foregoing conjugated polymer, and an organic functional material selected from the group consisting of a hole injection or transporting material, a hole blocking material, an electron injection or transporting material, an electron blocking material, an organic matrix material, a singlet emitter, a triplet emitter, a thermally activated delayed fluorescent material and an organic dye.

A formulation includes the foregoing conjugated polymer, and an organic solvent.

An organic electronic device includes a functional layer comprising the foregoing conjugated polymer, the foregoing mixture or prepared from the foregoing formulation.

A method for preparing the foregoing organic electronic device includes the step of coating the foregoing conjugated polymer, the foregoing mixture or the foregoing formulation onto a substrate by a printing or coating method to form a functional layer.

The foregoing conjugated polymer has a higher triplet excited state energy level and high charge transporting performance.

The foregoing formulation has a better printability and film-forming property, and is convenient to implement a high-performance organic electronic device, particularly an organic electroluminescent device, by solution processing, particularly by printing processing, thereby providing a technical solution with low cost and high efficiency.

BRIEF DESCRIPTION OF THE DRAWING

FIG. 1 is a cross-sectional view of an exemplary organic electronic device in accordance with one embodiment of the disclosure.

DETAILED DESCRIPTION OF EMBODIMENTS

The present disclosure provides a high molecular polymer or copolymer, a synthesis method, and use thereof in an organic electronic device, the present disclosure will be further described in detail below in order to make the objects, technical solutions and effects of the present disclosure clearer and more definite. It should be understood that the specific embodiments described herein are merely illustrative of, and are not intended to limit, the disclosure.

In the present disclosure, the host material and the matrix material, Host and Matrix have the same meaning and are interchangeable.

In the present disclosure, the metal organic clathrate, the metal organic complex, the organometallic complex and the metal complex have the same meaning and are interchangeable.

In the present disclosure, the formulation, the printing ink, the ink and the inks have the same meaning and are interchangeable.

In the present disclosure, when there are a plurality of substituents represented by the same symbols at different positions in one repeating unit, the substituents may be the same or different.

In the present disclosure, the conjugated polymer includes a copolymer.

The present disclosure provides a polymer having a repeating unit represented by general formula (I):

$$\text{---}(\text{A-B})\text{---}_p \qquad (\text{I})$$

wherein p is the number of the repeating units and an integer greater than or equal to 1;

A has a structure represented by general formula (II), B has a structure represented by general formula (II) or general formula (III);

(II)

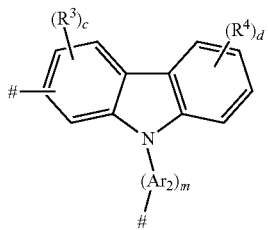

(III)

wherein ring F is an aromatic ring system containing 5 to 20 ring atoms or a heteroaromatic ring system containing 5 to 20 ring atoms;

$Ar_1$, $Ar_2$ are each independently an aromatic ring system containing 5 to 40 ring atoms or a heteroaromatic ring system containing 5 to 40 ring atoms;

$R^1$, $R^2$, $R^3$ and $R^4$ are each independently selected from the group consisting of D, F, CN, an alkyl chain, a fluoroalkyl chain, an aromatic ring, a heteroaromatic ring, an amino group, a silicon group, a methyl germanium group, an alkoxy group, an aryloxy group, a fluoroalkoxy group, a siloxane, a siloxy group, a crosslinkable group; a deuterated alkyl chain, a deuterated partially-fluorinated alkyl chain, a deuterated aromatic ring, a deuterated heteroaromatic ring, a deuterated amino group, a deuterated silicon group, a deuterated methyl germanium group, a deuterated alkoxy group, a deuterated aryloxy group, a deuterated fluoroalkoxy group, a deuterated siloxane, a deuterated siloxy group.

That is to say, the hydrogen atoms of said alkyl chain, fluoroalkyl chain, aromatic ring, heteroaromatic ring, amino group, silicon group, methyl germanium group, alkoxy group, aryloxy group, fluoroalkoxy, siloxane, siloxy group are optionally substituted with one or more deuterium atoms.

The adjacent $R^1$, $R^2$, $R^3$, $R^4$ may form a monocyclic or polycyclic aliphatic or aromatic ring system with each other or with a ring bonded to said groups;

a is 0, 1, 2, 3, 4, 5, 6, 7, 8, 9, or 10;
b, c, and d are each independently 0, 1, 2, 3 or 4;
m and n are each independently 0 or 1;
the linking way of A in the conjugated polymer is general formula (II-1) or general formula (II-2):

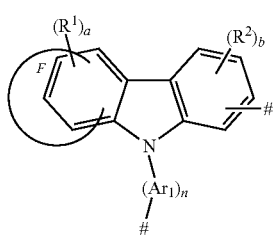

(II-1)

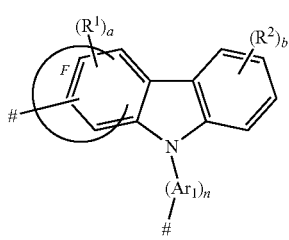

(II-2)

# is the linking point of the unit to other functional groups in the conjugated polymer.

In an embodiment, a is 0, 1, 2, 3, 4 or 5; in one embodiment, a is 0, 1, 2 or 3. In an embodiment, a is 0 or 1.

In an embodiment, b, c, and d are each independently 0, 1, 2 or 3; in an embodiment, b, c, and d are each independently 0 or 1.

In an embodiment, at least one of n and m is 1.

In certain embodiments, p is an integer greater than 1, and in another embodiment, p is an integer greater than 10 and less than 1,000,000. In another embodiment, p is an integer greater than 1000 and less than 500,000.

In the present embodiment, ring F is an aromatic ring system containing 5 to 20 ring atoms or a heteroaromatic ring system containing 5 to 20 ring atoms; in an embodiment, ring F is an aromatic ring system containing 5 to 15 ring atoms or a heteroaromatic ring system containing 5 to 15 ring atoms; in one embodiment, ring F is an aromatic ring system containing 5 to 10 ring atoms or a heteroaromatic ring system containing 5 to 10 ring atoms; in one embodiment, ring F is an aromatic ring system containing 6 to 10 ring atoms or a heteroaromatic ring system containing 6 to 10 ring atoms.

In an embodiment, the aromatic ring system contains 5 to 15 carbon atoms, further the aromatic ring system contains 5 to 10 carbon atoms, and the heteroaromatic ring system contains 2 to 15 carbon atoms, further the heteroaromatic ring system contains 2 to 10 carbon atoms, and at least one heteroatom in the ring system, provided that the total number of the carbon atoms and the heteroatoms is at least 4. In one embodiment, the heteroatoms are selected from Si, N, P, O, S and/or Ge, particularly selected from Si, N, P, O and/or S, more particularly selected from N, O or S.

The foregoing aromatic ring system or aryl group refers to a hydrocarbonyl group containing at least one aromatic ring, including a monocyclic group and a polycyclic ring system. The foregoing heteroaromatic ring system or heteroaryl group refers to a hydrocarbonyl group containing at least one heteroaromatic ring (containing a heteroatom), including a monocyclic group and a polycyclic ring system. These polycyclic rings may have two or more rings where two carbon atoms are shared by two adjacent rings, i.e., a fused ring. At least one of ring in polycyclic rings is aromatic or heteroaromatic. For the purpose of the present disclosure, the aromatic or heteroaromatic ring system not only includes a system of an aryl or heteroaryl group, but also has a plurality of aryl or heteroaryl groups spaced by short non-aromatic units (<10% of non-H atoms and preferably <5% of non-H atoms, such as C, N or O atoms). Thus, systems such as 9,9'-spirobifluorene, 9,9-diarylfluorene, triarylamine and diaryl ether are considered to be aromatic ring systems for the purpose of this disclosure.

Specifically, examples of the aromatic group are benzene, naphthalene, anthracene, phenanthrene, perylene, tetracene, pyrene, benzopyrene, triphenylene, acenaphthene, fluorene, spirofluorene and derivatives thereof.

Specifically, examples of the heteroaryl group are furan, benzofuran, dibenzofuran, thiophene, benzothiophene, dibenzothiophene, pyrrole, pyrazole, triazole, imidazole, oxazole, oxadiazole, thiazole, tetrazole, indole, carbazole, pyrroloimidazole, pyrrolopyrrole, thienopyrrole, thienothiophene, furopyrrole, furofuran, thienofuran, benzisoxazole, benzisothiazole, benzimidazole, pyridine, pyrazine, pyridazine, pyrimidine, triazine, quinoline, isoquinoline, cinnoline, quinoxaline, phenanthridine, primidine, quinazoline, quinazolinone and derivatives thereof.

In the present embodiment, ring F is an aromatic ring system containing 6 to 20 ring atoms; in an embodiment, ring F is an aromatic ring system containing 6 to 15 ring atoms; in one embodiment, ring F is an aromatic ring system containing 6 to 10 ring atoms.

In certain embodiments, F is one selected from the following structural groups:

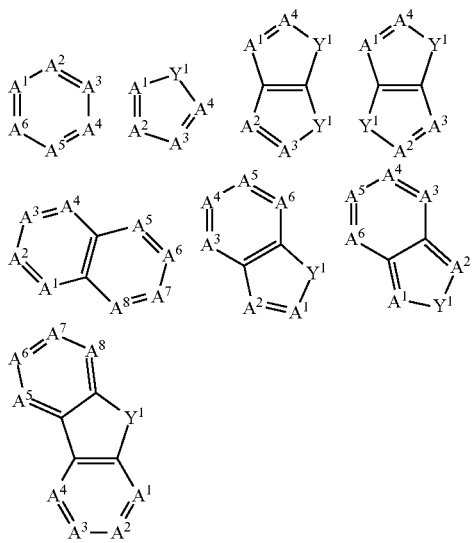

wherein
$A^1$, $A^2$, $A^3$, $A^4$, $A^5$, $A^6$, $A^7$, $A^8$ independently represent $CR^5$ or N;
$Y^1$ is selected from $CR^6R^7$, $SiR^8R^9$, $NR^{10}$, C(=O), S or O;
$R^5$ to $R^{10}$ are each independently selected from H, D, or a linear alkyl group containing 1 to 20 C atoms, or an alkoxy group containing 1 to 20 C atoms, or a thioalkoxy group containing 1 to 20 C atoms, or a branched or a cyclic alkyl group containing 3 to 20 C atoms, or an alkoxy group containing 3 to 20 C atoms, or a thioalkoxy group containing 3 to 20 C atoms, or a silyl group, or a substituted keto group containing 1 to 20 C atoms, or an alkoxycarbonyl group containing 2 to 20 C atoms, or an aryloxycarbonyl group containing 7 to 20 C atom, a cyano group (—CN), a carbamoyl group (—C(=O)NH$_2$), a haloformyl group (—C(=O)—X, wherein X represents a halogen atom), a formyl group (—C(=O)—H), an isocyano group, an isocyanate group, a thiocyanate group, an isothiocyanate group, a hydroxyl group, a nitryl group, a CF$_3$ group, Cl, Br, F, a crosslinkable group, or a substituted or unsubstituted aromatic ring system containing 5 to 40 ring atoms or a substituted or unsubstituted heteroaromatic ring system containing 5 to 40 ring atoms, or an aryloxy group containing 5 to 40 ring atoms or a heteroaryloxy group containing 5 to 40 ring atoms; wherein one or more of $R^5$ to $R^{10}$ may form a monocyclic or polycyclic aliphatic or aromatic ring with each other or with a ring bonded to the groups.

In an embodiment, F may further be one selected from the following structural groups, wherein H in the rings may be optionally substituted:

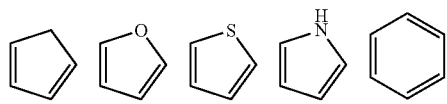

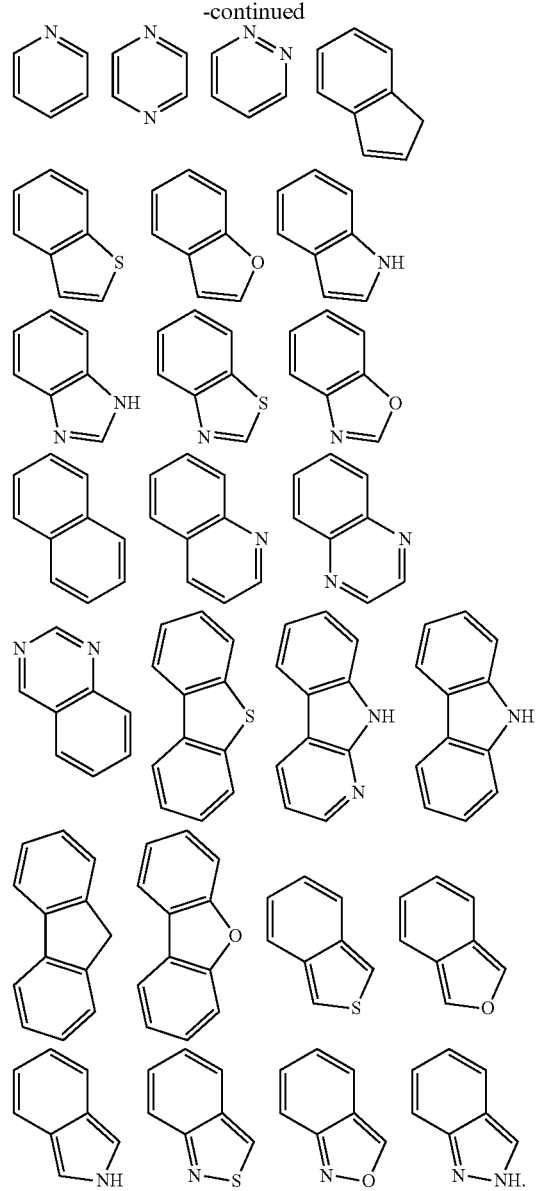

Generally, energy level structure, such as triplet excited state energy level T1, of an organic compound, depends on the substructure having the largest conjugated system of the compound. Generally, T1 decreases as the conjugated system increases. In an embodiment, when n is 0, the general formula (II) has a structure represented by the following general formula (IIa), which has the largest conjugated system.

(IIa)

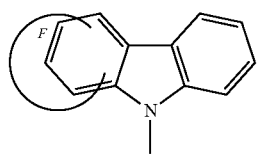

In an embodiment, the general formula (IIa) has no more than 30 ring atoms in the case of removing substituents. In an embodiment, the general formula (IIa) has no more than 26 ring atoms in the case of removing substituents. In an embodiment, the general formula (IIa) has no more than 22 ring atoms in the case of removing substituents. In an embodiment, the general formula (IIa) has no more than 20 ring atoms in the case of removing substituents.

The general formula (IIa) has a higher triplet excited state energy level T1, in an embodiment, T1≥2.2 eV; In an embodiment, T1≥2.4 eV; In an embodiment, T1≥2.5 eV; In an embodiment, T1≥2.6 eV; In an embodiment, T1≥2.7 eV.

In an embodiment, in the foregoing conjugated polymer, A is selected from the group consisting of the following structures:

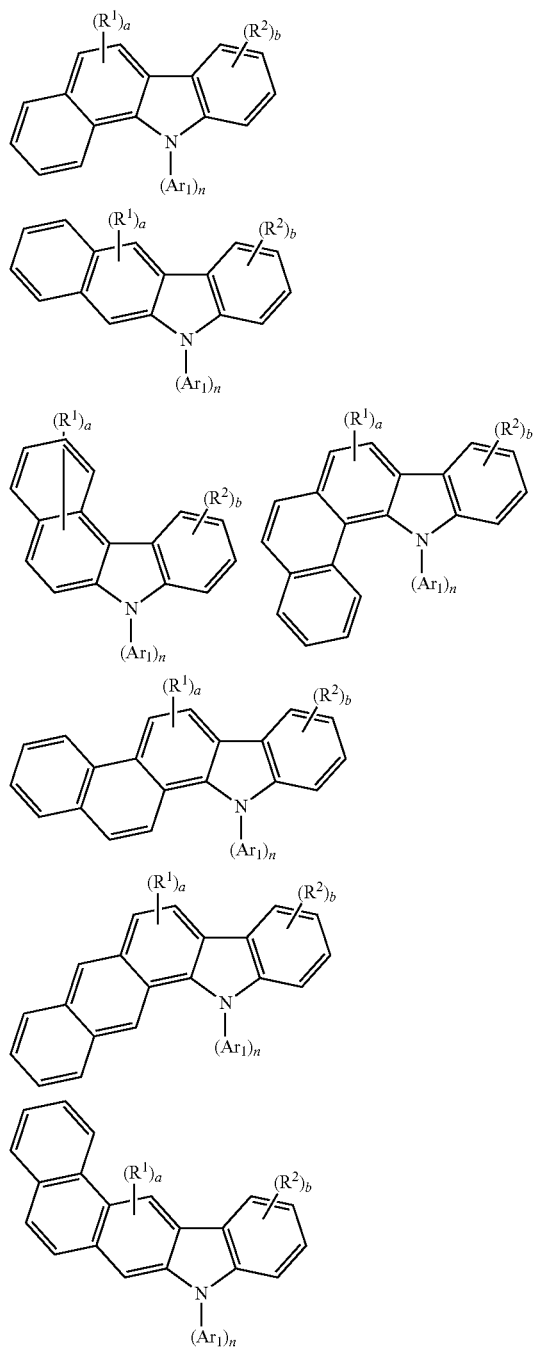

-continued

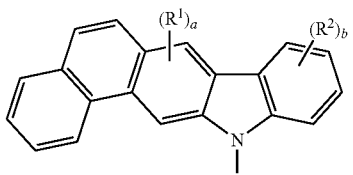

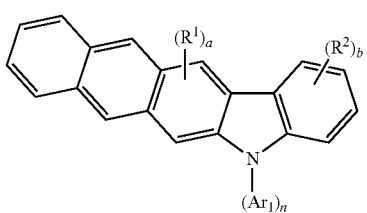

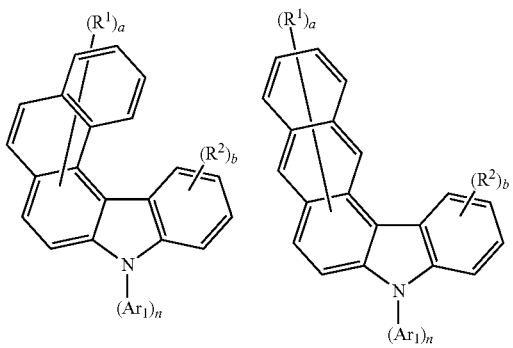

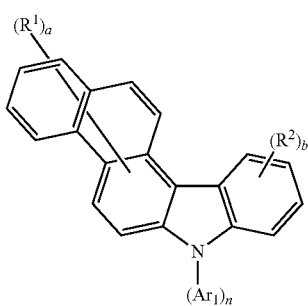

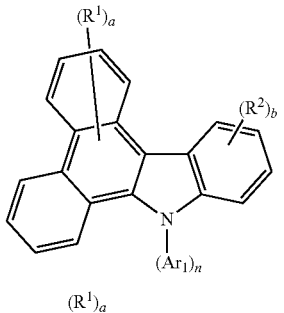

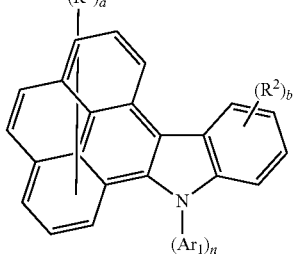

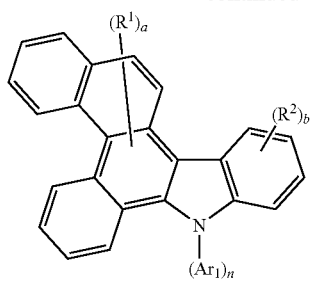
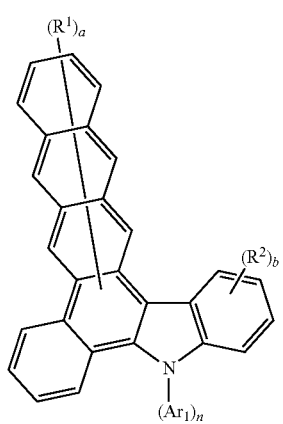
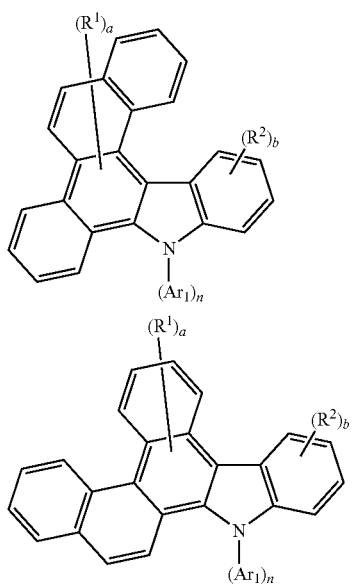
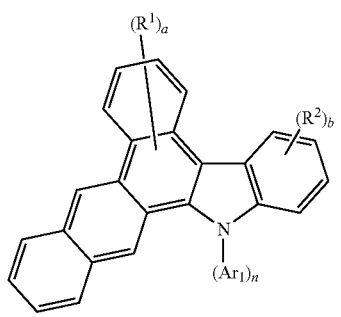
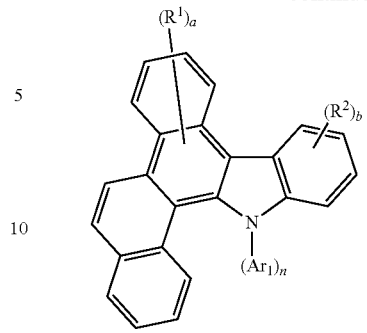
wherein a, b, $R^1$, $R^2$, $Ar^1$, n are defined as above.
In an embodiment, in the foregoing conjugated polymer, A in the repeating unit represented by the general formula (I) is selected from the group consisting of the following structures:
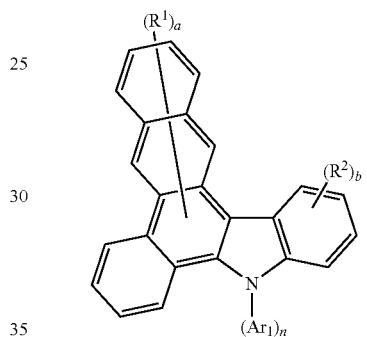
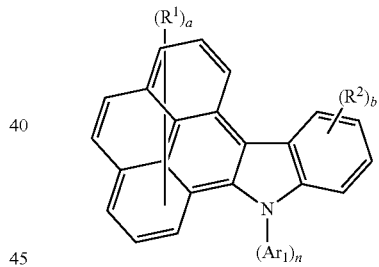
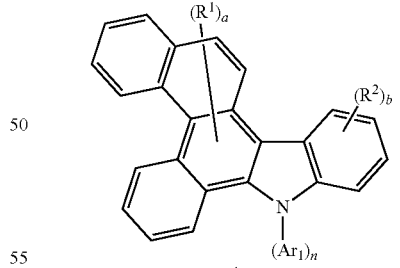
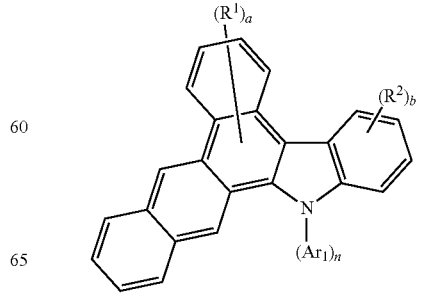

-continued
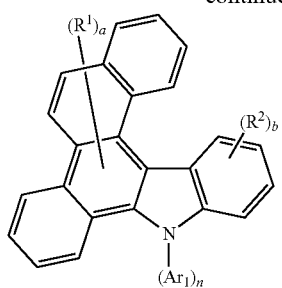
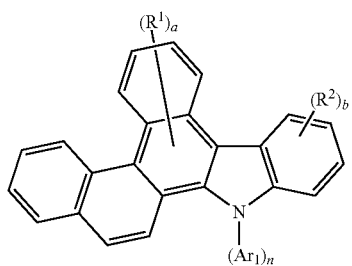
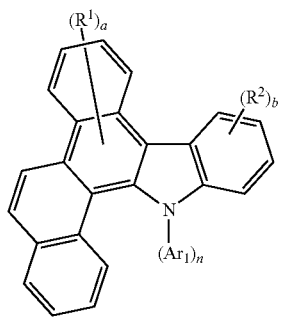
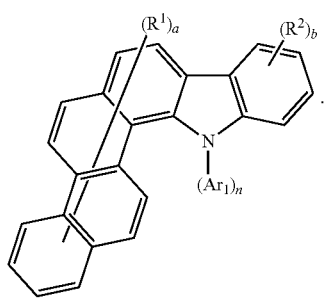
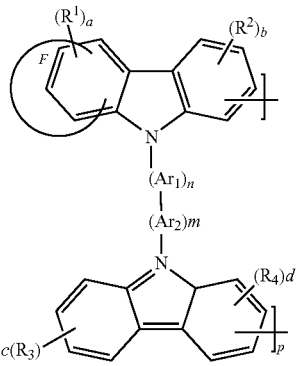
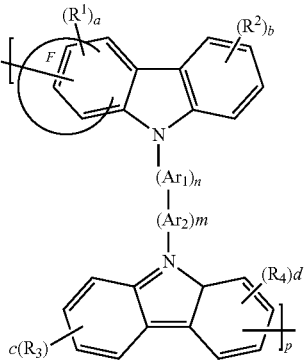
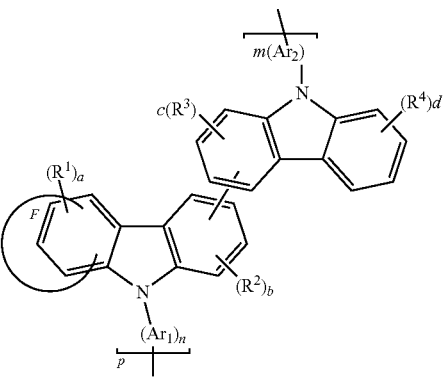
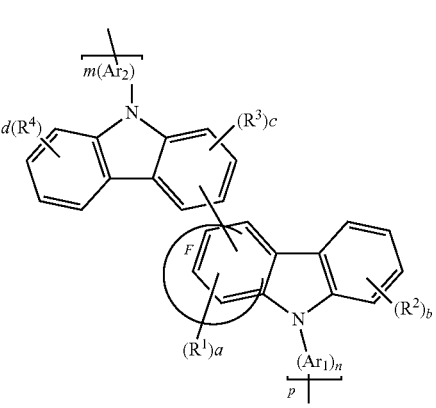
In the general formula (I), there can be various linking ways between A and B.
In an embodiment, the foregoing conjugated polymer includes a repeating unit represented by one of the following general formulas:

(I-7)

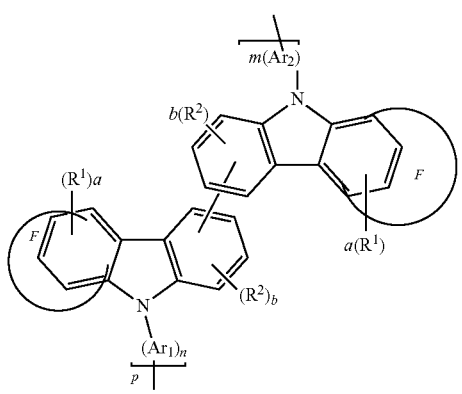

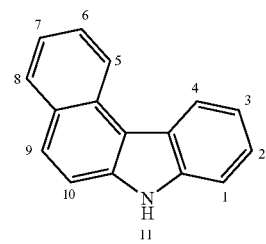
A-03

The corresponding substructure of the unit B is as shown in the following structure B-01:

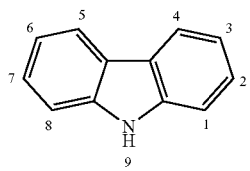
B-01

(I-8)

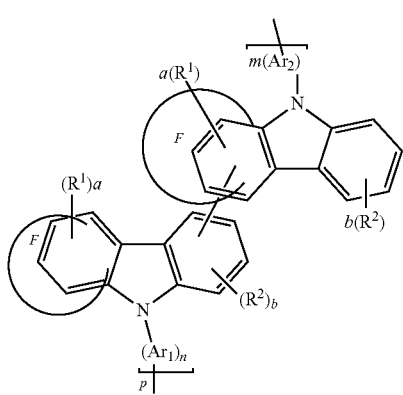

wherein $R^1$, $R^2$, $R^3$, $R^4$, a, b, c, d, m, n, $Ar^1$, $Ar^2$, F are defined as in the general formula (I).

In an embodiment, in the foregoing conjugated polymer, the substructure (11a) of the unit A is selected from the group consisting of the structures represented by A-01 to A-03:

A-01

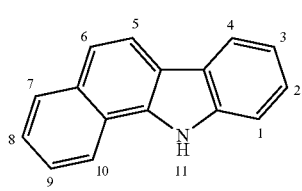

A-02

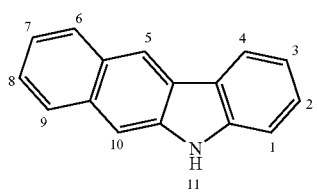

In an embodiment, in the foregoing conjugated polymer, the unit A, the unit B and the other units A, B in the backbone are linked in the following way: the positions 1 to 11 of the units A-01 to A-03, the positions 1 to 9 of the unit B-01, and the positions 1 to 11 of the other units A-01 to A-03, the positions 1 to 9 of the unit B-01, $Ar_1$ or $Ar_2$ are directly linked by C—C bonds. In an embodiment, the position 9 of the unit B-01 is linked to the position 11 of the units A-01 to A-03; in an embodiment, the position 9 of the unit B-01 is linked to the positions 1 to 4 of the units A-01 to A-03; in an embodiment, the positions 11 of the units A-01 to A-03 are linked to the positions 1 to 4 of the unit B-01; in an embodiment, the positions 3 of the units A-01 to A-03 are linked to the position 3 of the unit B-01;

In an embodiment, the foregoing conjugated polymer further includes another repeating unit having the following general formula (IV) in the backbone:

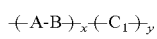 (IV)

wherein x, y are the molar percentage (mol %) of the repeating units, x>0, y>0, and x+y=1, the repeating unit $C_1$ may be same or different at multiple occurrences, and is an aromatic ring group or a heteroaromatic ring group; wherein the aromatic ring group includes benzene, biphenyl, triphenyl, benzo, fluorene, indenofluorene and derivatives thereof; the heteroaromatic ring group includes triphenylamine, dibenzothiophene, dibenzofuran, dibenzoselenophen, furan, thiophene, benzofuran, benzothiophene, benzoselenophene, carbazole, indolocarbazole, indolopyridine, pyrrolopyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazin, oxadiazine, indole, benzimidazole, indazole, benzisoxazole, dibenzoxazole, isoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furodipyridine, benzothienopyridine, thienodipyridine, benzoselenophenopyridine, selenophenodipyridine, and the like.

In another embodiment, the repeating unit $C_1$ may be same or different at multiple occurrences, and is selected from the following structural groups, wherein H in the rings may be optionally substituted:
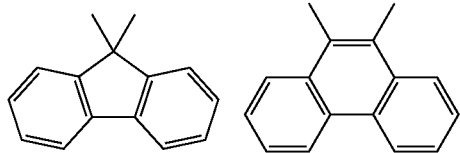
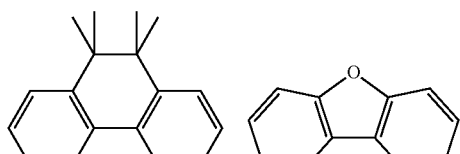
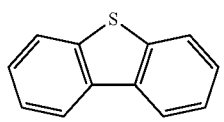
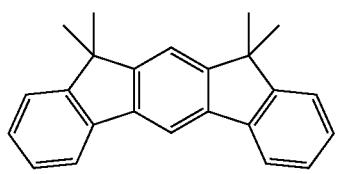
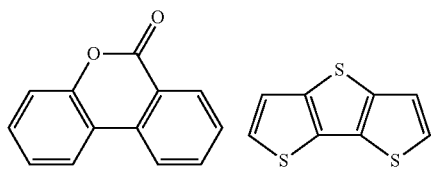
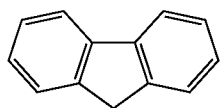
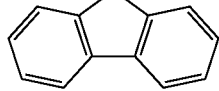
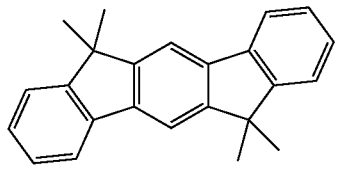
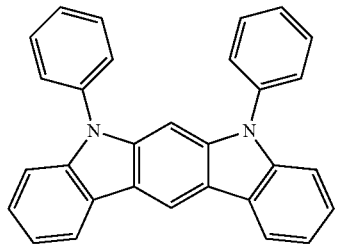
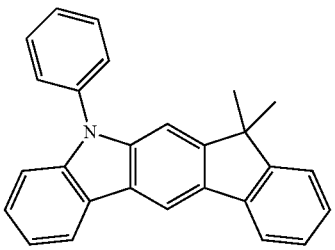
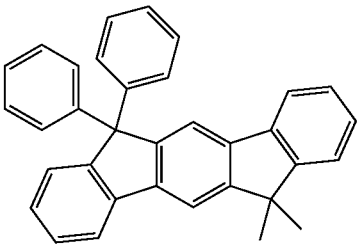
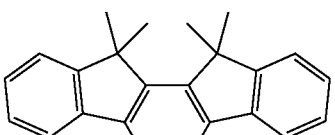
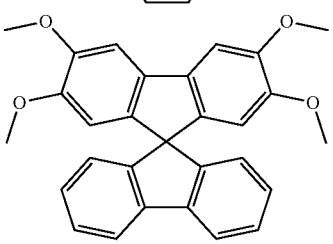
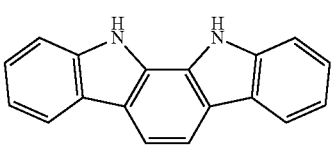
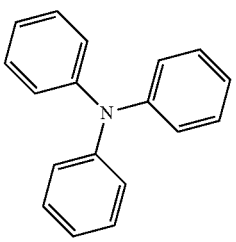
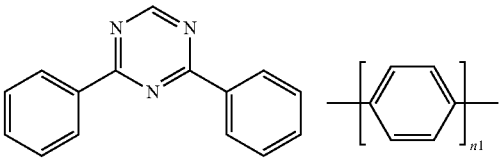
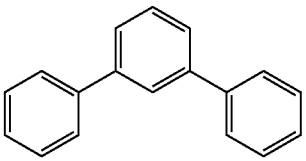

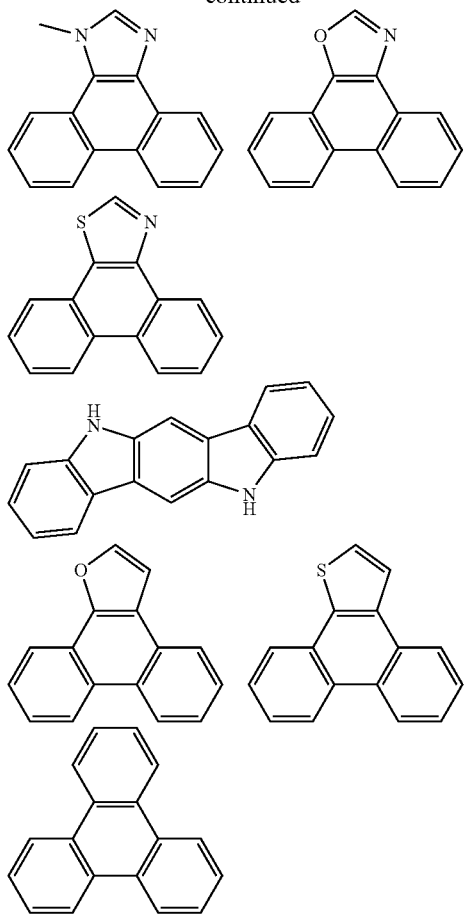

wherein n1 is 1, 2, 3 or 4.

In a further embodiment, the repeating unit C1 may be same or different at multiple occurrences, and is selected from other organic optoelectronic functional groups, the organic optoelectronic function includes a hole (also called electron hole) injection or transporting function, a hole blocking function, en electron injection or transporting function, an electron blocking function, an organic host function, a singlet light-emitting function (a fluorescent function), a triplet light-emitting function (a phosphorescent function). Suitable organic optoelectronic functions can be referred to the corresponding organic functional materials, including a hole (also known as electron hole) injection or transporting material (HIM/HTM), a hole blocking material (HBM), an electron injection or transporting material (EIM/ETM), an electron blocking material (EBM), an organic host material (Host), a singlet emitter (a fluorescent emitter), a triplet emitter (a phosphorescent emitter), particularly a light-emitting organometallic clathrate. Various organic functional materials are described in detail, for example, in WO2010135519A1, US20090134784A1 and WO2011110277A1, the entire contents of which three patent documents are incorporated herein by reference.

In an embodiment, the foregoing conjugated polymer has a hole transporting function and can be used in an organic electronic device, particularly in a hole transporting layer in an OLED.

In another embodiment, the foregoing conjugated polymer has a higher LUMO and an electron blocking function, and can be used in an organic electronic device, particularly in an electron blocking layer in an OLED. The higher LUMO here refers to the LUMO higher than that of an adjacent functional layer, such as a light-emitting layer in an OLED.

In another embodiment, the foregoing conjugated polymer has a higher triplet excited state energy level T1 and a triplet exciton blocking function, and can be used in an organic electronic device, particularly in an exciton blocking layer in a phosphorescent OLED. The higher T1 here refers to the T1 higher than that of an adjacent functional layer, such as a light-emitting layer in a phosphorescent OLED.

In another embodiment, the foregoing conjugated polymer has a higher singlet excited state energy level S1 and a singlet exciton blocking function, and can be used in an organic electronic device, particularly in an exciton blocking layer in a fluorescent OLED. The higher S1 here refers to the S1 higher than that of an adjacent functional layer, such as a light-emitting layer in a fluorescent OLED.

In an embodiment, the repeating unit C may be same or different at multiple occurrences, and is selected from organic optoelectronic functional groups having a hole transporting function, i.e., an HTM or HIM group.

A suitable organic HTM or HIM group may be selected from the groups having the following structural units: phthalocyanine, porphyrin, amine, aryl amine, biphenyl triarylamine, thiophene, fused thiophene (such as dithienothiophene and dibenzothiophene), pyrrole, aniline, carbazole, indolocarbazole, and derivatives thereof.

In an embodiment, an electron blocking layer (EBL) is used to block electrons from adjacent functional layers, particularly the light-emitting layer. Compared with a light-emitting device without a blocking layer, the presence of EBL usually leads to an increase in luminous efficiency. The electron blocking material (EBM) of the electron blocking layer (EBL) requires a higher LUMO than an adjacent functional layer such as a light-emitting layer. In an embodiment, the EBM has a greater excited state energy level than the adjacent light-emitting layer, such as a singlet or triplet, depending on the emitter, while the EBM has a hole transporting function. An HIM/HTM group, which typically has a high LUMO energy level, can be used as an EBM group.

Particularly, examples of cyclic aryl amine-derived groups that can be used as HIM, HTM or EBM groups include, but are not limited to, the following general structures:

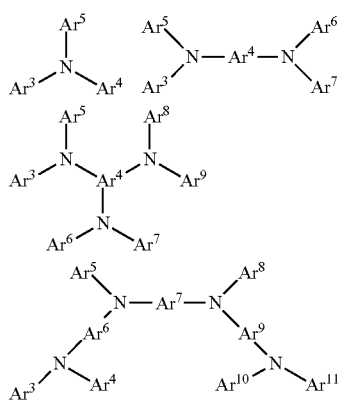

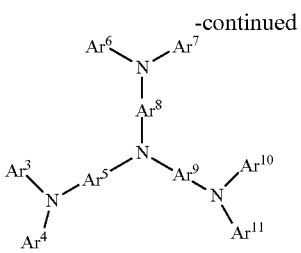

Each of Ar³ to Ar¹¹ may be independently selected from a cyclic aromatic hydrocarbon compound, such as benzene, biphenyl, triphenyl, benzo, naphthalene, anthracene, phenalene, phenanthrene, fluorene, pyrene, chrysene, perylene, and azulene; and a heteroaromatic ring compound, such as dibenzothiophene, dibenzofuran, furan, thiophene, benzofuran, benzothiophene, carbazole, pyrazole, imidazole, triazole, isoxazole, thiazole, oxadiazole, oxytriazole, dioxazole, thiadiazole, pyridine, pyridazine, pyrimidine, pyrazine, triazine, oxazine, oxathiazine, oxadiazine, indole, benzimidazole, indazole, indolizine, benzoxazole, benzisoxazole, benzothiazole, quinoline, isoquinoline, cinnoline, quinazoline, quinoxaline, naphthalene, phthalein, pteridine, xanthene, acridine, phenazine, phenothiazine, phenoxazine, dibenzoselenophene, benzoselenophene, benzofurapyridine, indolocarbazole, pyridine indole, dipyridinipyrrole, dipyridine furan, benzothienopyridine, thiophene pyridine, benzoselenophen pyridine and dipyridyl selenophene; and a group including 2 to 10 ring structures, which may be the same or different types of cyclic aromatic hydrocarbonyl groups or heteroaromatic ring groups, and are bonded to each other directly or through at least one of the following groups: an oxygen atom, a nitrogen atom, a sulfur atom, a silicon atom, a phosphorus atom, a boron atom, a chain structure unit, and an aliphatic ring group. Each Ar may be further substituted, and the substituent may be selected from the group consisting of deuterium, alkyl, alkoxy, amino, alkene, alkyne, aralkyl, heteroalkyl, aryl or heteroaryl.

In one aspect, Ar³ to Ar¹¹ may be independently selected from the groups including the follows:

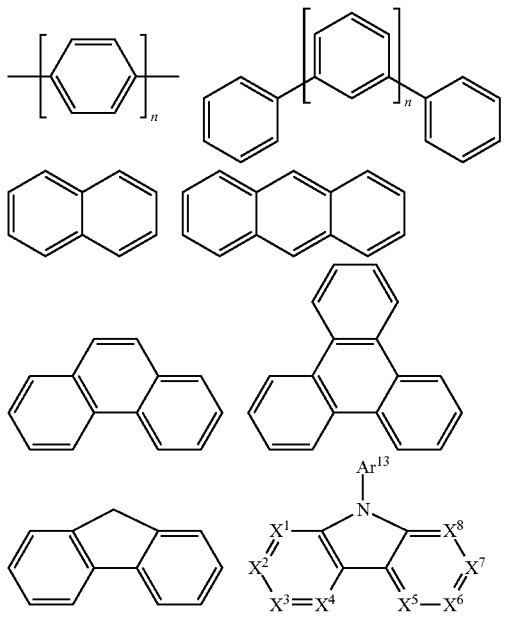

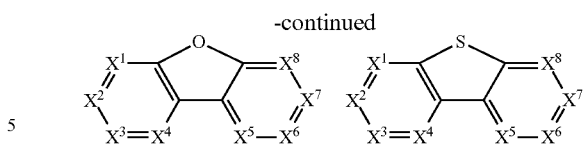

n is an integer from 1 to 20; $X^1$ to $X^8$ are CH or N; $Ar^{13}$ is as the above $Ar^1$.

Additional examples of compounds corresponding to the cyclic aryl amine-derived groups as the HTM or HIM groups can be found in U.S. Pat. Nos. 3,567,450, 4,720,432, 5,061,569, 3,615,404, and 5,061,569.

In an embodiment, the foregoing conjugated polymer has a molar ratio of A-B to C ranging from 10:90 to 90:10. In an embodiment, the foregoing conjugated polymer has a molar ratio of A-B to C ranging from 20:80 to 80:20. In an embodiment, the foregoing conjugated polymer has a molar ratio of A-B to C ranging from 30:70 to 70:30. In an embodiment, the foregoing conjugated polymer has a molar ratio of A-B to C ranging from 40:60 to 60:40.

In another embodiment, the foregoing conjugated polymer includes a singlet light-emitting group or a triplet light-emitting group.

In an embodiment, the HTL in a solution processed OLED device is curable to facilitate formation of a multilayer structure.

In an embodiment, the foregoing conjugated polymer has the following general formula (V):

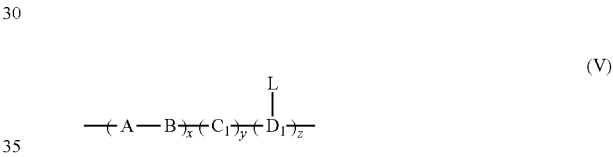

wherein L is a crosslinkable group, and $D_1$ may be same or different in multiple occurrences, and is an aromatic ring group or a heteroaromatic ring group; wherein the aromatic ring group includes benzene, biphenyl, triphenyl, benzo, fluorene, indenofluorene and derivatives thereof; the heteroaromatic ring group includes triphenylamine, dibenzothiophene, dibenzofuran, dibenzoselenophen, furan, thiophene, benzofuran, benzothiophene, benzoselenophene, carbazole, indolocarbazole, indolopyridine, pyrrolopyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazin, oxadiazine, indole, benzimidazole, indazole, benzisoxazole, dibenzoxazole, isoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furodipyridine, benzothienopyridine, thienodipyridine, benzoselenophenopyridine, selenophenodipyridine, and the like.

x>0, y≥0, z>0, and x+y+z=1, particularly y>0.

In an embodiment, the repeating unit $D_1$ may be same or different in multiple occurrences, and is selected from organic optoelectronic functional groups having a hole transporting function, i.e., an HTM or HIM group. A suitable HTM or HIM group is as described above.

In an embodiment, in the foregoing conjugated polymer, the crosslinkable group L is selected from the group consisting of 1) a linear alkenyl, a cyclic alkenyl, a linear dienyl and an alkynyl; 2) an alkenyloxy, a dienyloxy group; 3) an acrylic group; 4) an epoxypropyl group and an oxirane group; 5) a silane group; 6) a cyclobutyl group.

In an embodiment, the crosslinkable group L is selected from the group consisting of
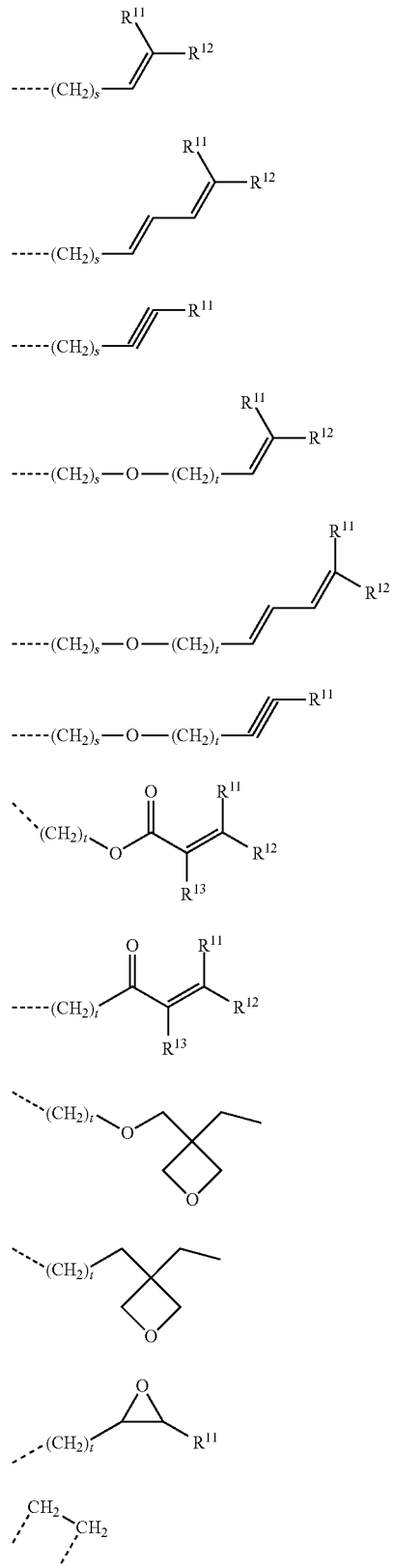
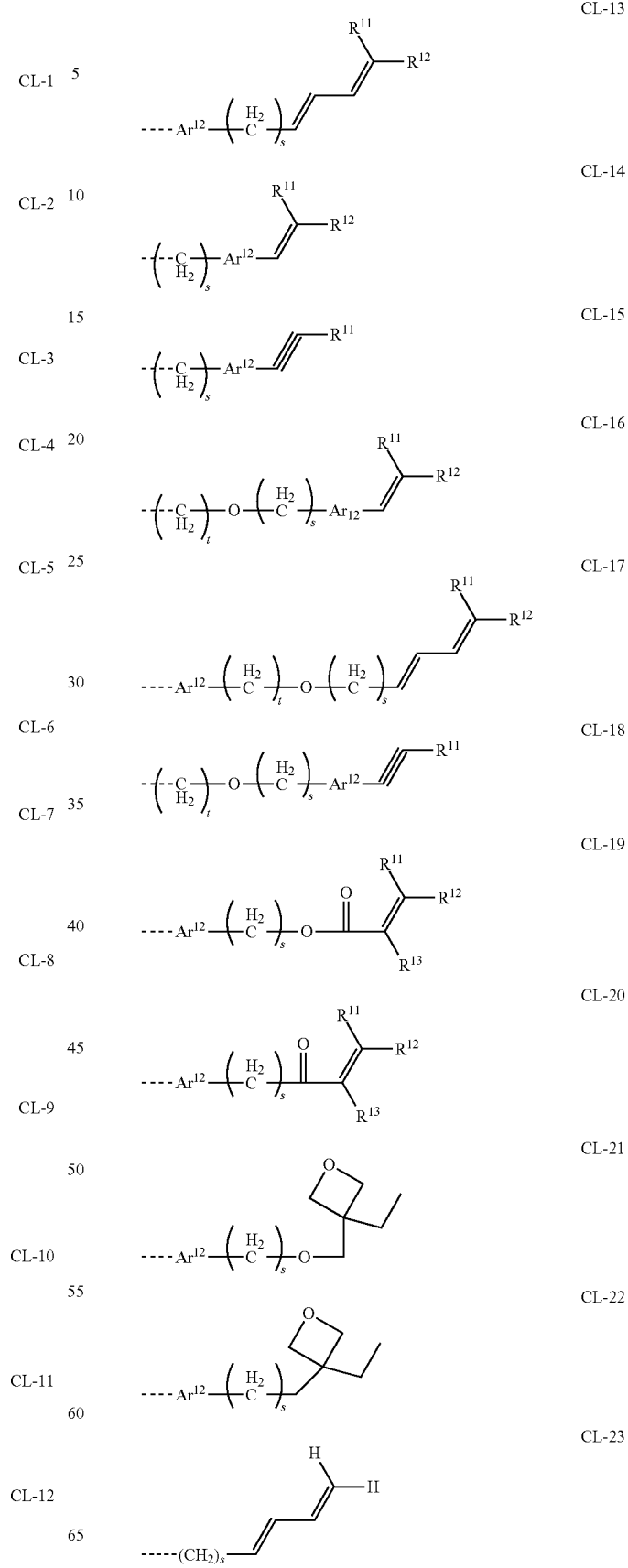

-continued

CL-24
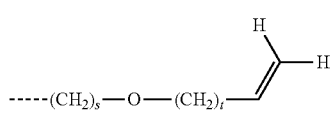

CL-25

CL-26
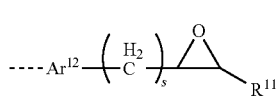

CL-27
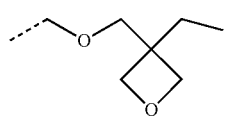

CL-28
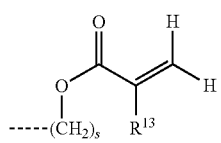

CL-29
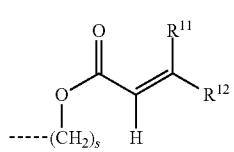

CL-30
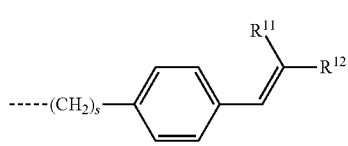

CL-31
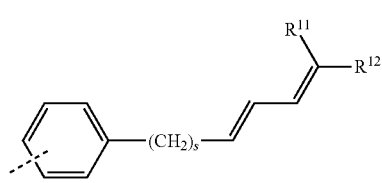

CL-32
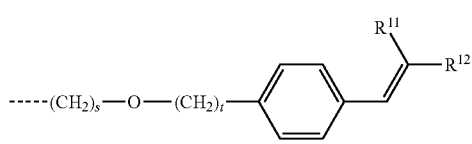

CL-33
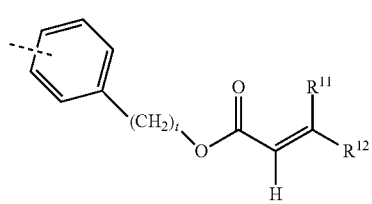

CL-34
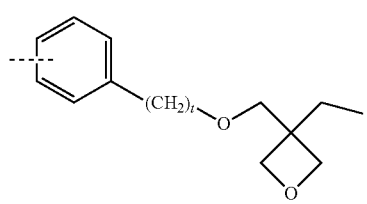

CL-35
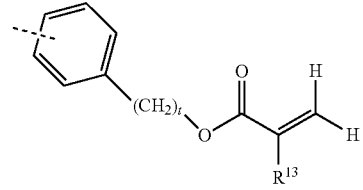

CL-36

wherein $R^{11}$, $R^{12}$ and $R^{13}$ are each independently selected from the group consisting of H, D, F, CN, an alkyl chain, a fluoroalkyl chain, an aromatic ring, a heteroaromatic ring, an amino group, a silicon group, a methyl germanium group, an alkoxy group, an aryloxy group, a fluoroalkoxy group, a siloxane, a siloxy group, a crosslinkable group, a deuterated alkyl chain, a deuterated partially-fluorinated alkyl chain, a deuterated aromatic ring, a deuterated heteroaromatic ring, a deuterated amino group, a deuterated silicon group, a deuterated methyl germanium group, a deuterated alkoxy group, a deuterated aryloxy group, a deuterated fluoroalkoxy group, a deuterated siloxane, a deuterated siloxy group.

In other words, the hydrogen atoms in the alkyl chain, fluoroalkyl chain, aromatic ring, heteroaromatic ring, amino group, silicon group, methyl germanium group, alkoxy group, aryloxy group, fluoroalkoxy, siloxane, siloxy group are optionally substituted with one or more deuterium atoms, the adjacent $R^{11}$, $R^{12}$, and $R^{13}$ may form a monocyclic or polycyclic aliphatic or aromatic ring system with each other or with a ring bonded to said groups;

$Ar^{12}$ is an aromatic ring system containing 5 to 40 ring atoms or a heteroaromatic ring system containing 5 to 40 ring atoms.

In an embodiment, ($D_1$-L) has a molar percentage z ranging from 1% to 30% in the foregoing conjugated polymer. In an embodiment, ($D_1$-L) has a molar percentage z ranging from 5% to 25% in the foregoing conjugated polymer. In an embodiment, ($D_1$-L) has a molar percentage z ranging from 5% to 20% in the foregoing conjugated polymer. In an embodiment, ($D_1$-L) has a molar percentage z ranging from 10% to 20% in the foregoing conjugated polymer.

In an embodiment, the crosslinking monomer ($D_1$-L) is selected from the following structures:

CLG-1
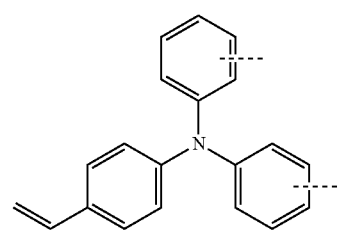

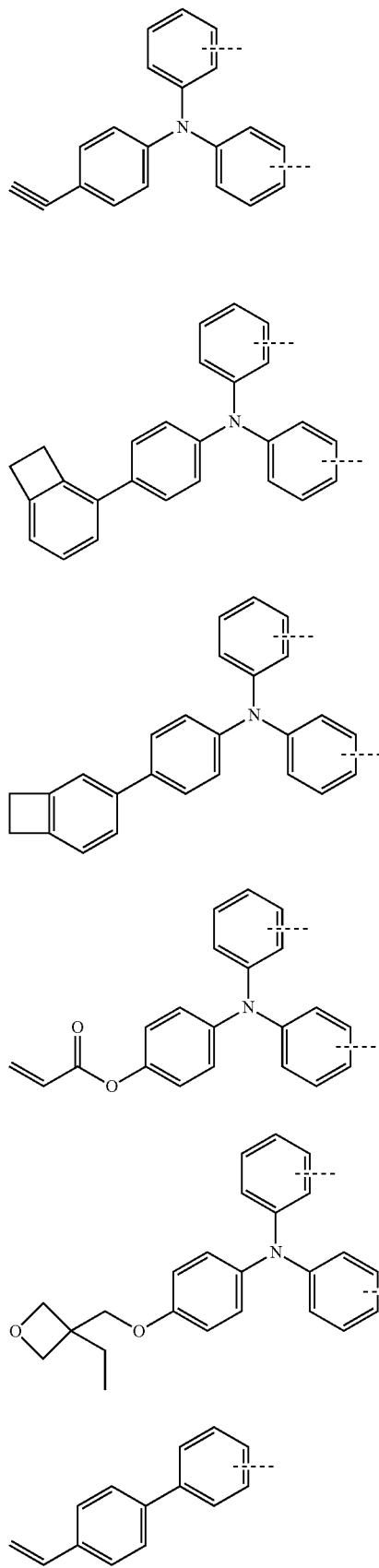
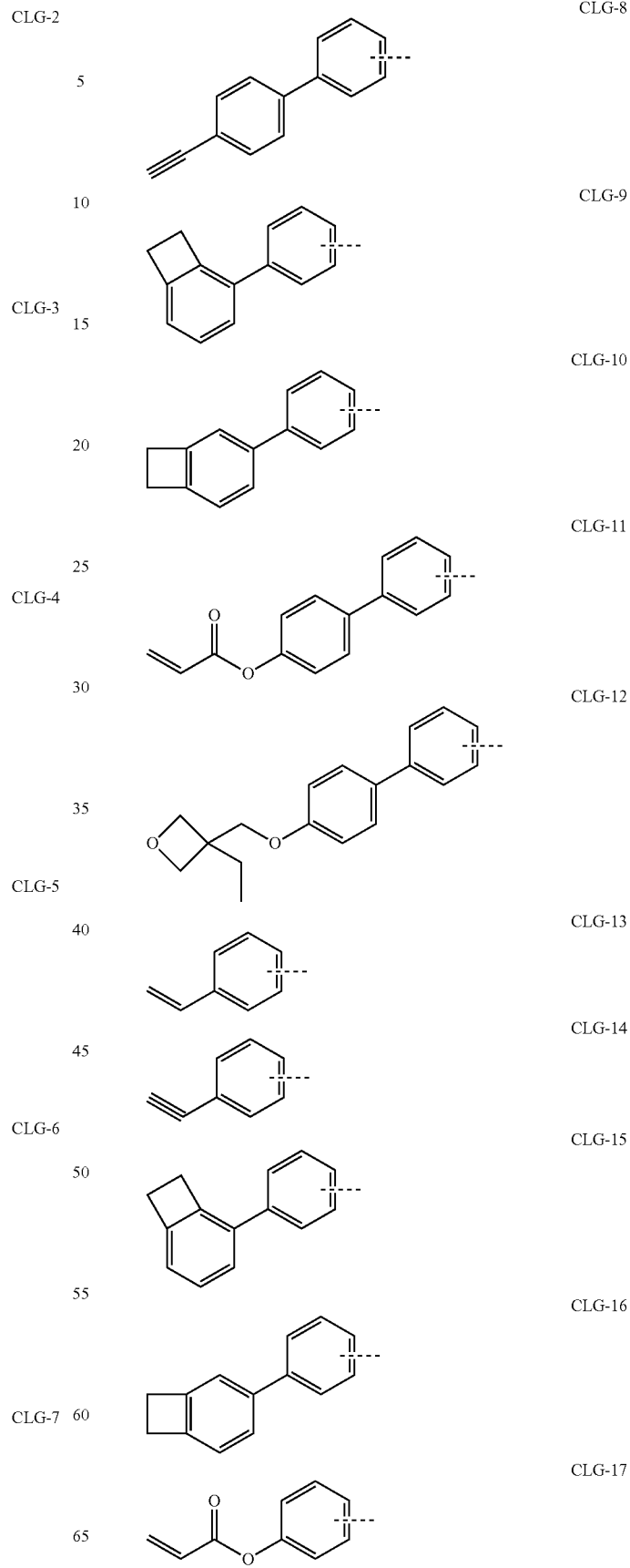

CLG-18

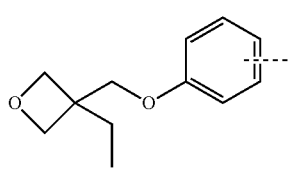

wherein the dotted line represents the position at which the crosslinking monomer is bonded to another monomer or a functional group in another monomer in the foregoing conjugated polymer.

In certain embodiments, the foregoing polymer includes at least one deuterium atom.

The present disclosure further relates to a polymeric monomer having any one of the structures represented by the following general formulas (X-1) to (X-8):

(X-1)
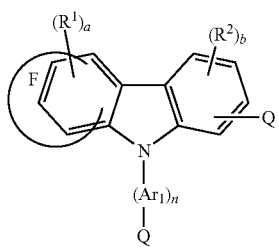

(X-3)
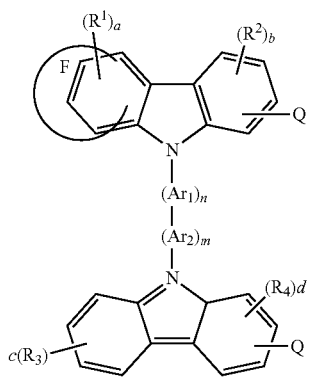

(X-4)
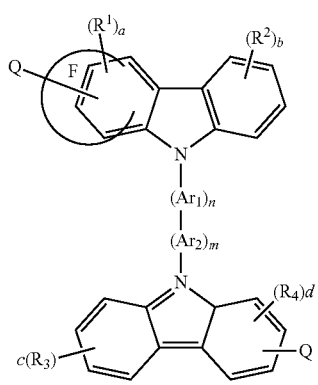

(X-5)
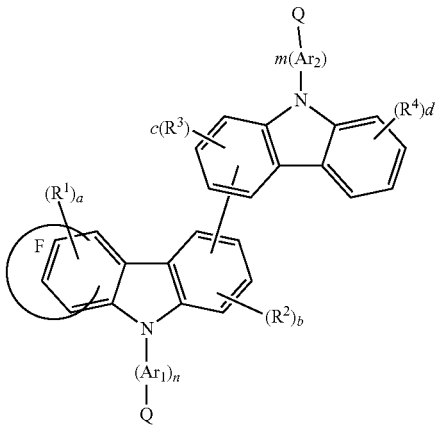

(X-2)
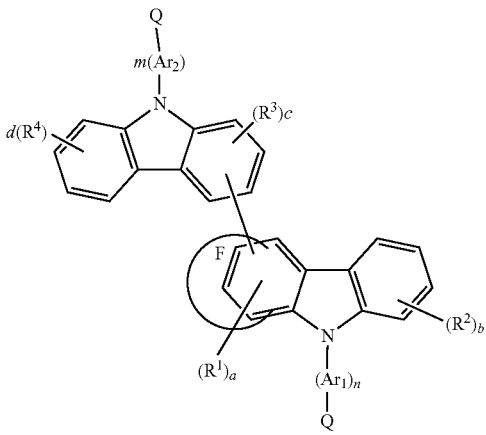

(X-6)
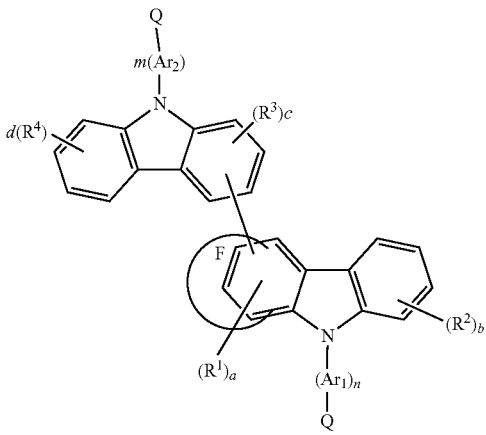

(X-7)
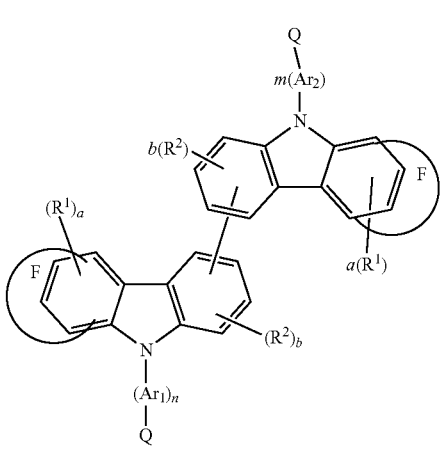

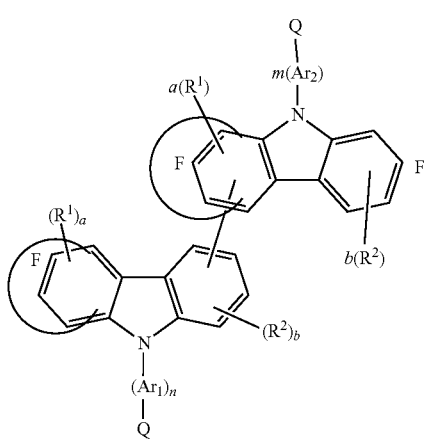

(X-8)

wherein Q is a leaving group;

The definitions and examples of $R^1$, $R^2$, $R^3$, $R^4$, a, b, c, d, n, m, F, $Ar_1$, and $Ar_2$ are as described above.

In an embodiment, the leaving group is selected from the group consisting of Cl, Br, I, o-tosylate, o-triflate, o-mesylate, o-nonaflate, NH, $SiMe_{3-n}F_n$ (n=1 or 2), $O-SO_2R^{11}$, $B(OR^{11})_2$, $-CR^{11}=C(R^1)_2$, $-C\equiv CH$, and $Sn(R^{11})_3$, in an embodiment, the leaving group Q is selected from Br, I, or $B(OR^1)_2$;

wherein $R^{11}$ is selected from the group consisting of H, D, F, CN, an alkyl chain, a fluoroalkyl chain, an aromatic ring, a heteroaromatic ring, an amino group, a silicon group, a methyl germanium group, an alkoxy group, an aryloxy group, a fluoroalkoxy group, a siloxane, a siloxy group, a crosslinkable group; the hydrogen atoms of said alkyl chain, fluoroalkyl chain, aromatic ring, heteroaromatic ring, amino group, silicon group, methyl germanium group, alkoxy group, aryloxy group, fluoroalkoxy, siloxane, siloxy group are optionally substituted with one or more deuterium atoms;

the adjacent $R^{11}$'s may form a monocyclic or polycyclic aliphatic or aromatic ring system with each other or with the ring bonded to said groups;

n is 1 or 2.

In an embodiment, the polymeric monomer is selected from the following structures:

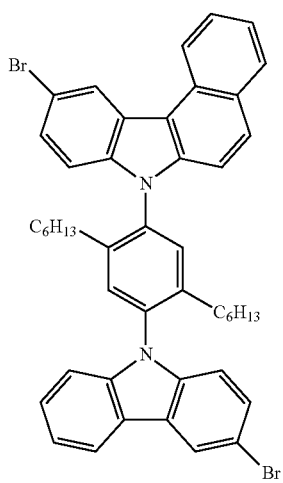

(M-1)

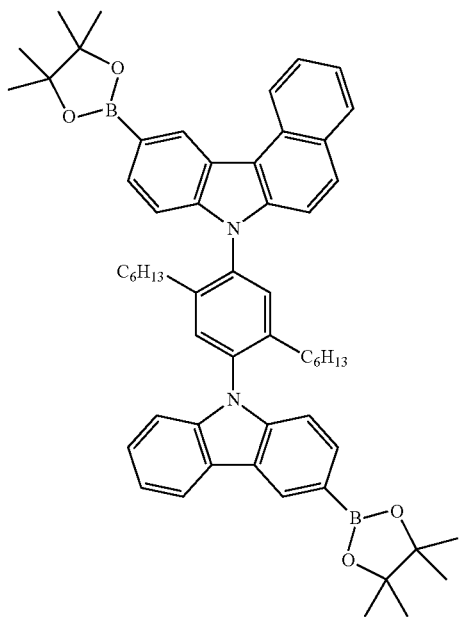

(M-2)

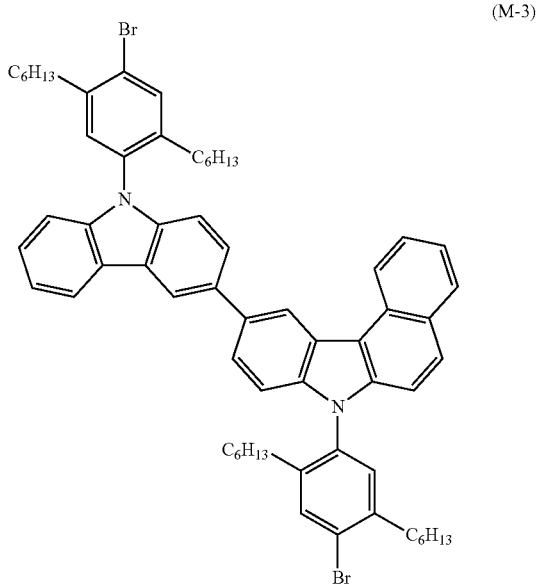

(M-3)

(M-4)
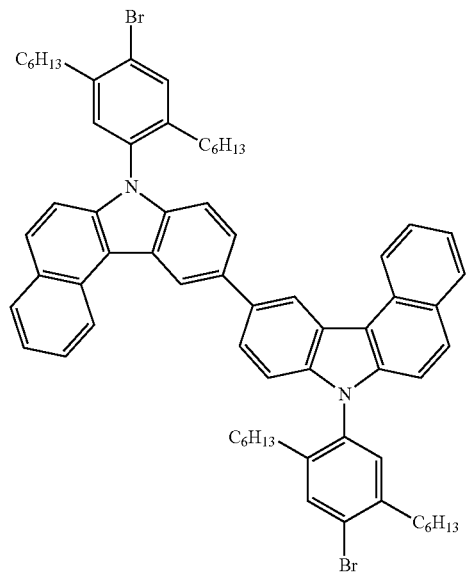
(M-5)
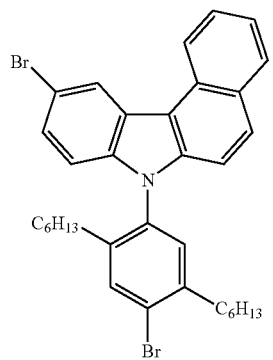
(M-6)
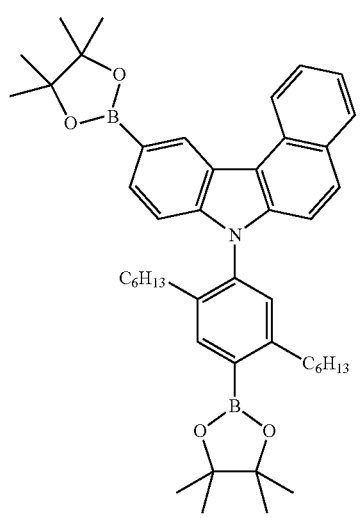
(M-7)
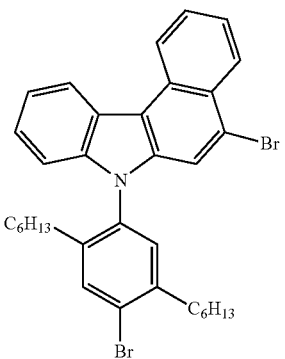
(M-8)
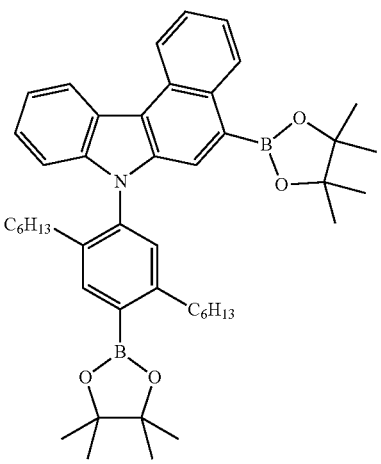
(M-9)
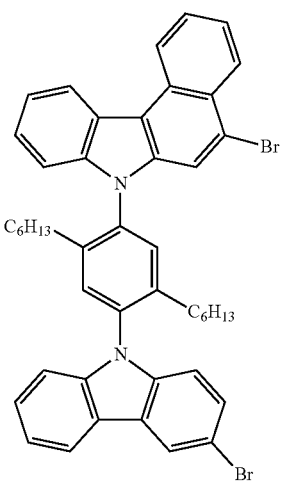

(M-10)
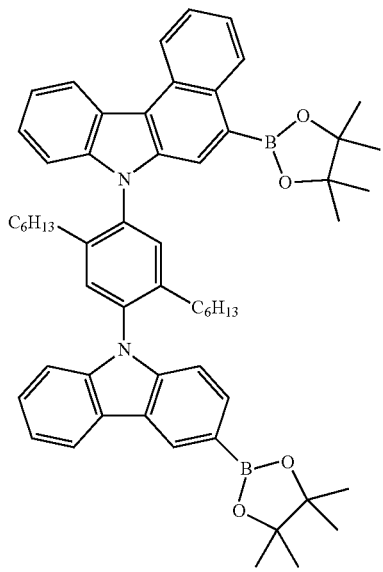
(M-11)
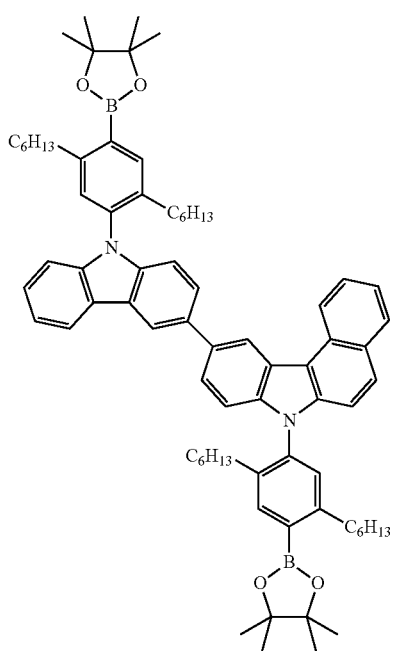
(M-12)
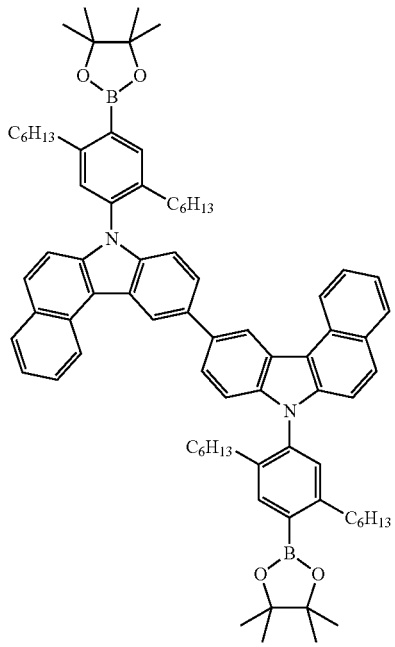
(M-13)
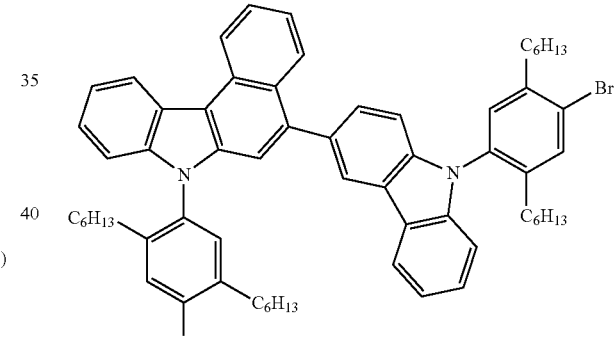
(M-14)
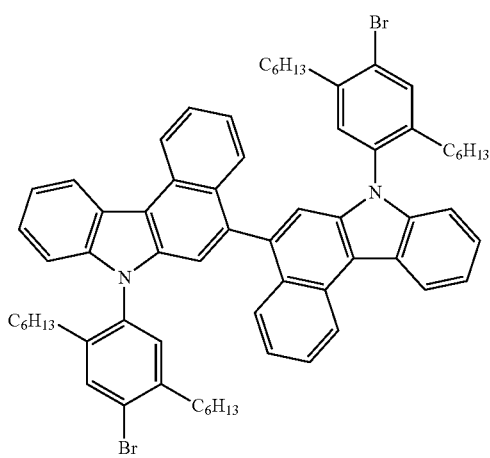

-continued

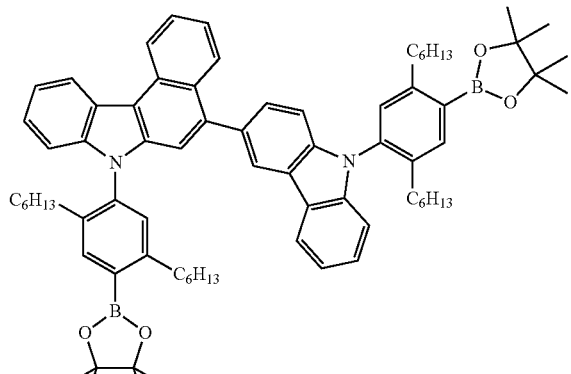

(M-15)

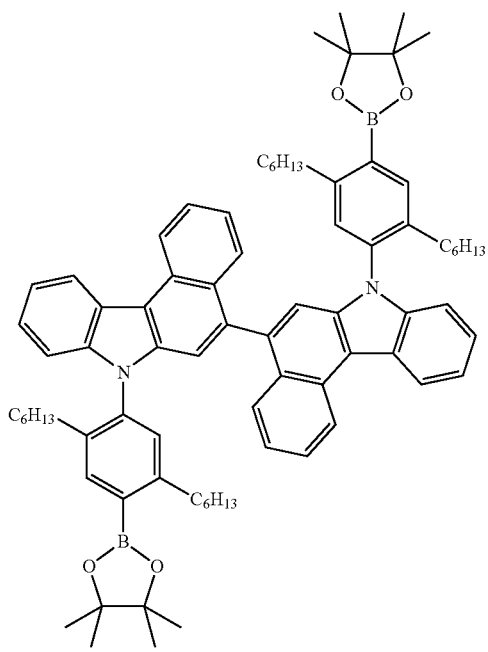

(M-16)

Ar₁ or Ar₂ in all the above general formulas is independently a substituted or unsubstituted aromatic structure containing 5 to 60 C atoms, or a heteroaromatic ring structure containing 5 to 60 C atoms, and may be any known or newly-developed functional compound for organic electronic devices without any limitation.

In an embodiment, Ar₁ and Ar₂ are the same or different in multiple occurrences, and is selected from an aromatic ring group or a heteroaromatic ring group. wherein the aromatic ring group includes benzene, biphenyl, triphenyl, benzo, fluorene, indenofluorene and derivatives thereof; the heteroaromatic ring group includes triphenylamine, dibenzothiophene, dibenzofuran, dibenzoselenophen, furan, thiophene, benzofuran, benzothiophene, benzoselenophene, carbazole, indolocarbazole, indolopyridine, pyrrolopyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazin, oxadiazine, indole, benzimidazole, indazole, benzisoxazole, dibenzoxazole, isoxazole, benzothiazole, quinoline, isoquinoline, cinnoline, quinazoline, quinoxaline, naphthalene, phthalein, pteridine, xanthene, acridine, phenazine, phenothiazine, phenoxazine, benzofuropyridine, furodipyridine, benzothienopyridine, thienodipyridine, benzoselenophenopyridine, selenophenodipyridine, and the like.

Further, the organic functional structural units Ar₁ and Ar₂ may be selected from organic functional groups corresponding to the following types of organic functional materials: a hole (also called electron hole) injection or transporting material (HIM/HTM), a hole blocking material (HBM), an electron injection or transporting material (EIM/ETM), an electron blocking material (EBM), an organic matrix material (Host), a singlet emitter (a fluorescent emitter). Various organic functional materials are described in detail, for example, in WO2010135519A1, US20090134784A1 and WO2011110277A1, the entire contents of which three patent documents are incorporated herein by reference.

In addition, in the polymer of the present disclosure, the single H atom or the $CH_2$ group may be substituted with a group R, and R is an alkyl group containing 1 to 40 C atoms, particularly selected from the group consisting of methyl, ethyl, propyl, isopropyl, cyclopropyl, n-butyl, isobutyl, sec-butyl, tert-butyl, cyclobutyl, methylbutyl, n-pentyl, sec-pentyl, cyclopentyl, n-hexyl, cyclohexyl, n-heptyl, cycloheptyl, n-octyl, cyclooctyl, ethylhexyl, trifluoromethyl, pentafluoroethyl, trifluoroethyl, vinyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl and octynyl. An alkoxy group containing 1 to 40 C atoms is considered to be methoxy, trifluoromethoxy, ethoxy, n-propoxy, isopropoxy, n-butoxy, isobutoxy, sec-butoxy, tert-butoxy or methylbutoxy.

In an embodiment, the foregoing conjugated polymer has a glass transition temperature greater than or equal to 100° C. In an embodiment, the foregoing conjugated polymer has a glass transition temperature greater than or equal to 120° C. In an embodiment, the foregoing conjugated polymer has a glass transition temperature greater than or equal to 140° C. In an embodiment, the foregoing conjugated polymer has a glass transition temperature greater than or equal to 160° C.

The foregoing conjugated polymer of the general formula (I) may be selected from the following structures:

Polymer 1

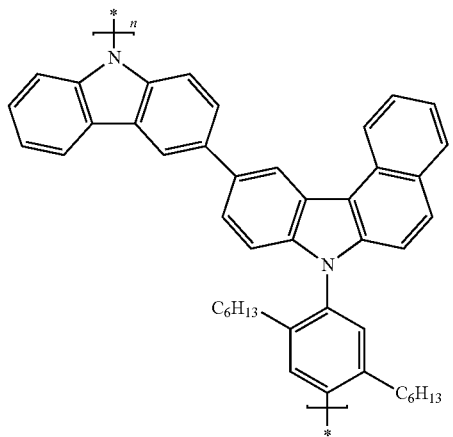

Polymer 2
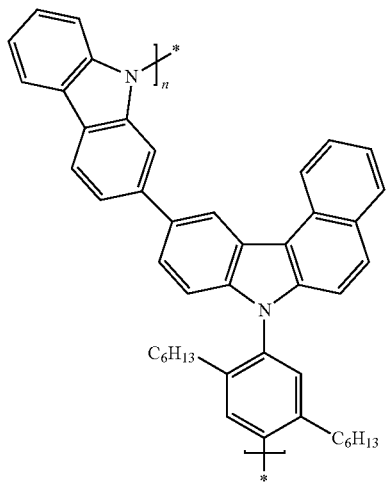
Polymer 3
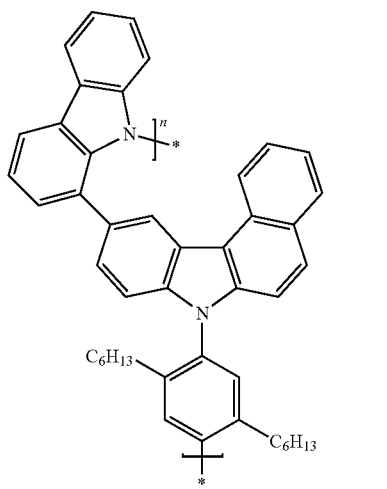
Polymer 4
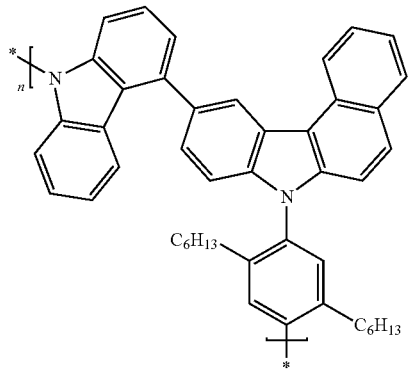
Polymer 5
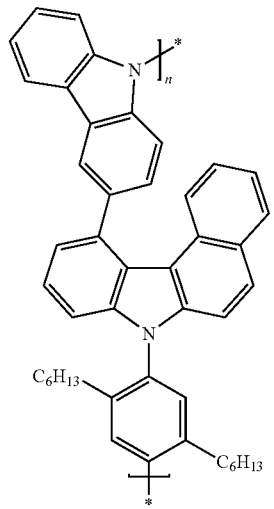
Polymer 6
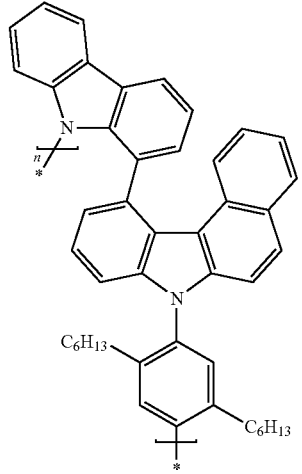
Polymer 7
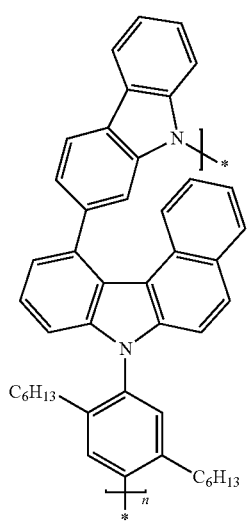

Polymer 8
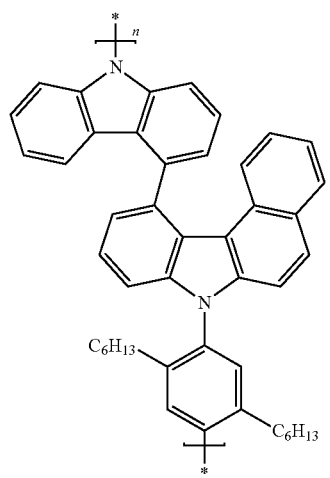
Polymer 9
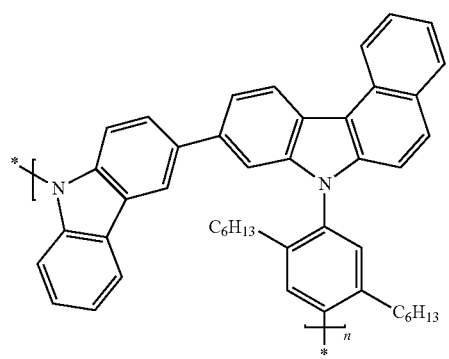
Polymer 10
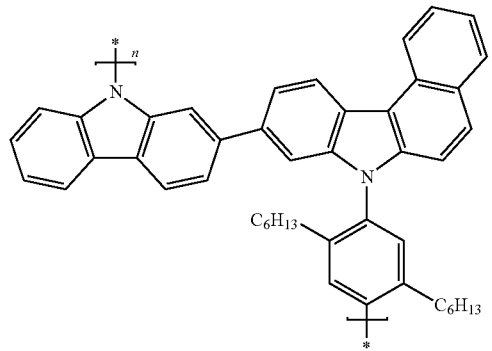
Polymer 11
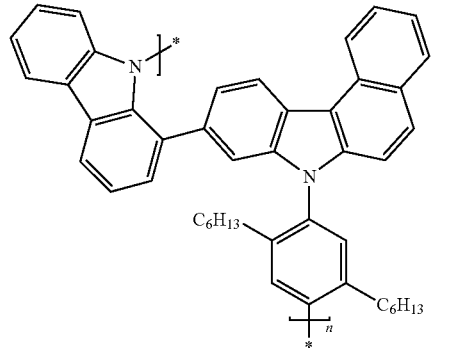
Polymer 12
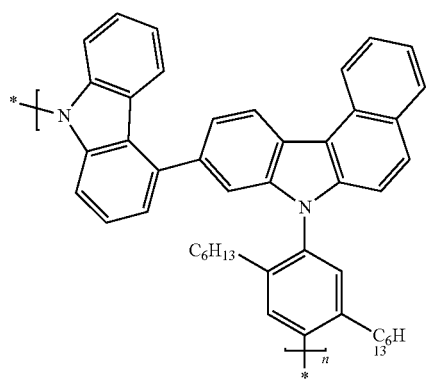
Polymer 13
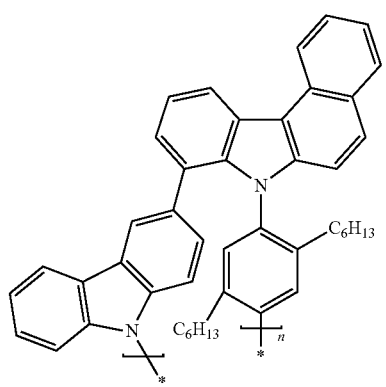
Polymer 14
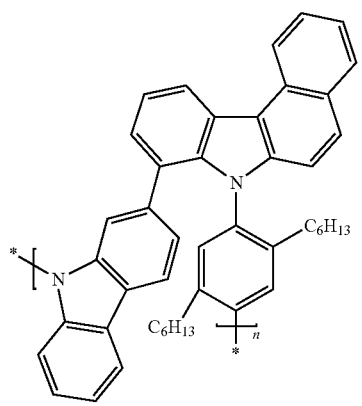
Polymer 15
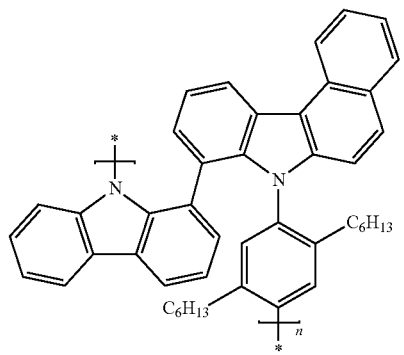

Polymer 16
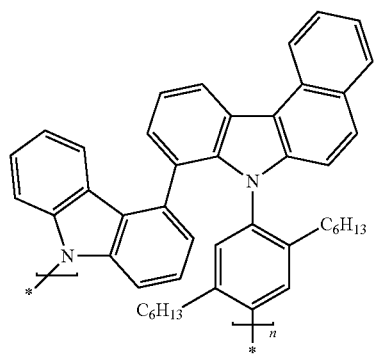
Polymer 17
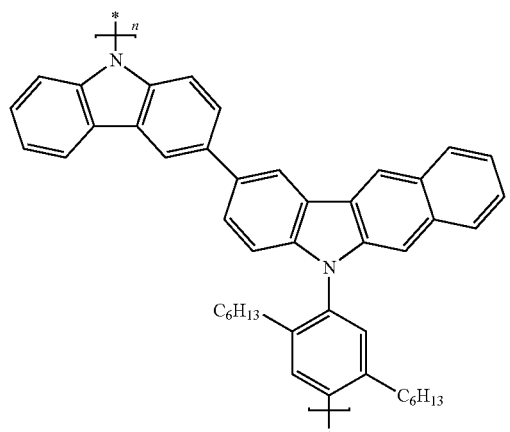
Polymer 18
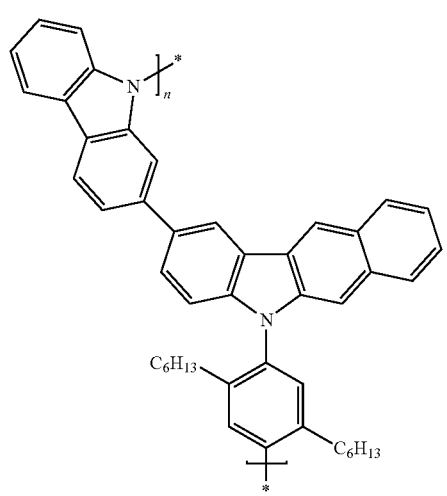
Polymer 19
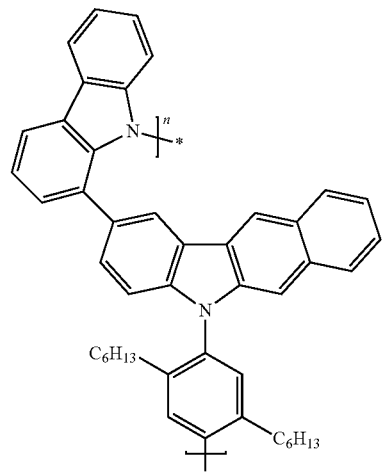
Polymer 20
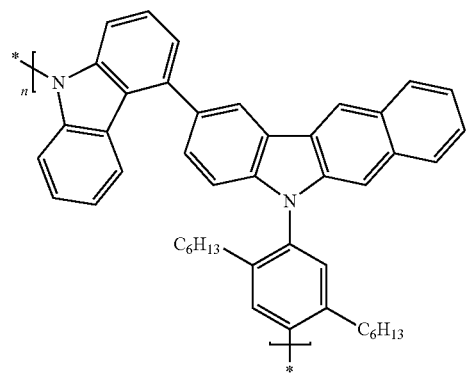
Polymer 21
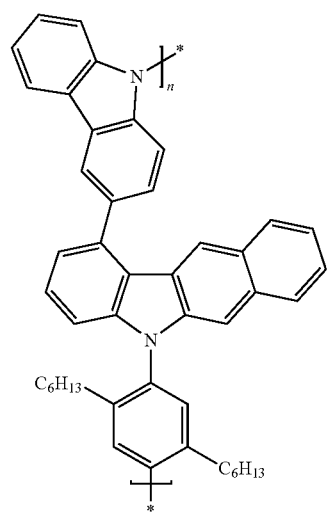

Polymer 22
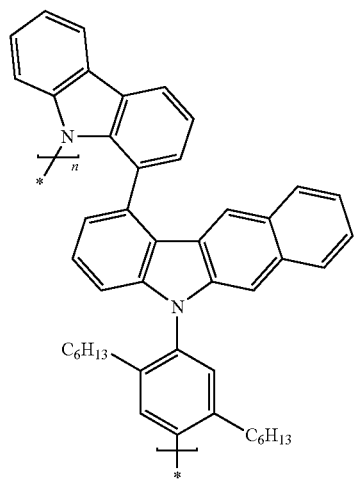
Polymer 23
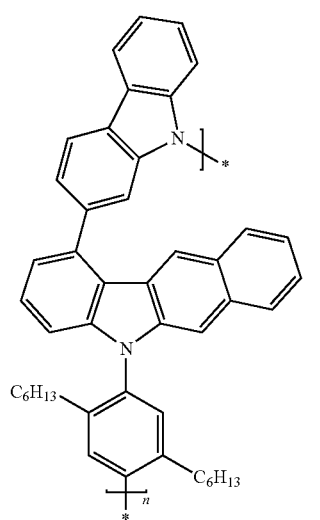
Polymer 24
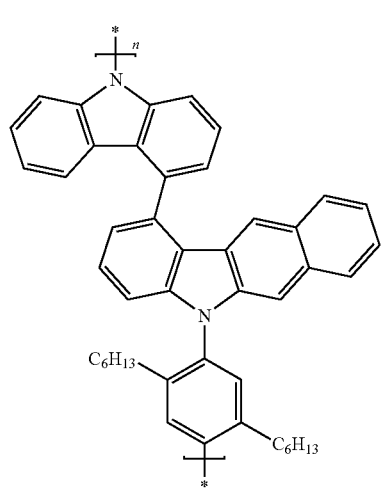
Polymer 25
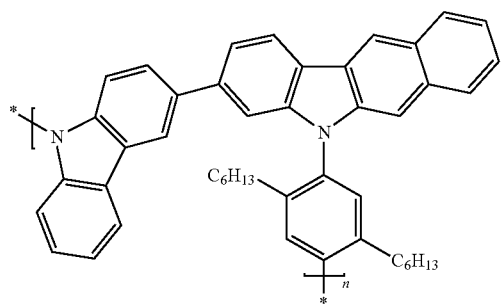
Polymer 26
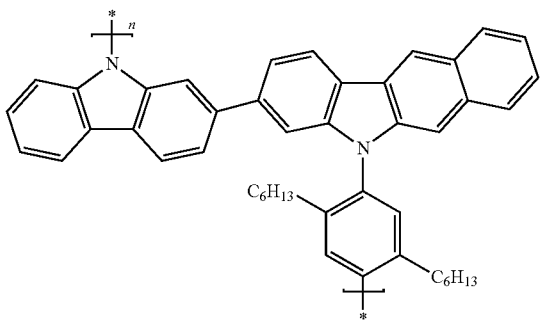
Polymer 27
Polymer 28
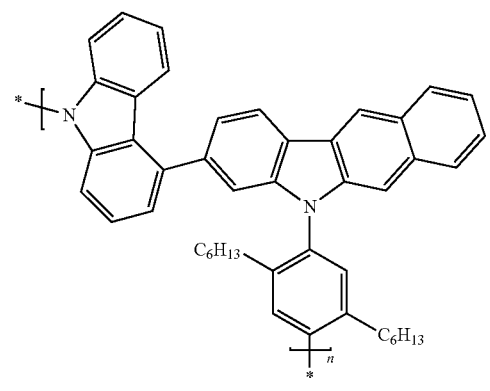

Polymer 29
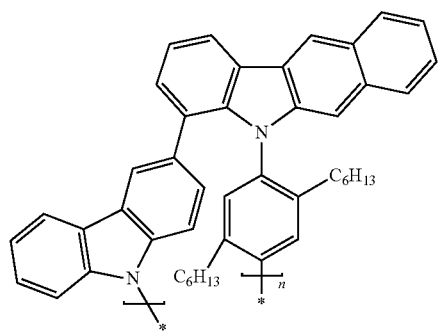
Polymer 30
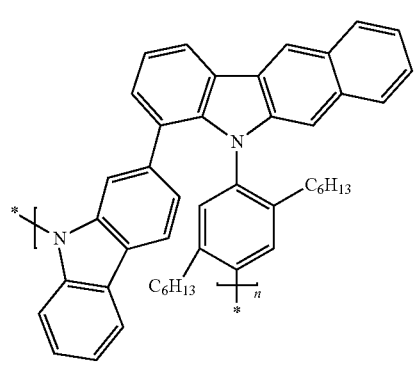
Polymer 31
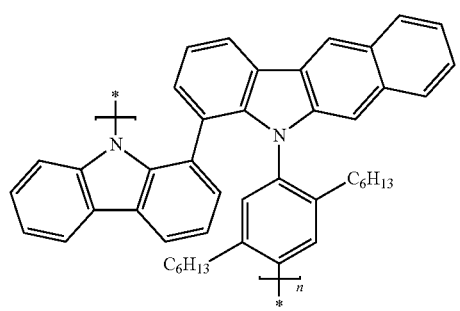
Polymer 32
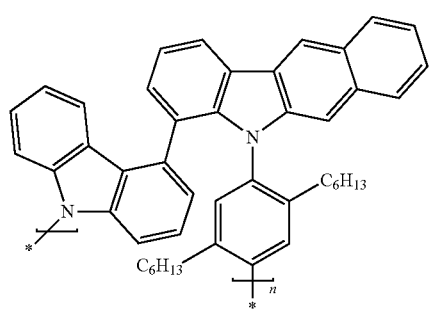
Polymer 33
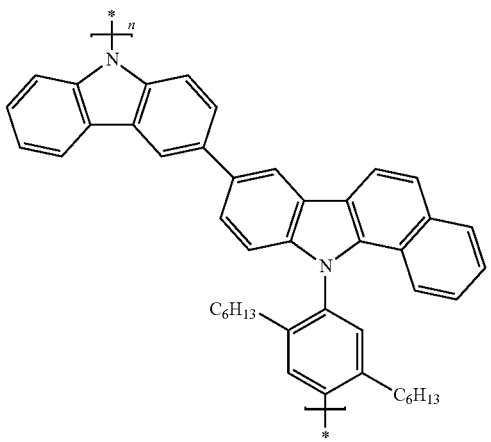
Polymer 34
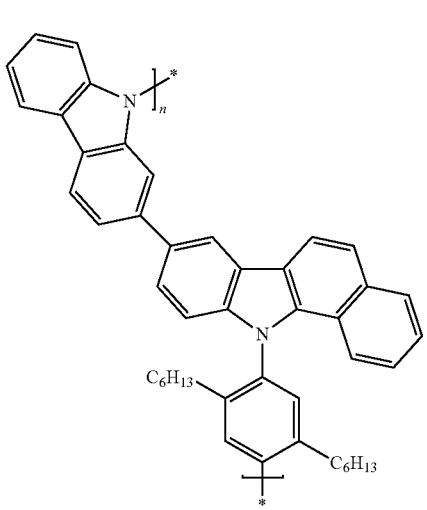
Polymer 35
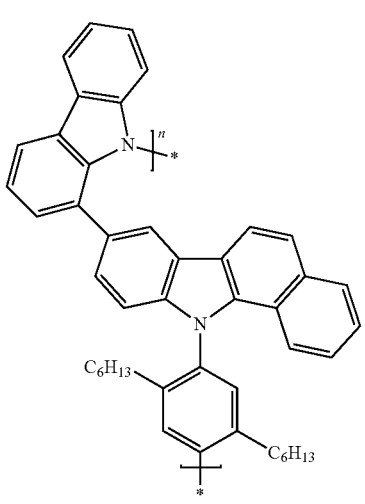

Polymer 36
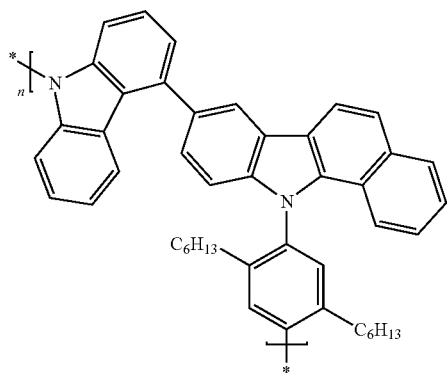
Polymer 37
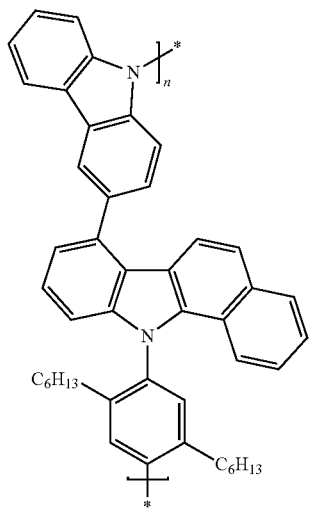
Polymer 38
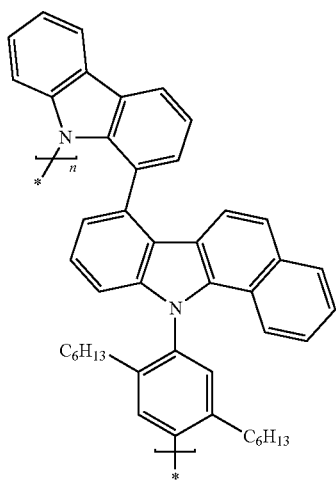
Polymer 39
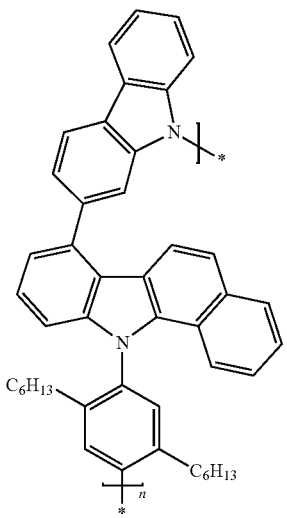
Polymer 40
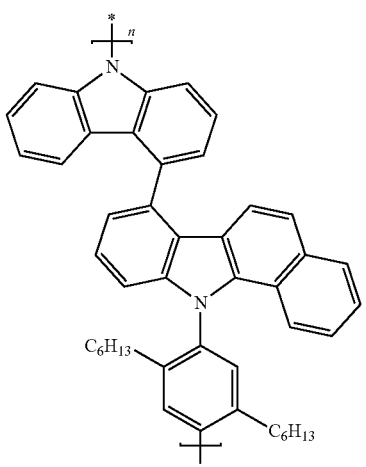
Polymer 41
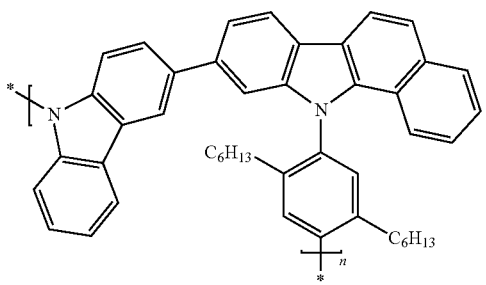
Polymer 42
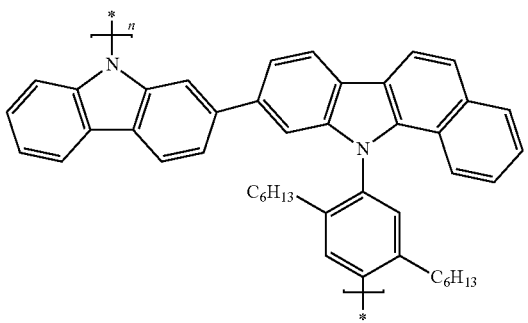

Polymer 43
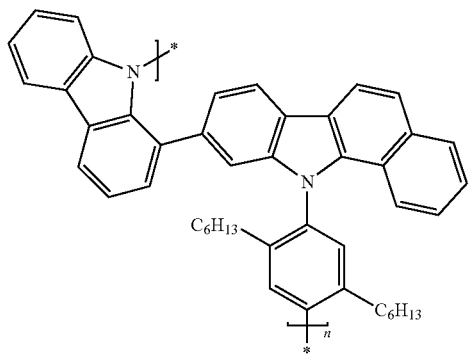
Polymer 44
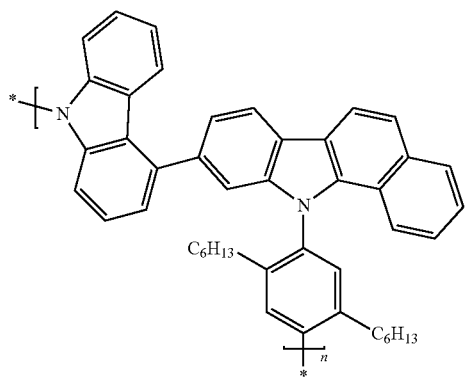
Polymer 45
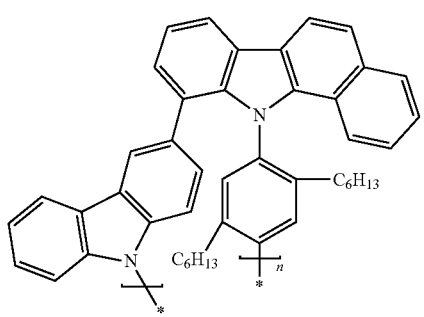
Polymer 46
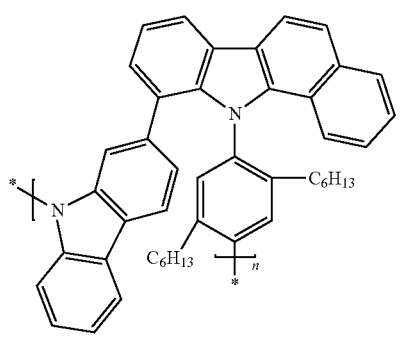
Polymer 47
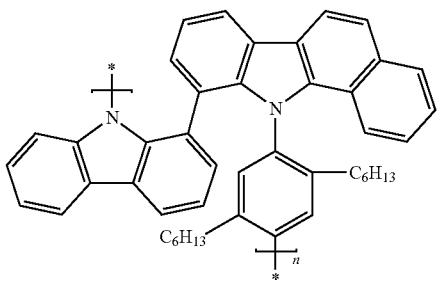
Polymer 48
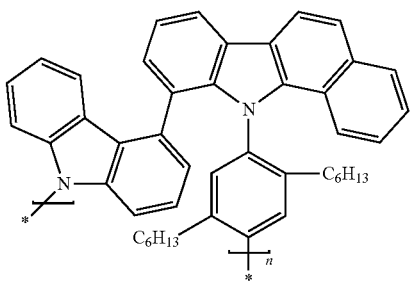
Polymer 49
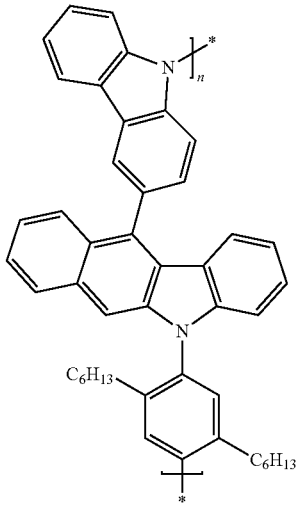
Polymer 50
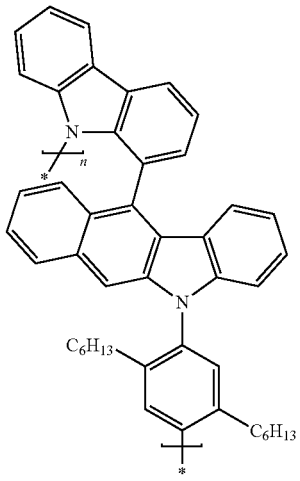

Polymer 51
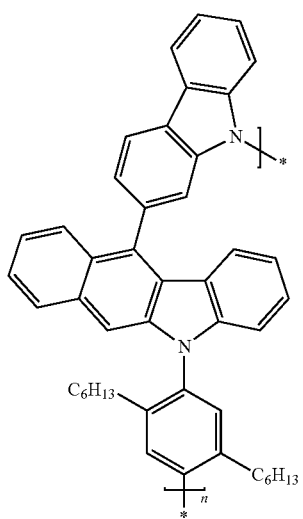
Polymer 52
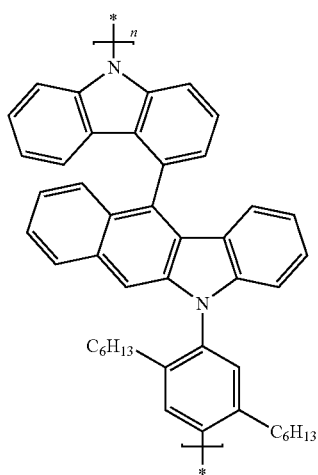
Polymer 53
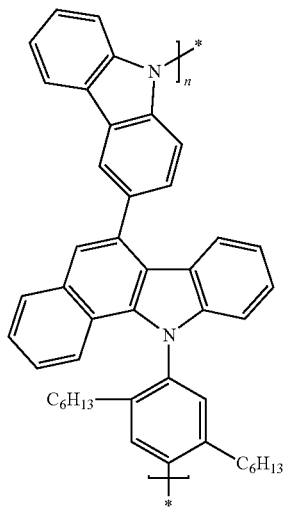
Polymer 54
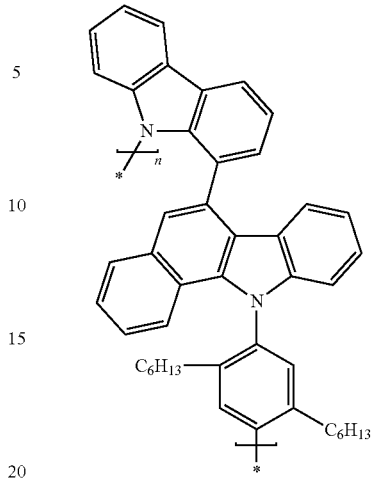
Polymer 55
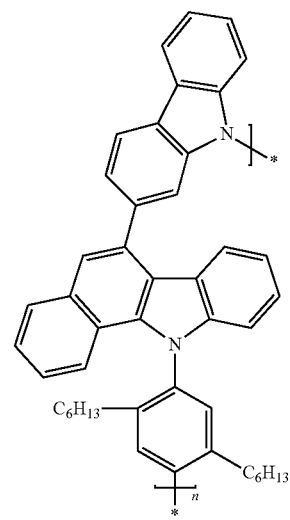
Polymer 56
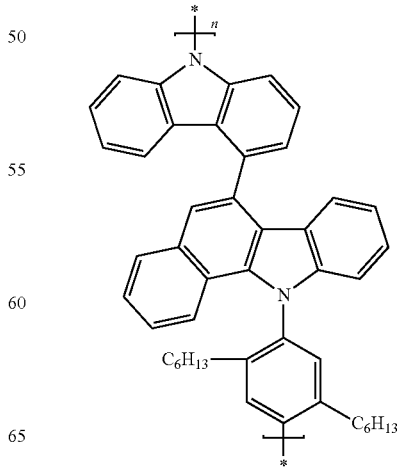

Polymer 57
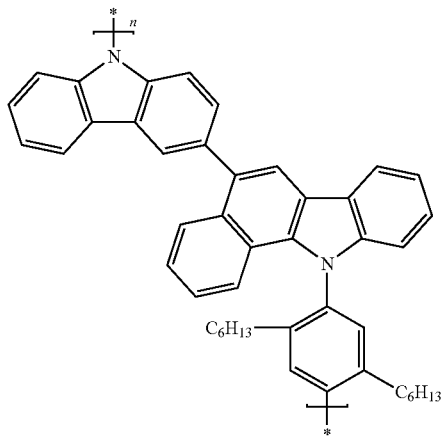
Polymer 58
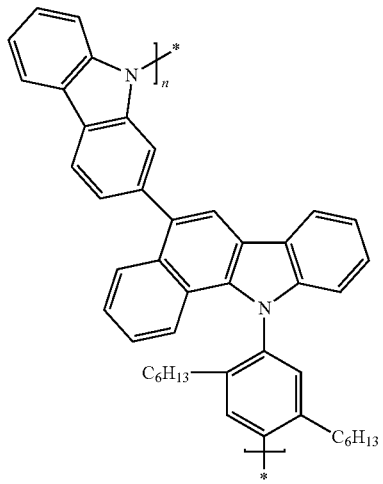
Polymer 59
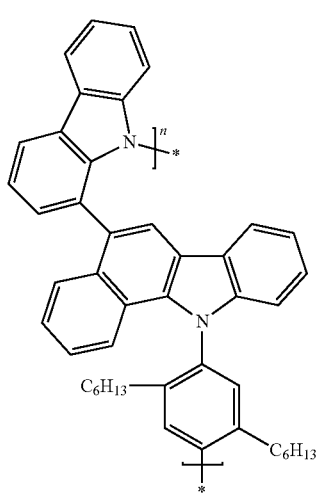
Polymer 60
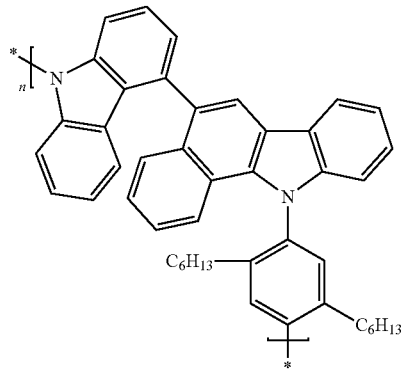
Polymer 61
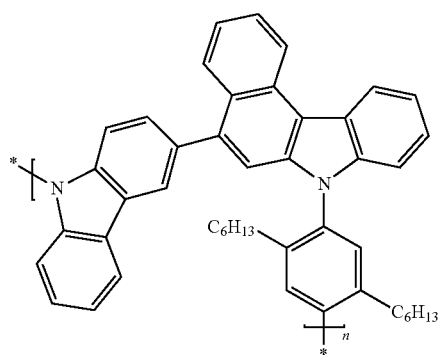
Polymer 62
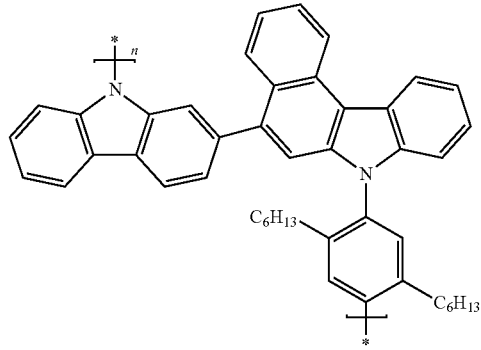
Polymer 63
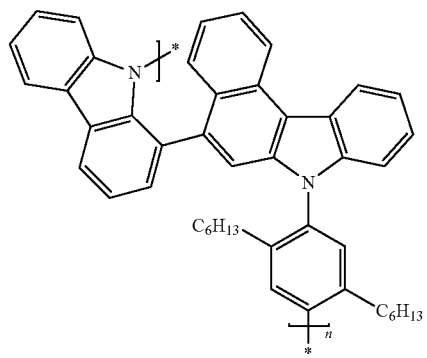

Polymer 64
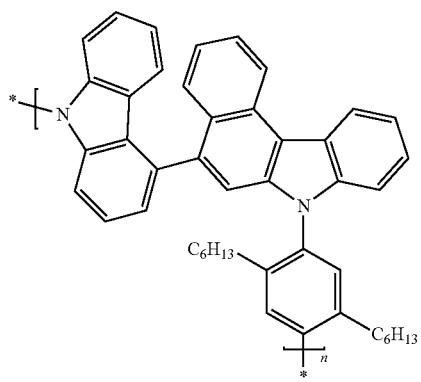
Polymer 68
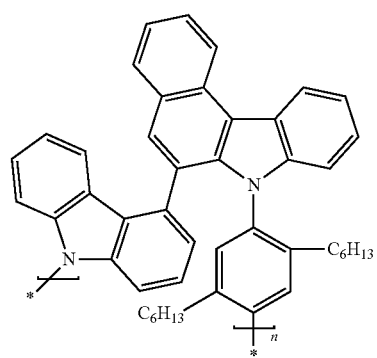
Polymer 65
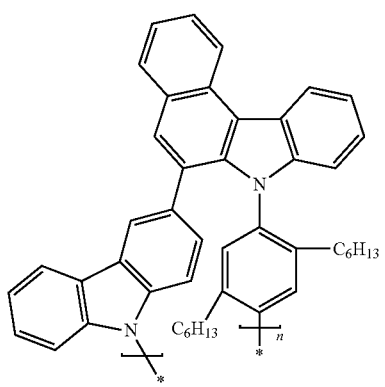
Polymer 69
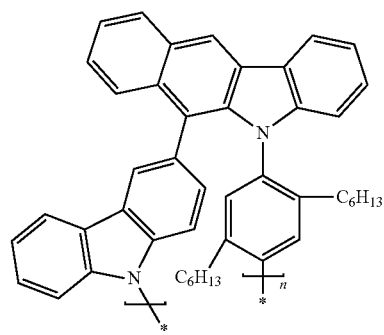
Polymer 66
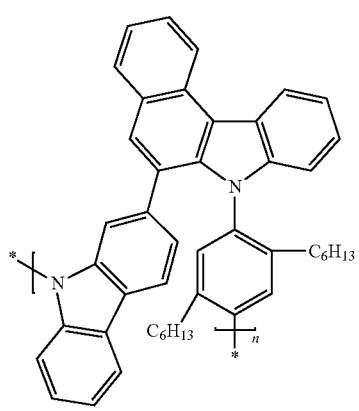
Polymer 70
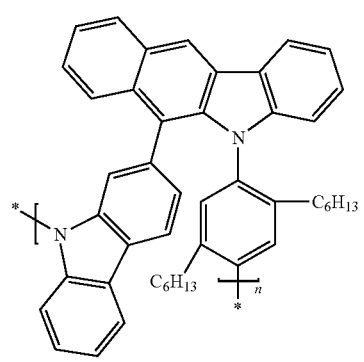
Polymer 67
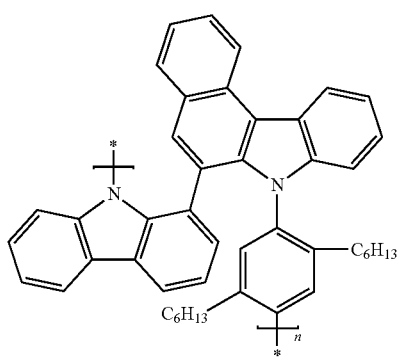
Polymer 71
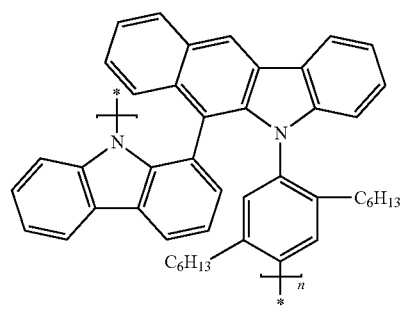

Polymer 72
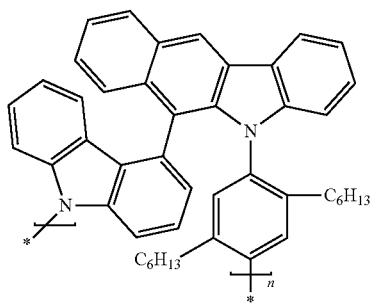
Polymer 73
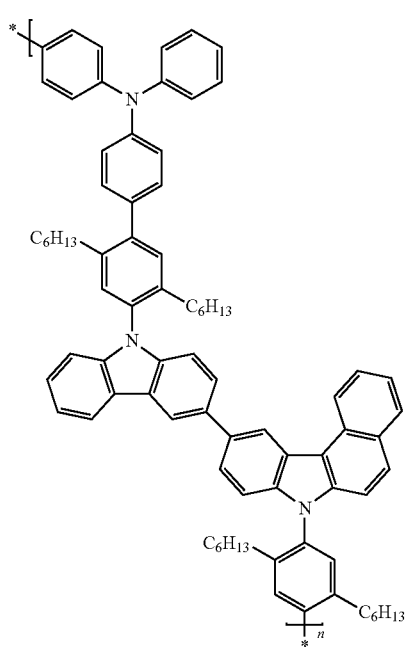
Polymer 74
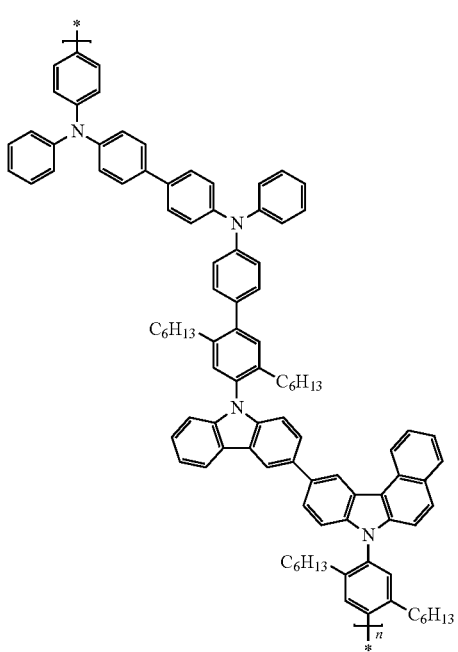
Polymer 75
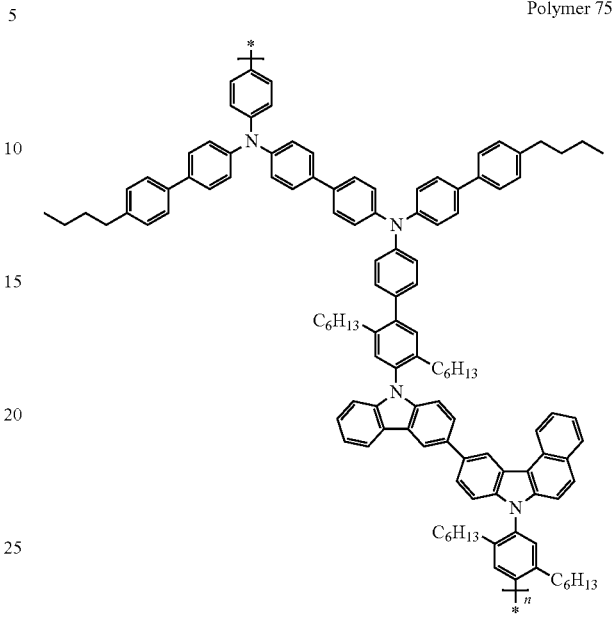
Polymer 76
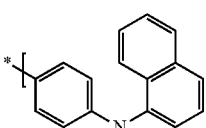

Polymer 77
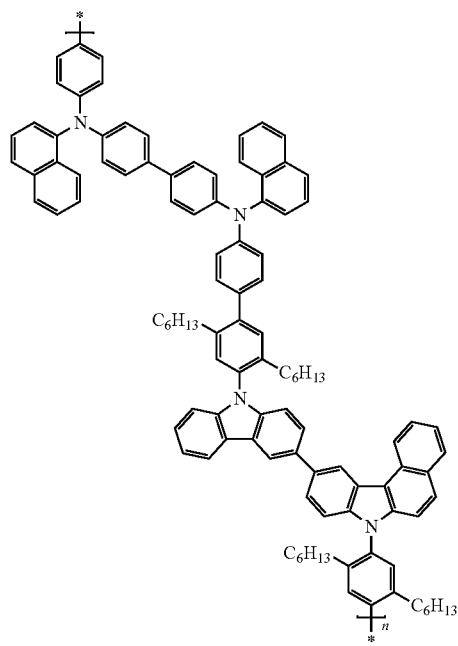
Polymer 78
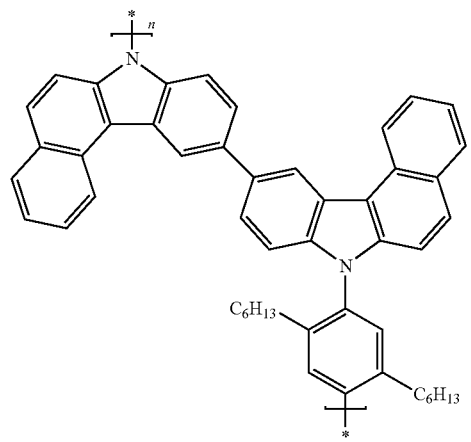
Polymer 79
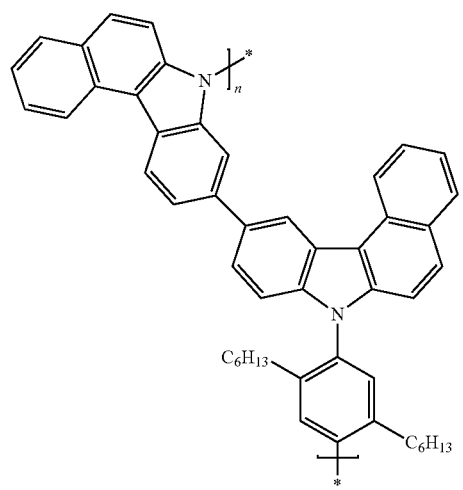
Polymer 80
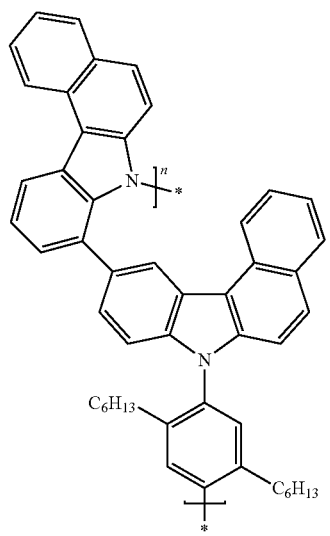
Polymer 81
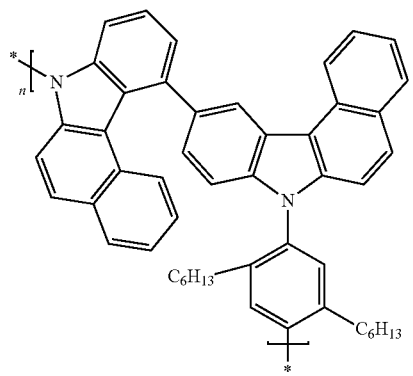
Polymer 82
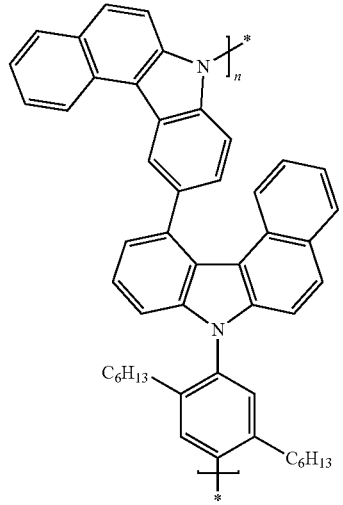

Polymer 83
Polymer 84
Polymer 85
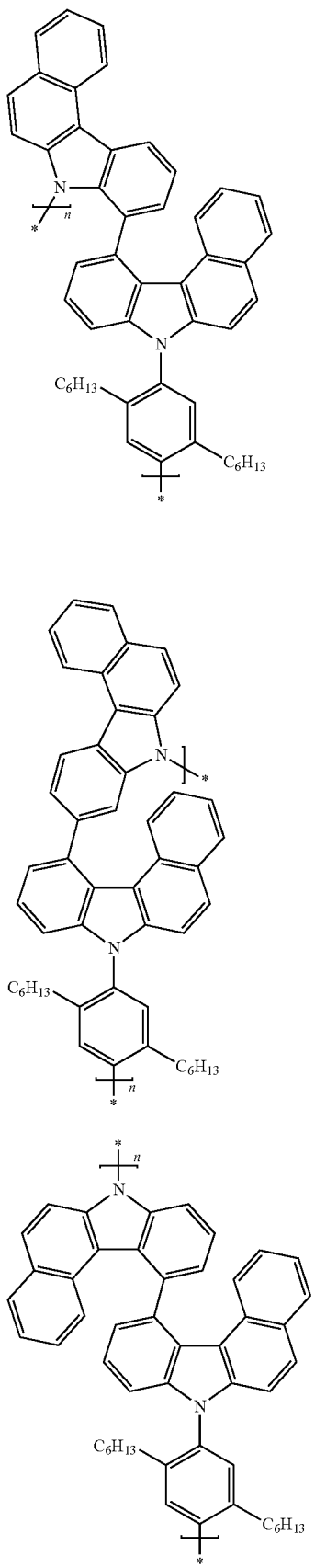
Polymer 86
Polymer 87
Polymer 88
Polymer 89
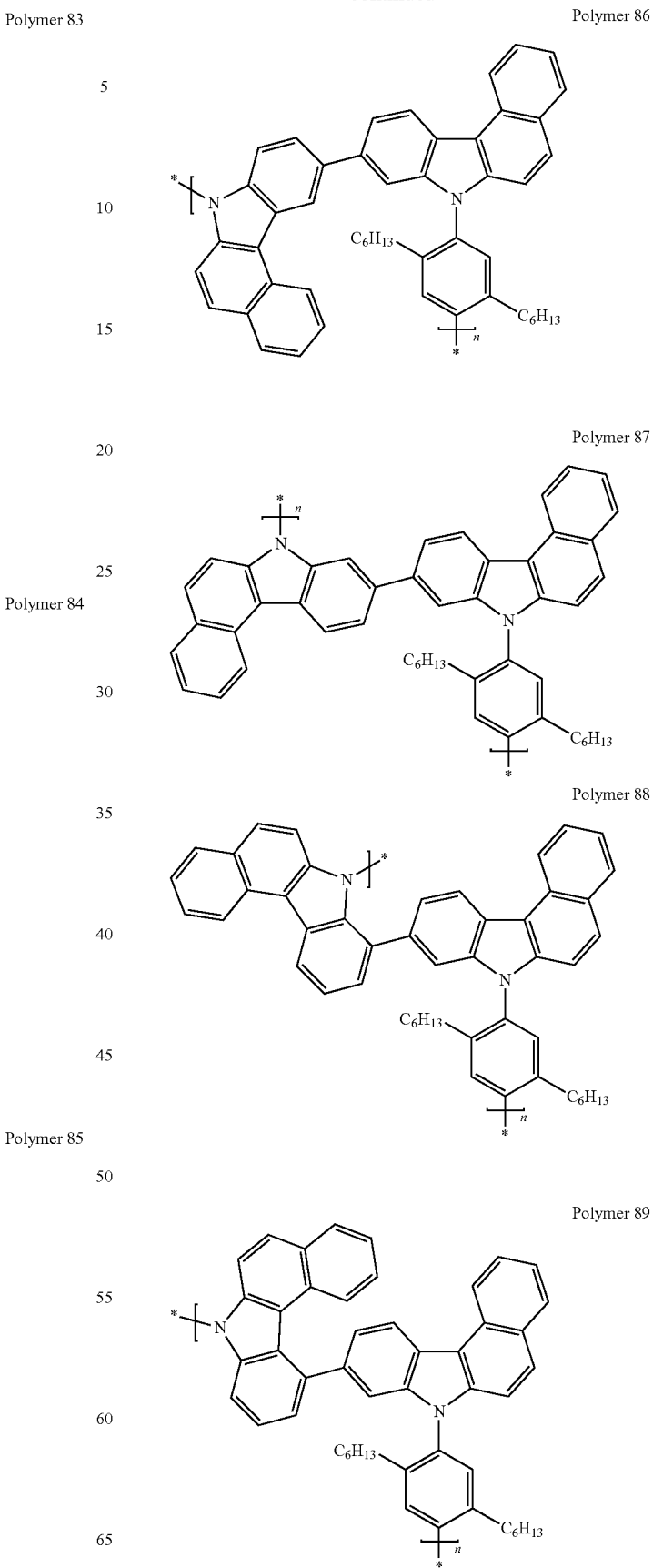

Polymer 90
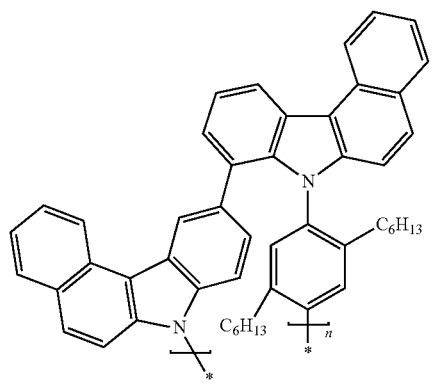
Polymer 91
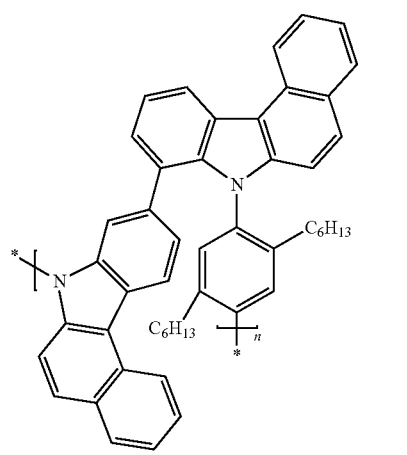
Polymer 92
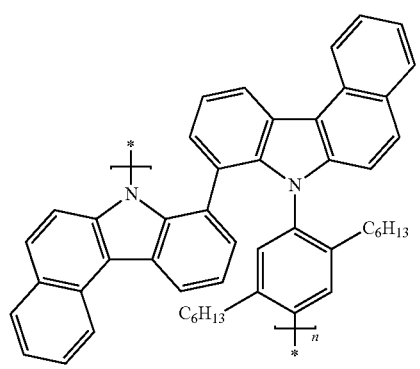
Polymer 93
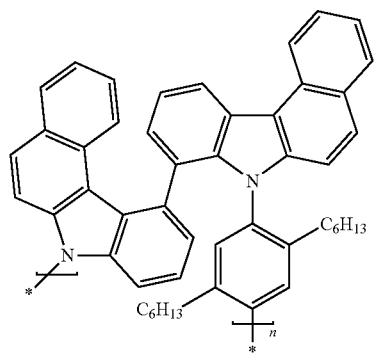
Polymer 94
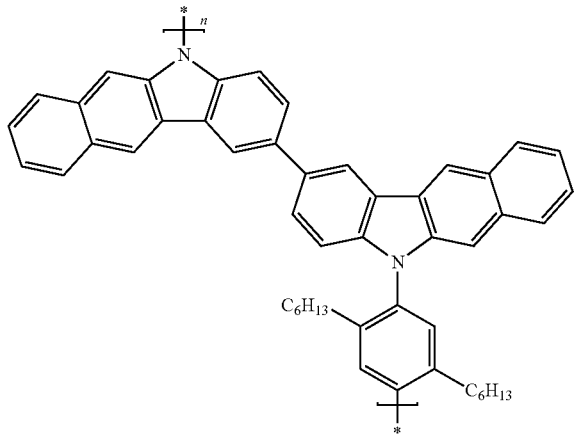
Polymer 95
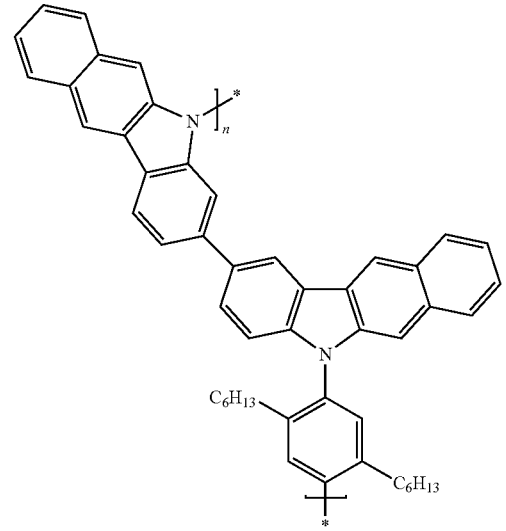
Polymer 96
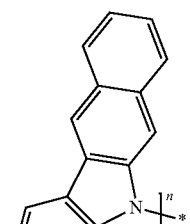
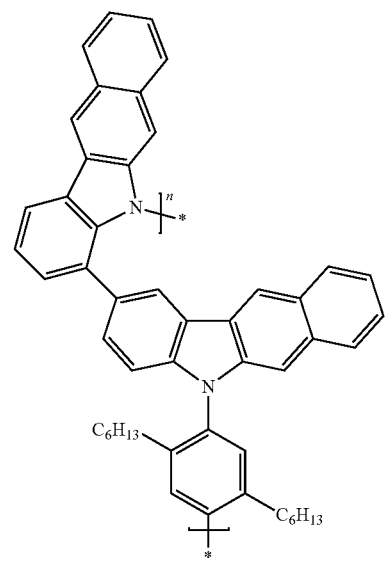

Polymer 97
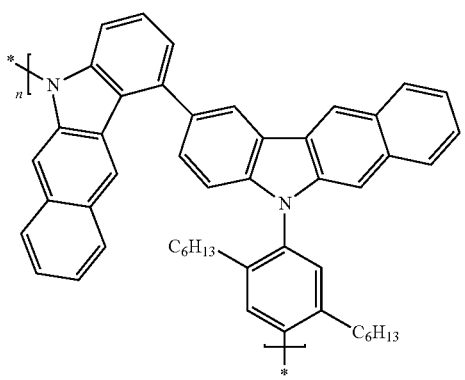
Polymer 98
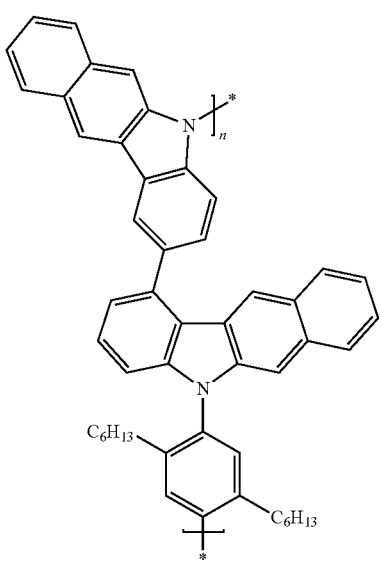
Polymer 99
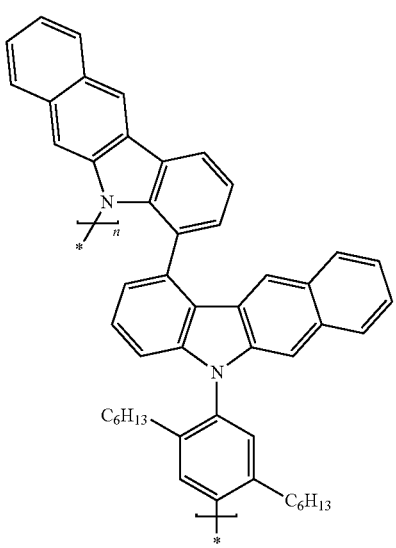
Polymer 100
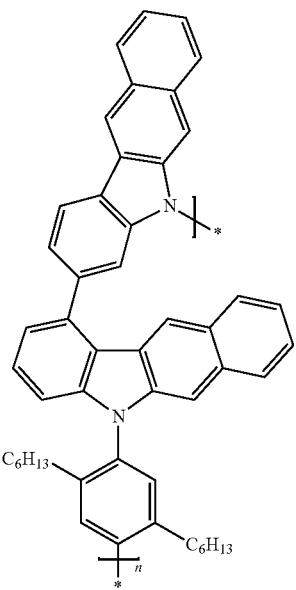
Polymer 101
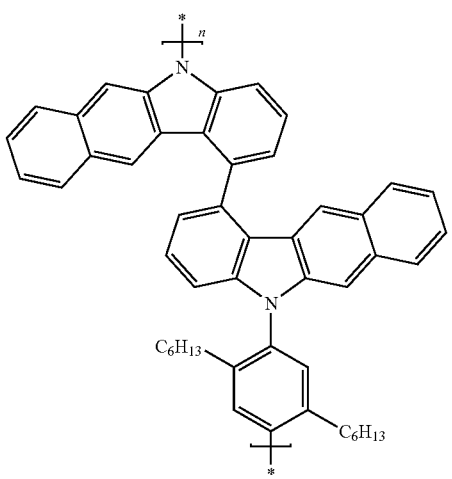
Polymer 102
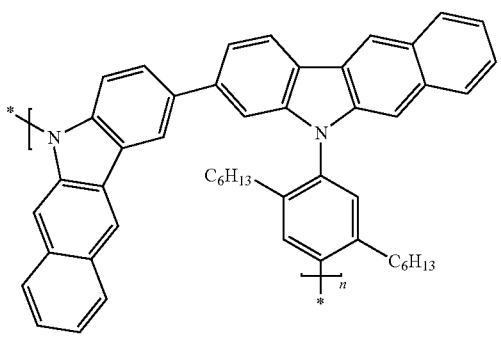

-continued
Polymer 103
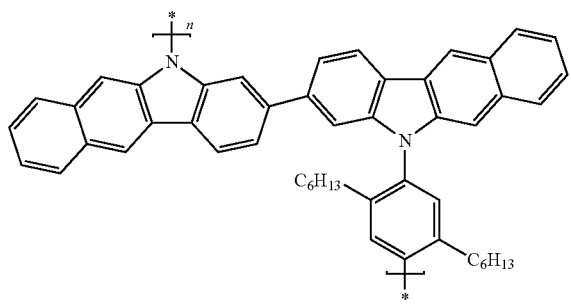
Polymer 104
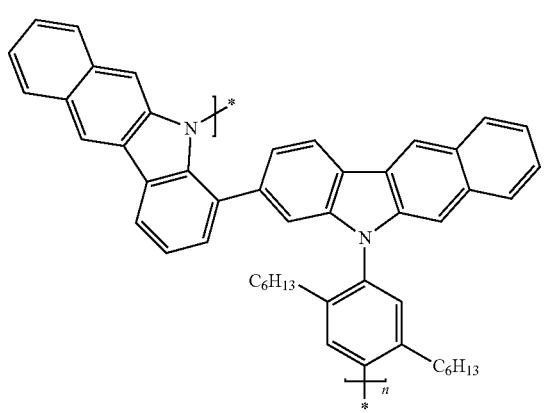
Polymer 105
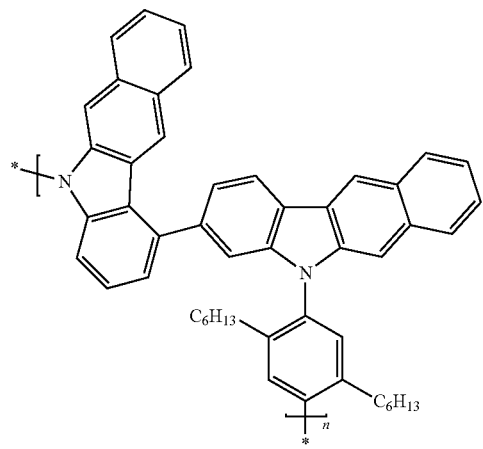
Polymer 106
-continued
Polymer 107
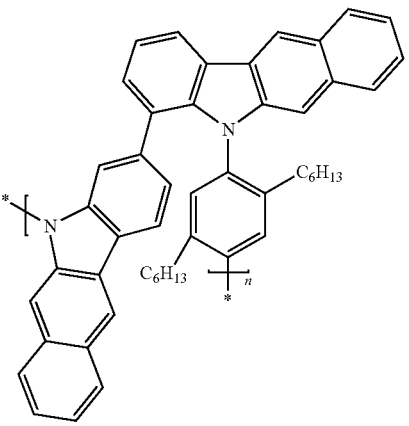
Polymer 108
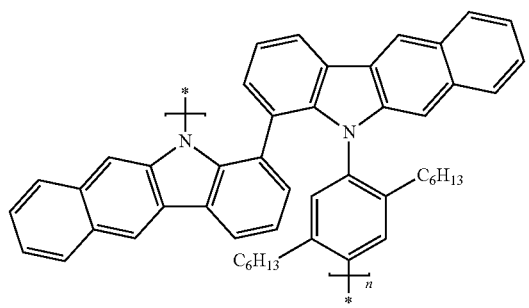
Polymer 109
Polymer 110
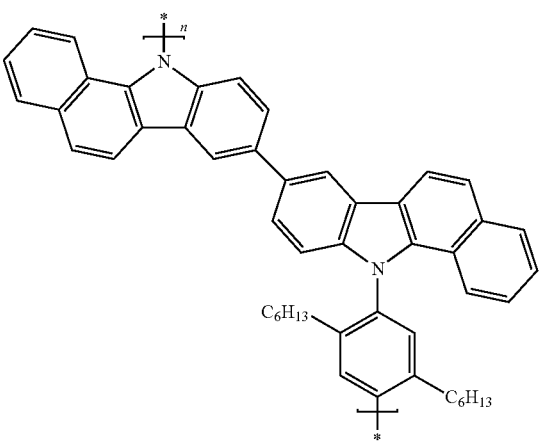

Polymer 111
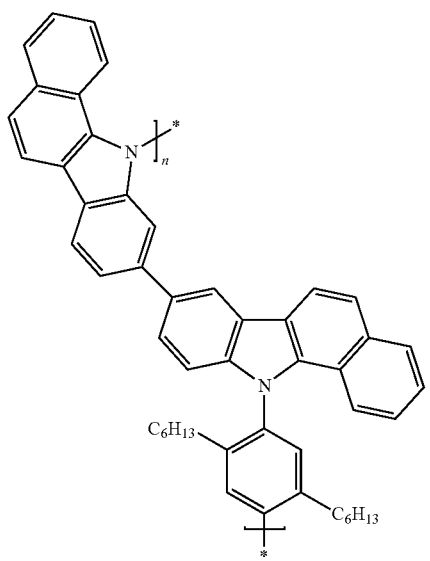
Polymer 112
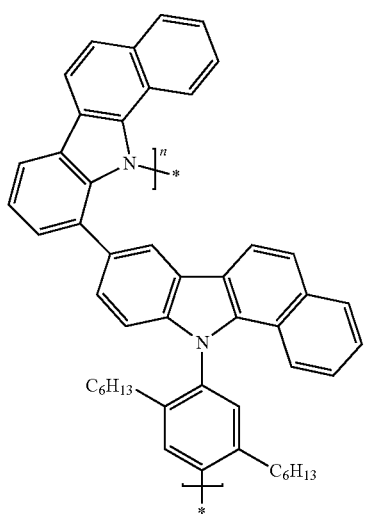
Polymer 113
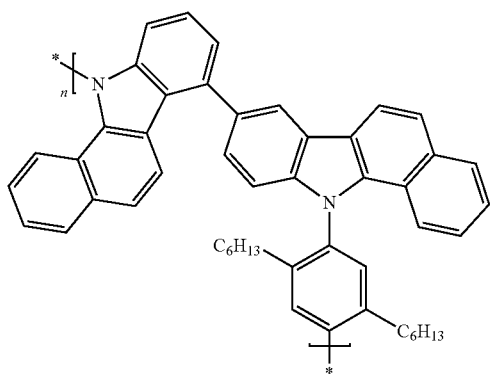
Polymer 114
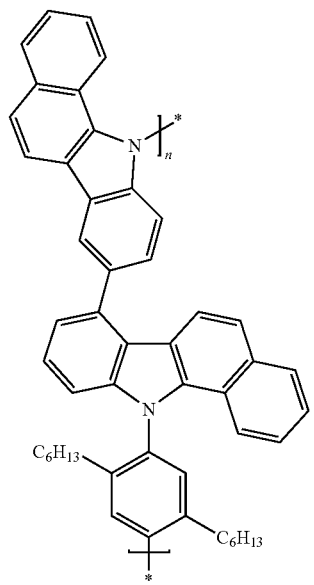
Polymer 115
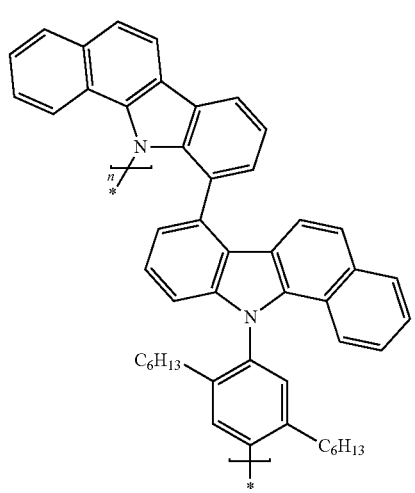
Polymer 116
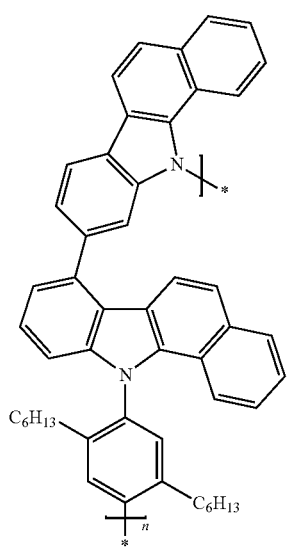

Polymer 117
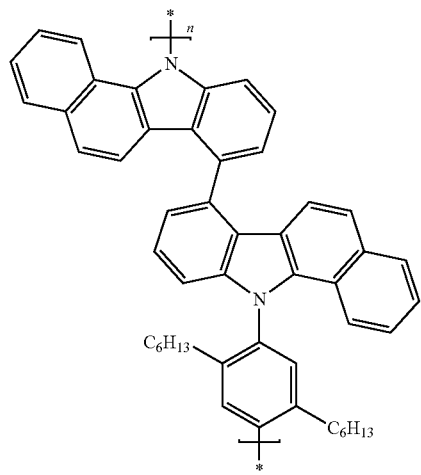
Polymer 118
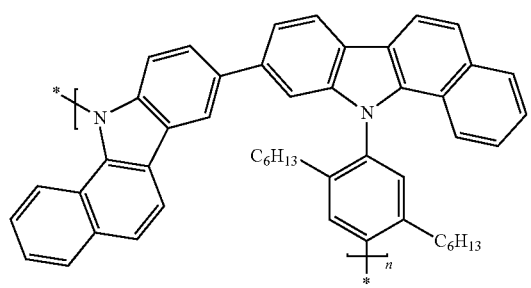
Polymer 119
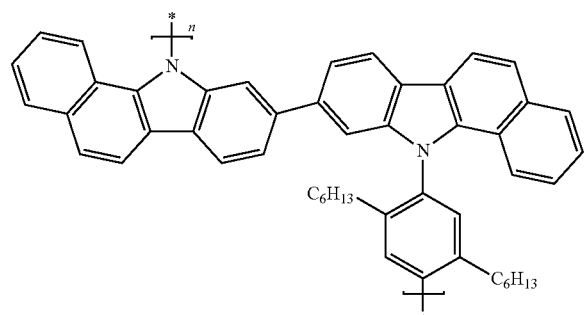
Polymer 120
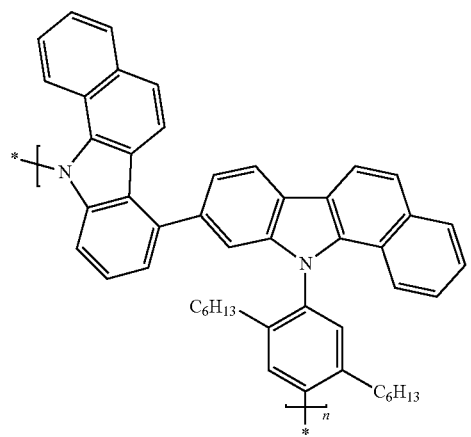
Polymer 121
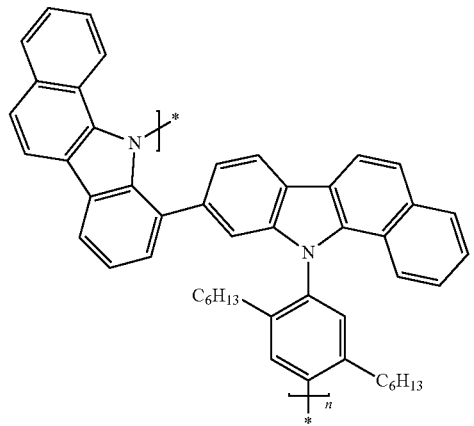
Polymer 122
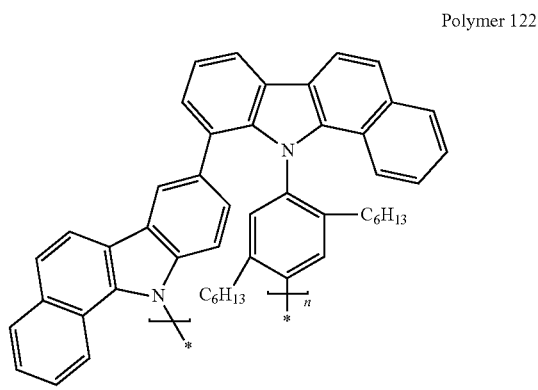
Polymer 123
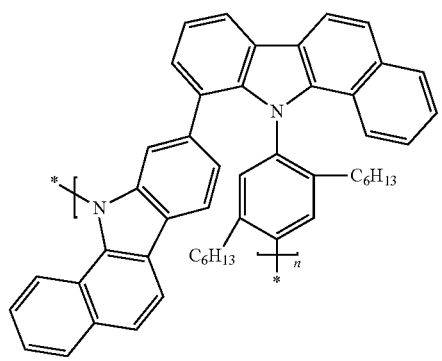
Polymer 124
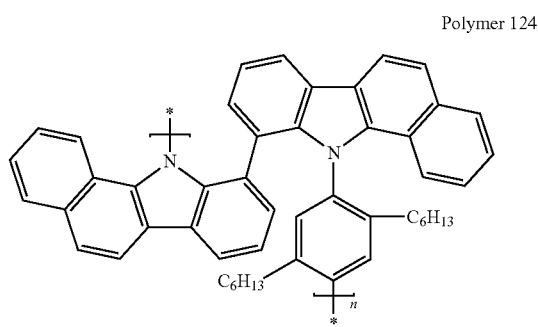

-continued
Polymer 125
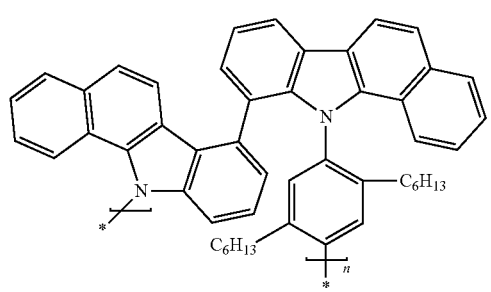
Polymer 126
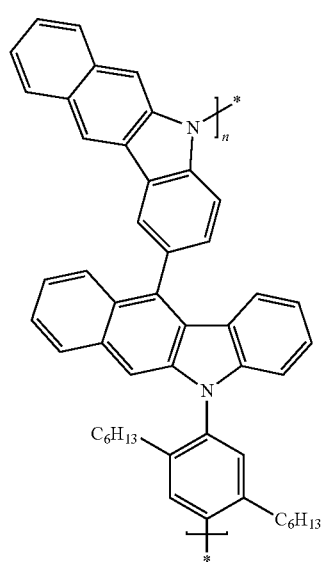
Polymer 127
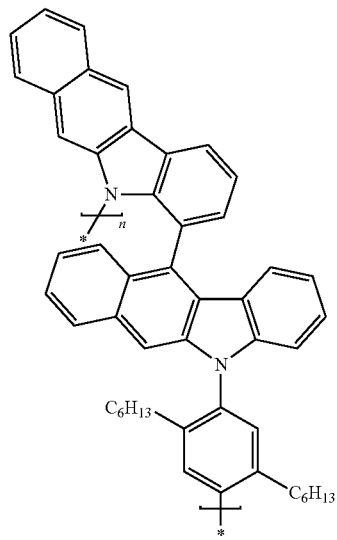
-continued
Polymer 128
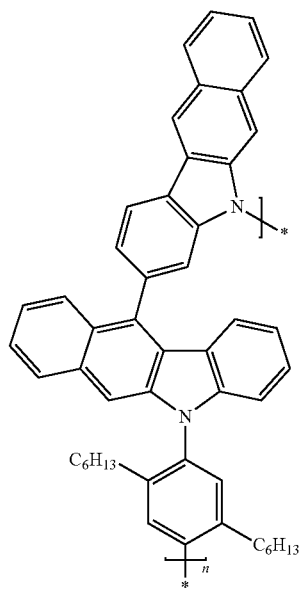
Polymer 129
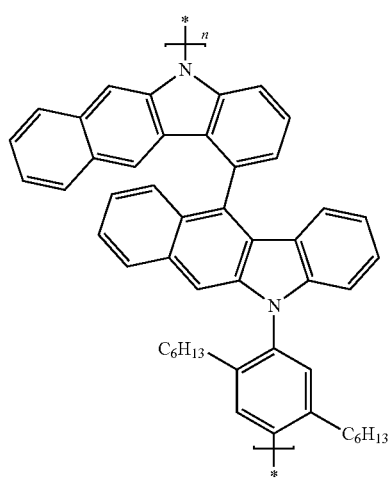
Polymer 130
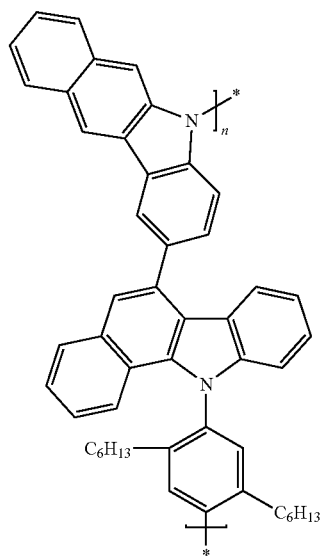

-continued
Polymer 131
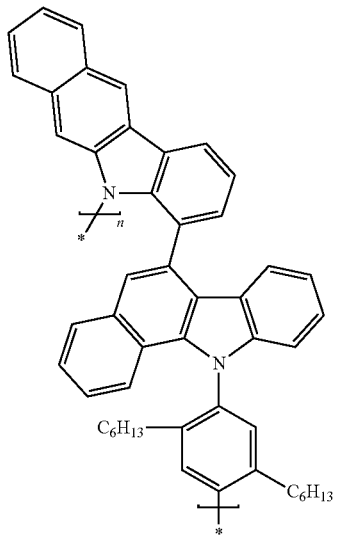
Polymer 132
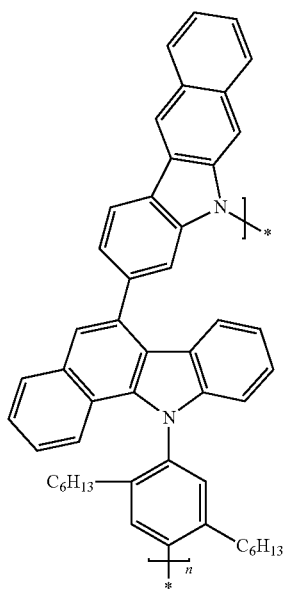
Polymer 133
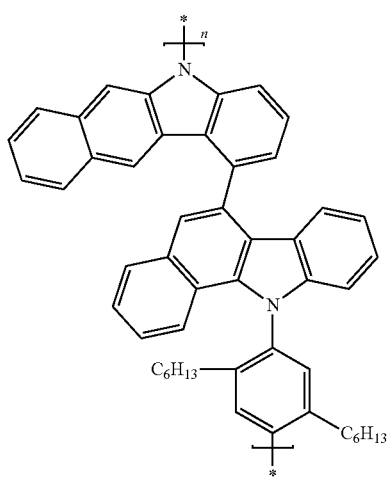
Polymer 134
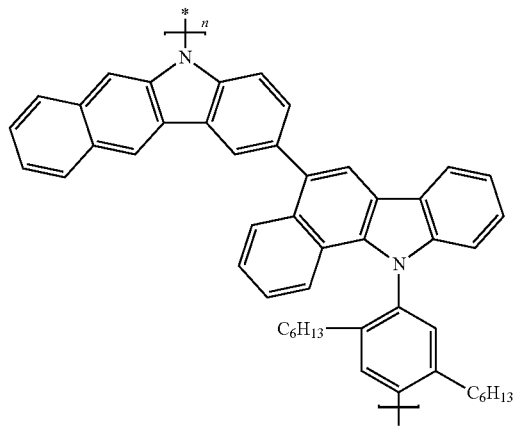
Polymer 135
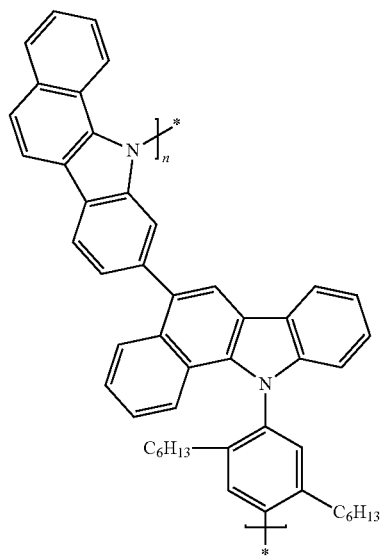
Polymer 136
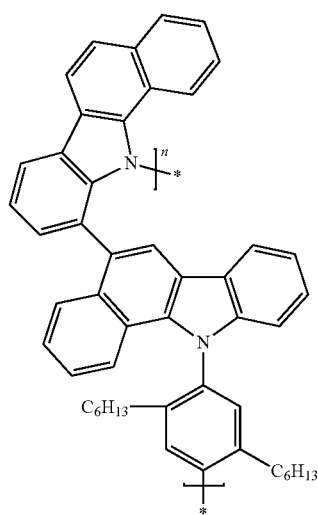

Polymer 137
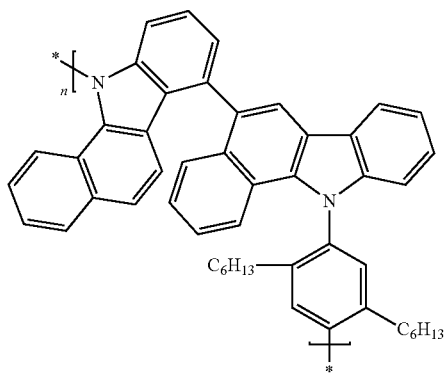
Polymer 138
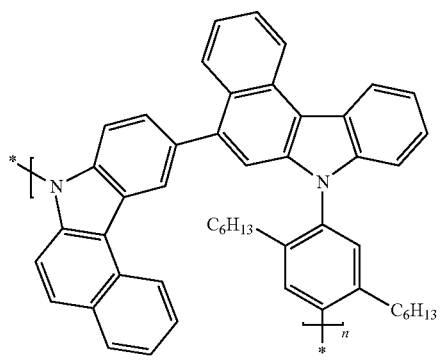
Polymer 139
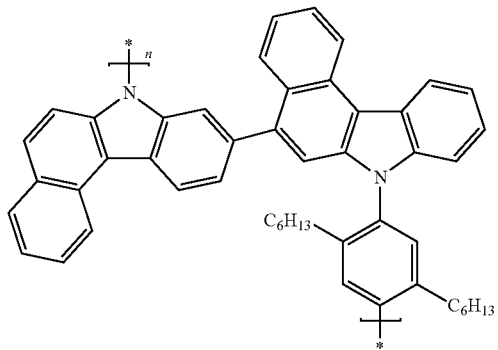
Polymer 140
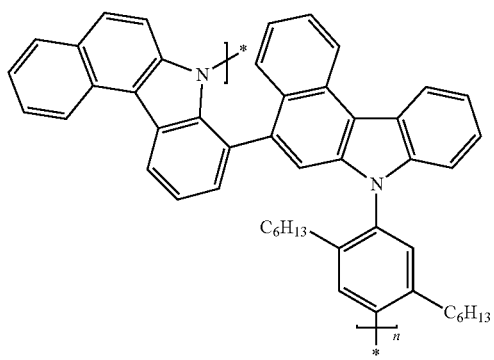
Polymer 141
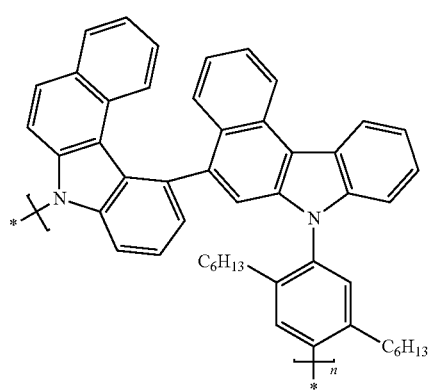
Polymer 142
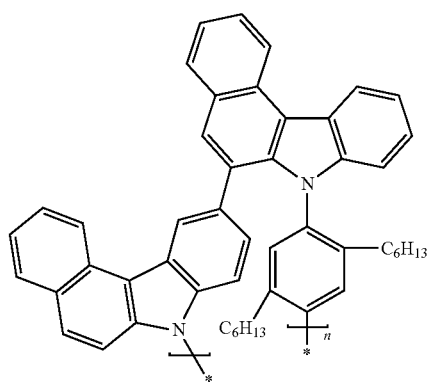
Polymer 143
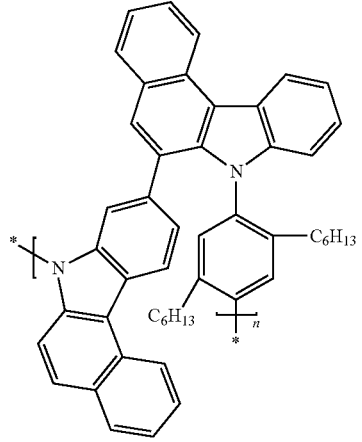
Polymer 144
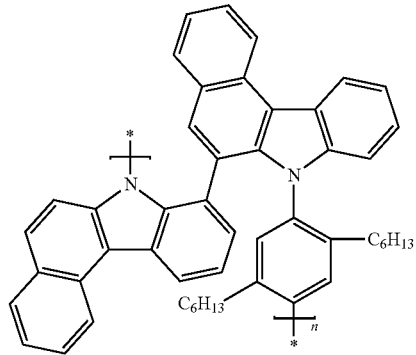

Polymer 145
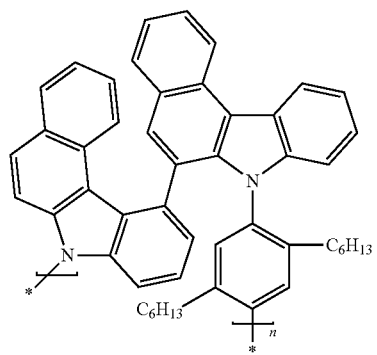
Polymer 149
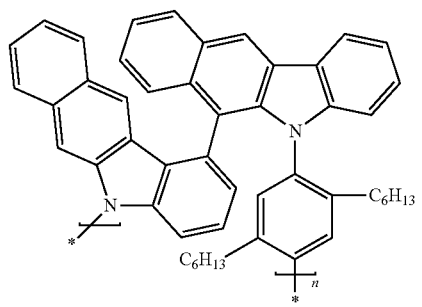
Polymer 146
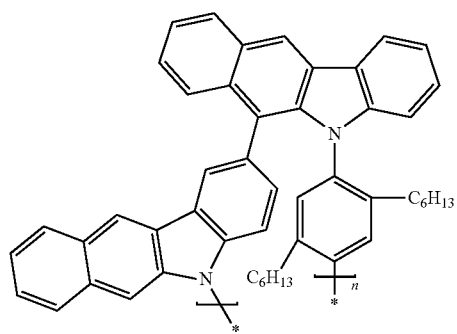
Polymer 150
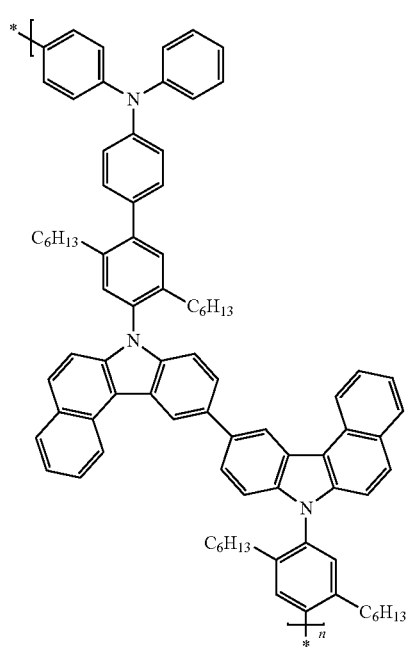
Polymer 147
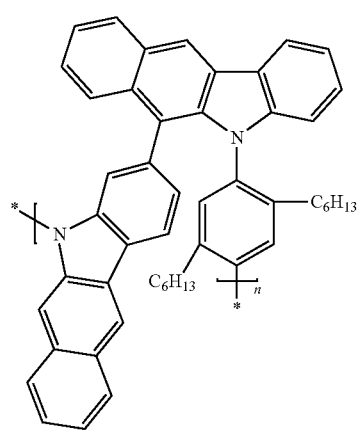
Polymer 151
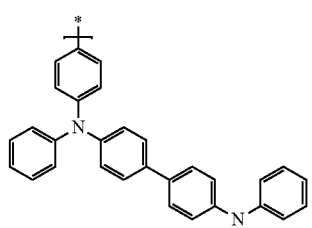
Polymer 148
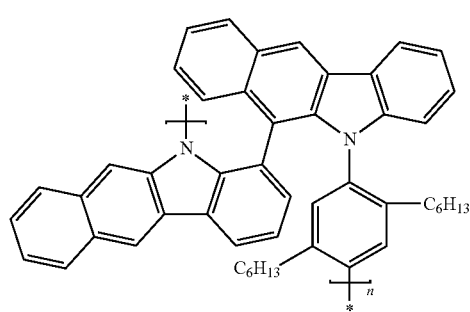
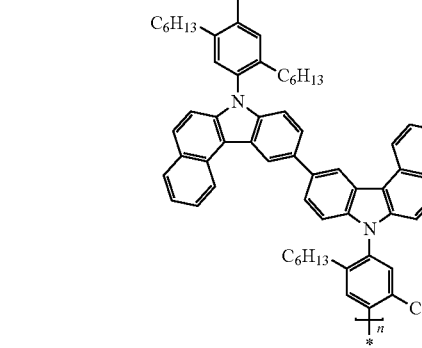

Polymer 152
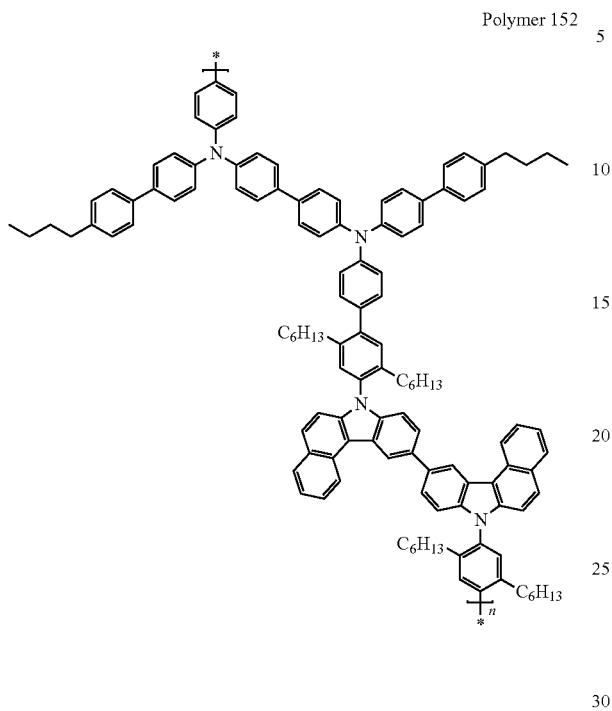
Polymer 153
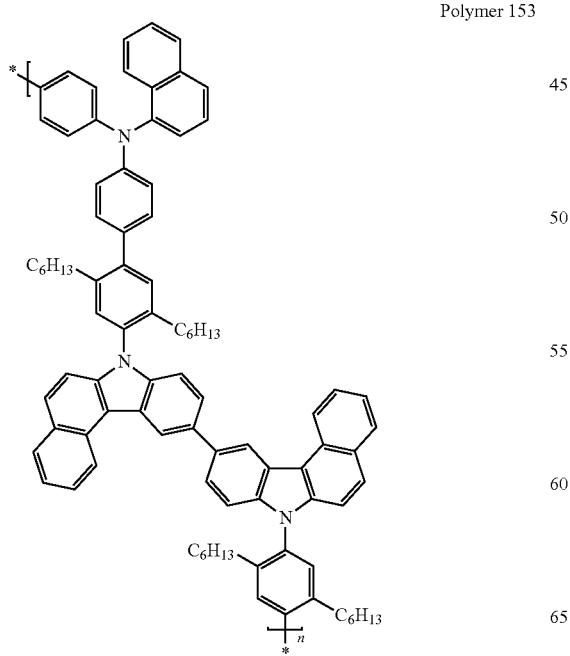
Polymer 154
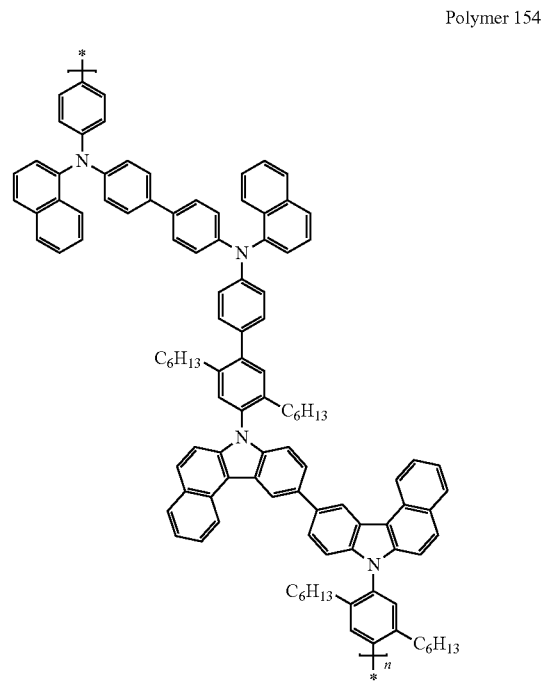
Polymer 155
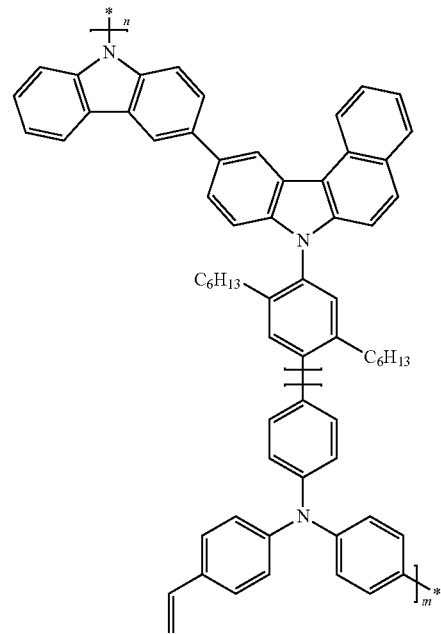

Polymer 156
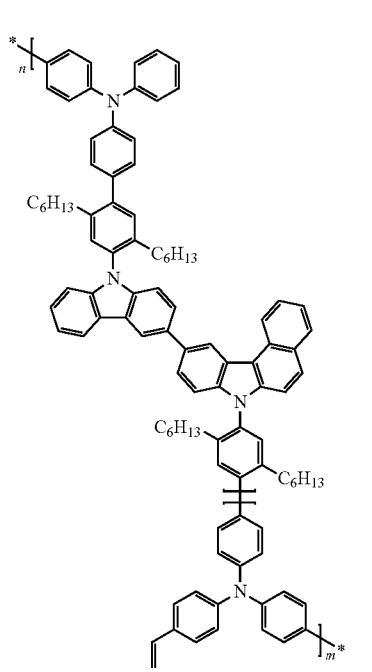
Polymer 157
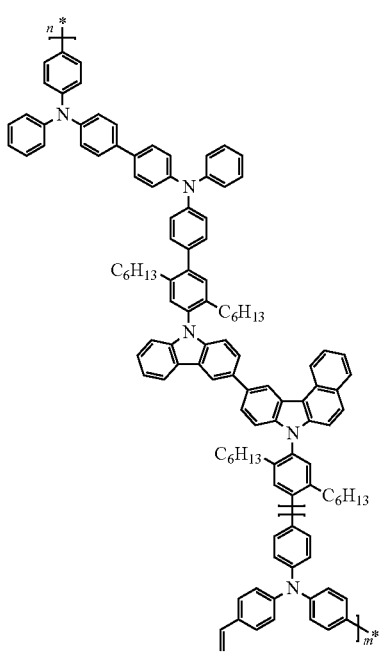
Polymer 158
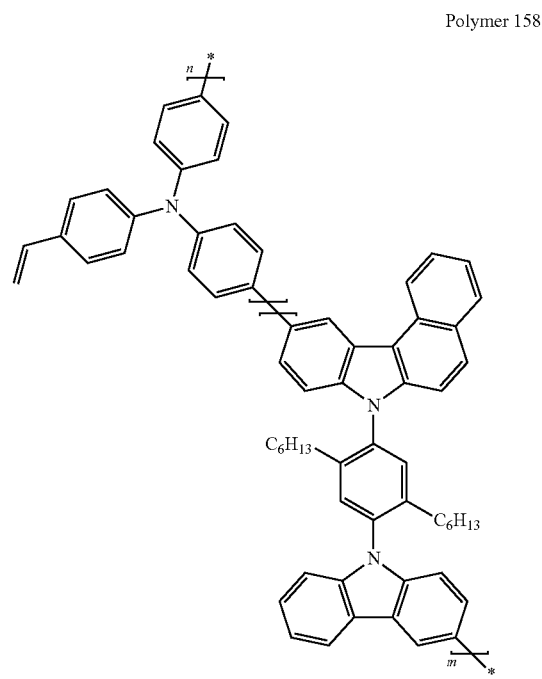
Polymer 159
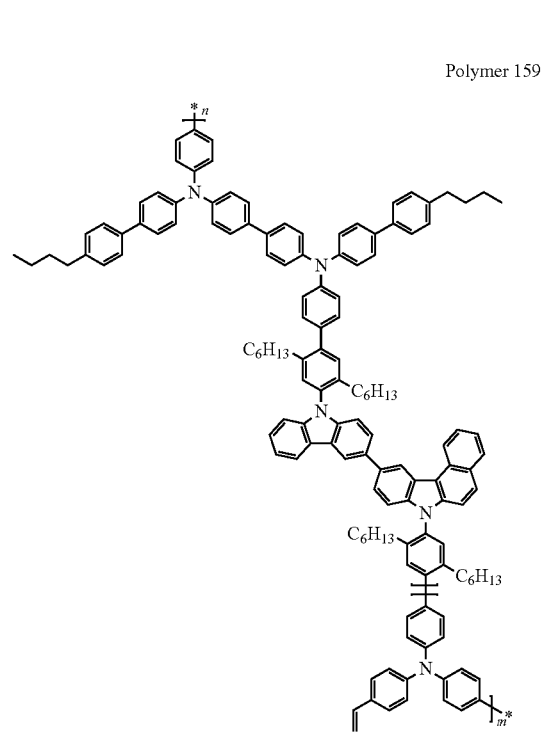

-continued

Polymer 160

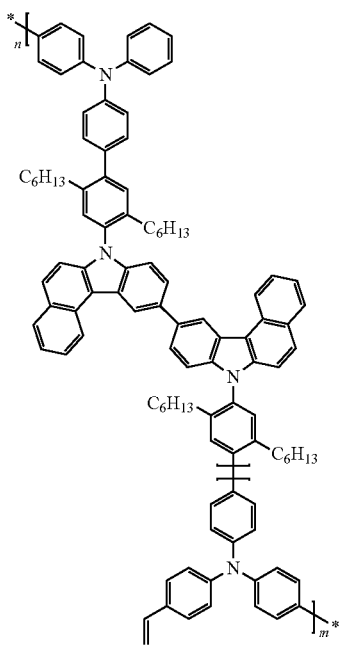

It should be pointed out that when two different reactive groups are linked to each other, a head-to-head link may occur, and a head-to-tail link may also occur, and the active group of a monomer may be designed as needed, so examples are not all listed above.

The present disclosure further relates to a synthesis method of the polymer of the general formula (I), or (VI) or (V), wherein a reaction is carried out using raw materials including an active group. Such active raw materials include the structural unit of the foregoing general formula and at least one leaving group, for example: Cl, Br, I, o-tosylate, o-triflate, o-mesylate, o-nonaflate, NH, $SiMe_{3-n}F_n$, $O-SO_2R^{11}$, $B(OR^{11})_2$, $-CR^{11}=C(R^{11})_2$, $-C\equiv CH$ and $Sn(R^{11})_3$, particularly Br, I, and $B(OR^{11})_2$. Suitable reactions for the formation of a C—C link are well known to those skilled in the art and are described in literature, and the polymerization method is selected from the group consisting of SUZUKI-, YAMAMOTO-, STILLE-, NIGESHI-, KUMADA-, HECK-, SONOGASHIRA-, HIYAMA-, FUKUYAMA-. Particularly suitable and preferred coupling reactions are SUZUKI, STILLE and YAMAMOTO coupling reactions. Suitable reactions to form a C—N link are HARTWIG-BUCHWALD- and ULLMAN reactions. Information including specific application conditions and operation methods of each reaction type has been well known in the field of metal-catalyzed cross-coupling reactions for many years, and now there have been sufficient development and mature research, industrialization methods, which will not be described in detail here.

The present disclosure further provides a mixture including the foregoing polymer, and another organic functional material which may be selected from the group consisting of a hole (also called electron hole) injection or transporting material (HIM/HTM), a hole blocking material (HBM), an electron injection or transporting material (EIM/ETM), an electron blocking material (EBM), an organic matrix material (Host), a singlet emitter (a fluorescent emitter), a triplet emitter (a phosphorescent emitter), a thermally activated delayed fluorescent material (a TADF material), and an organic dye. Various organic functional materials are described in detail, for example, in WO2010135519A1, US20090134784A1 and WO2011110277A1, the entire contents of which three patent documents are incorporated herein by reference.

In an embodiment, the foregoing mixture includes the foregoing conjugated polymer, and a fluorescent emitter (or a singlet emitter). In an embodiment, the foregoing conjugated polymer may be used as a host, wherein the fluorescent emitter has a weight percentage less than or equal to 15 wt %. In an embodiment, the foregoing conjugated polymer may be used as a host, wherein the fluorescent emitter has a weight percentage in the mixture less than or equal to 12 wt %. In an embodiment, the foregoing conjugated polymer may be used as a host, wherein the fluorescent emitter has a weight percentage in the mixture less than or equal to 9 wt %. In an embodiment, the foregoing conjugated polymer may be used as a host, wherein the fluorescent emitter has a weight percentage in the mixture less than or equal to 8 wt %. In an embodiment, the foregoing conjugated polymer may be used as a host, wherein the fluorescent emitter has a weight percentage in the mixture less than or equal to 7 wt %.

In a certain embodiment, the foregoing mixture includes the foregoing conjugated polymer, and a TADF material.

In an embodiment, the foregoing mixture includes the foregoing conjugated polymer, and a phosphorescent emitter (or a triplet emitter). In an embodiment, the foregoing conjugated polymer may be used as a host, wherein the phosphorescent emitter has a weight percentage in the mixture less than or equal to 30 wt %. In an embodiment, the foregoing conjugated polymer may be used as a host, wherein the phosphorescent emitter has a weight percentage in the mixture less than or equal to 25 wt %. In an embodiment, the foregoing conjugated polymer may be used as a host, wherein the phosphorescent emitter has a weight percentage in the mixture less than or equal to 20 wt %. In an embodiment, the foregoing conjugated polymer may be used as a host, wherein the phosphorescent emitter has a weight percentage in the mixture less than or equal to 18 wt %.

In another embodiment, the foregoing mixture includes the foregoing conjugated polymer, and an HTM material.

The singlet emitter, the triplet emitter, and the TADF material are described in detail below (but are not limited thereto).

1. Singlet Emitter

A singlet emitter tends to have a longer conjugated π-electron system. There have been many examples so far, such as the styrylamine and derivatives thereof disclosed in JP2913116B and WO2001021729A1, and the indenofluorene and derivatives thereof disclosed in WO2008/006449 and WO2007/140847.

In an embodiment, the singlet emitter may be selected from the group consisting of a monostyrylamine, a distyrylamine, a tristyrylamine, a tetrastyrylamine, a styryl phosphine, a styryl ether, and an aryl amine.

A monostyrylamine refers to a compound including an unsubstituted or substituted styryl group and at least one amine, particularly one aryl amine. A distyrylamine refers to a compound including two unsubstituted or substituted styryl groups and at least one amine, particularly one aryl amine. A tristyrylamine refers to a compound including three unsubstituted or substituted styryl groups and at least one amine, particularly one aryl amine. A tetrastyrylamine refers to a compound including four unsubstituted or substituted styryl groups and at least one amine, particularly one aryl amine. In one embodiment, a styrene is stilbene, which may be further substituted. The corresponding phosphines and ethers are defined similarly as amines. An aryl amine or aromatic amine refers to a compound including three unsubstituted or substituted aromatic ring or heteroaromatic ring systems directly attached to nitrogen. In one embodiment, at least one of these aromatic ring or heteroaromatic ring systems is selected from fused ring systems and particularly has at least 14 aromatic ring atoms. Suitable examples are an aromatic anthramine, an aromatic anthradiamine, an aromatic pyrene amine, an aromatic pyrene diamine, an aromatic chrysene amine and an aromatic chrysene diamine. An aromatic anthramine refers to a compound in which one diaryl amino group is directly attached to anthracene, particularly at position 9. An aromatic anthradiamine refers to a compound in which two diarylamino groups are directly attached to anthracene, particularly at positions 9, 10. Aromatic pyrene amines, aromatic pyrene diamines, aromatic chrysene amines and aromatic chrysene diamine are similarly defined, wherein the diarylarylamino group is particularly attached to position 1, or 1 and 6 of pyrene.

Examples of singlet emitters based on vinylamine and aryl amine may be found in the following patent documents: WO2006/000388, WO2006/058737, WO2006/000389, WO2007/065549, WO2007/115610, U.S. Pat. No. 7,250, 532 B2, DE102005058557 A1, CN1583691 A, JP08053397 A, U.S. Pat. No. 6,251,531 B1, US2006/210830 A, EP1957606 A1, and US2008/0113101 A1, and the entire contents of the above-listed patent documents are incorporated herein by reference.

Examples of singlet emitters based on distyrylbenzene and derivatives thereof may be found in U.S. Pat. No. 5,121,029.

Further, the singlet emitters may be selected from the group consisting of: indenofluorene-amine and indenofluorene-diamine such as disclosed in WO2006/122630, benzoindenofluorene-amine and benzoindenofluorene-diamine such as disclosed in WO2008/006449, dibenzoindenofluorene-amine and dibenzoindenofluorene-diamine such as disclosed in WO2007/140847.

Other materials that may be used as singlet emitters include polycyclic aromatic hydrocarbon compounds, especially derivatives of the following compounds: anthracene such as 9,10-di(2-naphthylanthracene), naphthalene, tetraphenyl, xanthene, phenanthrene, pyrene (such as 2,5,8,11-tetra-t-butylperylene), indenopyrene, phenylene (such as 4,4'-(bis (9-ethyl-3-carbazovinylene)-1,1'-biphenyl), periflanthene, decacyclene, coronene, fluorene, spirobifluorene, arylpyrene (e.g., US20060222886), arylenevinylene (e.g., U.S. Pat. Nos. 5,121,029, 5,130,603), cyclopentadiene such as tetraphenylcyclopentadiene, rubrene, coumarine, rhodamine, quinacridone, pyrane such as 4(dicyanomethylene)-6-(4-p-dimethylaminostyryl-2-methyl)-4H-pyrane (DCM), thiapyran, bis(azinyl)imine-boron compounds (US 2007/0092753 A1), bis(azinyl)methene compound, carbostyryl compound, oxazone, benzoxazole, benzothiazole, benzimidazole, and diketopyrrolopyrrole. Examples of some singlet emitter materials may be found in the following patent documents: US 20070252517 A1, U.S. Pat. Nos. 4,769,292, 6,020,078, US 2007/0252517 A1, US 2007/0252517 A1. The entire contents of the above-listed patent documents are incorporated herein by reference.

Examples of suitable singlet emitters are listed in the following table:

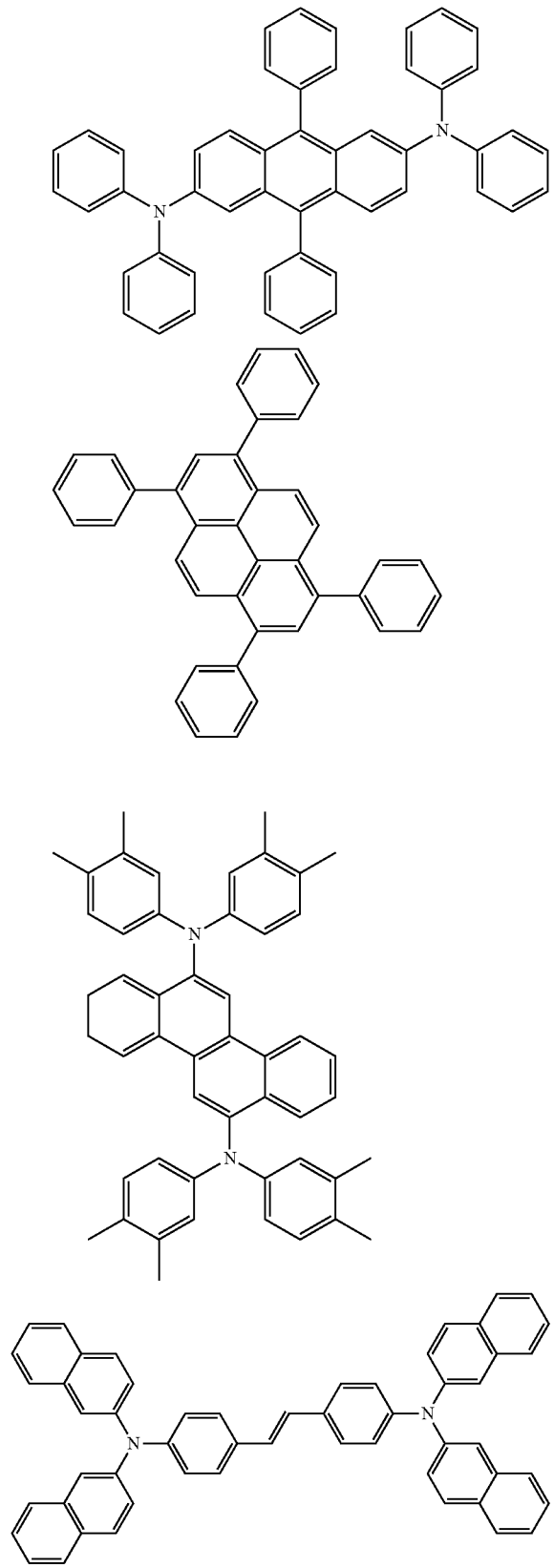

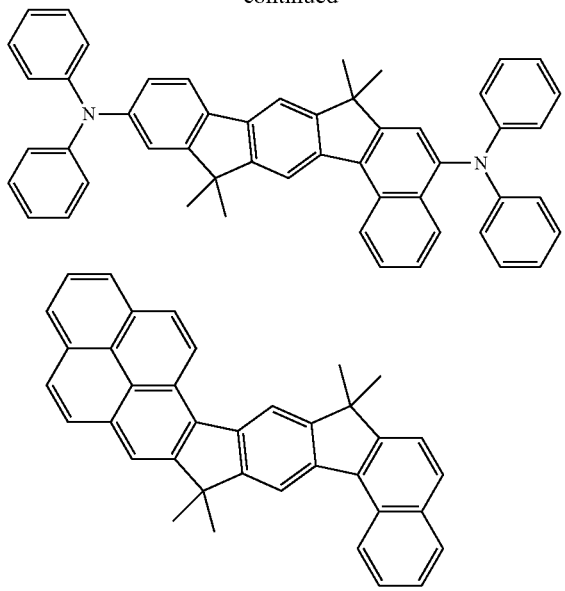

2. Triplet Emitter (Phosphorescent Emitter)

A triplet emitter is also called a phosphorescent emitter. In an embodiment, the triplet emitter is a metal clathrate having a general formula M(L)n; wherein M is a metal atom, L may be identical or different each time it is present and is an organic ligand, bonded or coordinated to the metal atom M through one or more positions; n is an integer greater than 1, further n is 1, 2, 3, 4, 5 or 6. Selectively, such metal clathrate is coupled to a polymer through one or more positions, particularly through an organic ligand.

In an embodiment, the metal atom M is selected from the group consisting of a transition metal element or a lanthanide element or an actinide element, further selected from the group consisting of Ir, Pt, Pd, Au, Rh, Ru, Os, Sm, Eu, Gd, Tb, Dy, Re, Cu or Ag, and particularly selected from the group consisting of Os, Ir, Ru, Rh, Re, Pd or Pt.

In one embodiment, the triplet emitter includes a chelating ligand, i.e., a ligand, coordinated to a metal by at least two bonding sites, and it is particularly for consideration that the triplet emitter includes two or three identical or different bidentate or multidentate ligands. A chelating ligand is beneficial for improving the stability of a metal clathrate.

Examples of organic ligands may be selected from the group consisting of a phenylpyridine derivative, a 7,8-benzoquinoline derivative, a 2(2-thienyl)pyridine derivative, a 2(1-naphthyl)pyridine derivative, or a 2-phenylquinoline derivative. All of these organic ligands may be substituted, for example, with fluorine containing groups or trifluoromethyl. The auxiliary ligand may be preferably selected from acetylacetonate or picric acid.

In an embodiment, the metal clathrate which may be used as a triplet emitter has the following form:

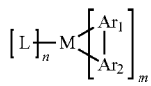

wherein M is a metal and selected from a transition metal element or a lanthanide or an actinide element;

Ar$_1$ may be identical or different each time it is present and is a cyclic group, which includes at least one donor atom, i.e., an atom with a lone pair of electrons, such as nitrogen or phosphorus, through which the cyclic group is coordinated to the metal; Ar$_2$ may be identical or different each time it is present and is a cyclic group, which includes at least one C atom through which the cyclic group is coordinated to the metal; Ar$_1$ and Ar$_2$ are covalently bonded together and each of them may carry one or more substituents, and they may further be linked together by substituents; L may be identical or different each time it is present and is an auxiliary ligand, further a bidentate chelating ligand, and most particularly a monoanionic bidentate chelating ligand; m is 1, 2 or 3, further 2 or 3, and particularly 3; n is 0, 1, or 2, further 0 or 1, and particularly 0.

Examples of triplet emitter materials and applications thereof may be found in the following patent documents and literature: WO 200070655, WO 200141512, WO 200202714, WO 200215645, EP 1191613, EP 1191612, EP 1191614, WO 2005033244, WO 2005019373, US 2005/0258742, WO 2009146770, WO 2010015307, WO 2010031485, WO 2010054731, WO 2010054728, WO 2010086089, WO 2010099852, WO 2010102709, US 20070087219 A1, US 20090061681 A1, US 20010053462 A1, Baldo, Thompson et al. Nature 403, (2000), 750-753, US 20090061681 A1, US 20090061681 A1, Adachi et al. Appl. Phys. Lett. 78 (2001), 1622-1624, J. Kido et al. Appl. Phys. Lett. 65 (1994), 2124, Kido et al. Chem. Lett. 657, 1990, US 2007/0252517 A1, Johnson et al., JACS 105, 1983, 1795, Wrighton, JACS 96, 1974, 998, Ma et al., Synth. Metals 94, 1998, 245, U.S. Pat. Nos. 6,824,895, 7,029,766, 6,835,469, 6,830,828, US 20010053462 A1, WO 2007095118 A1, US 2012004407A1, WO 2012007088A1, WO2012007087A1, WO 2012007086A1, US 2008027220A1, WO 2011157339A1, CN 102282150A, WO 2009118087A1. The entire contents of the above-listed patent documents and literature are hereby incorporated by reference.

Examples of suitable triplet emitters are provided in the following table:

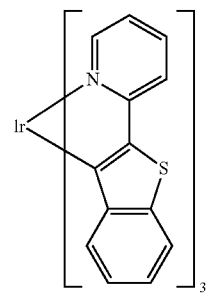

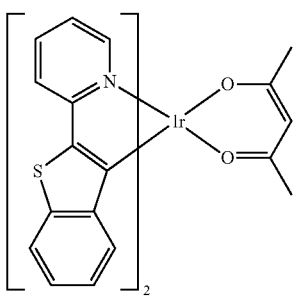

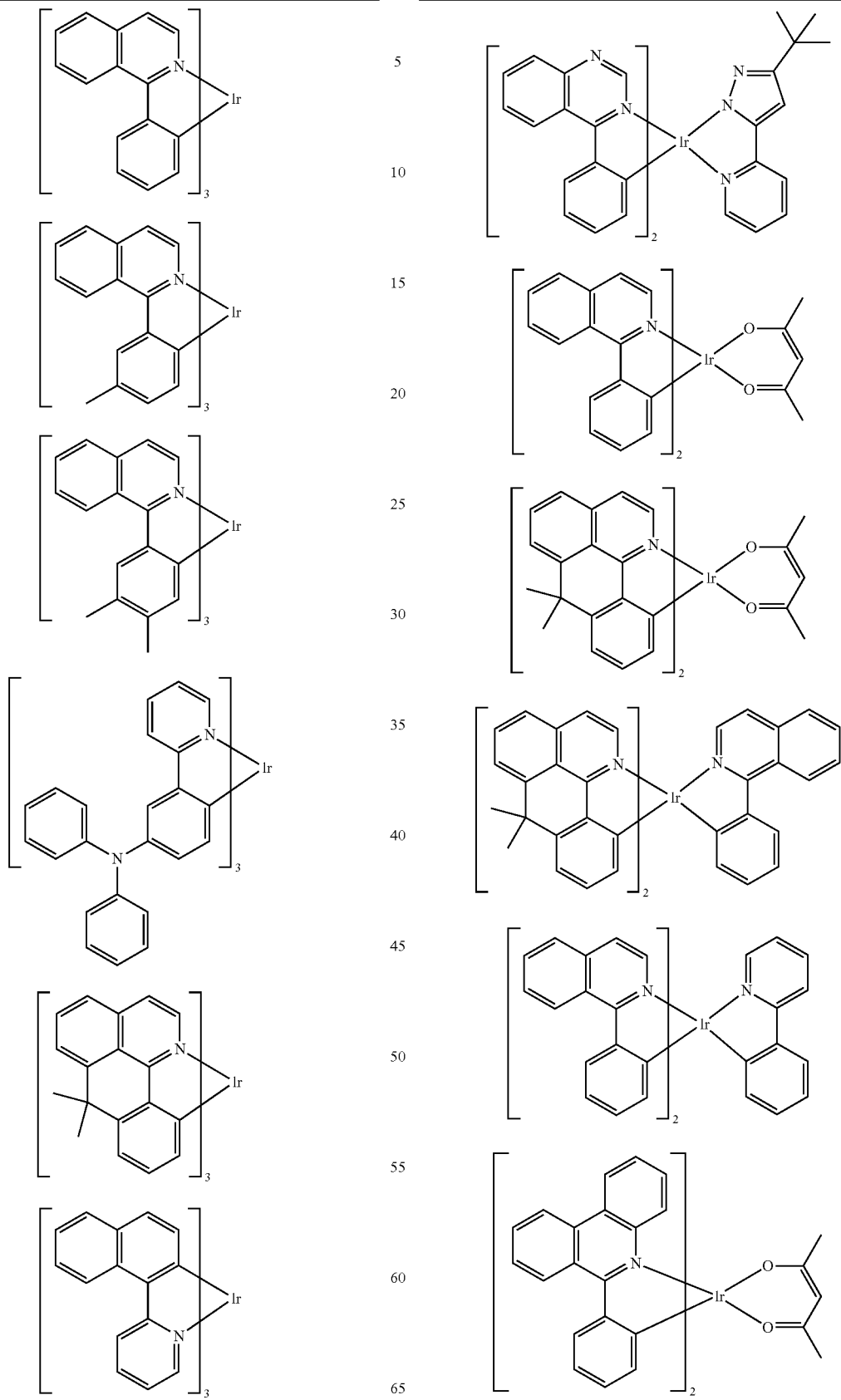

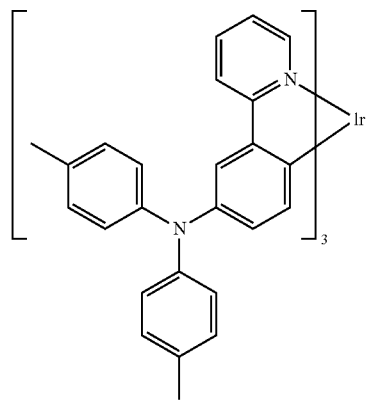
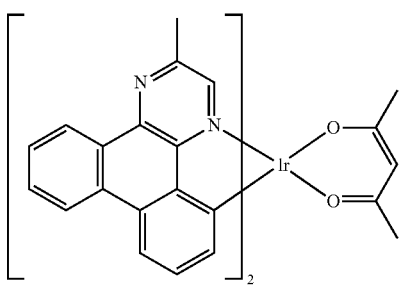
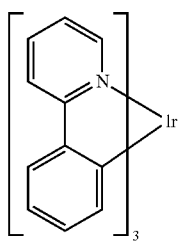
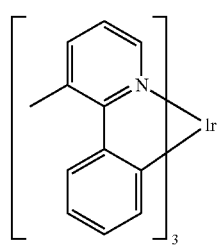
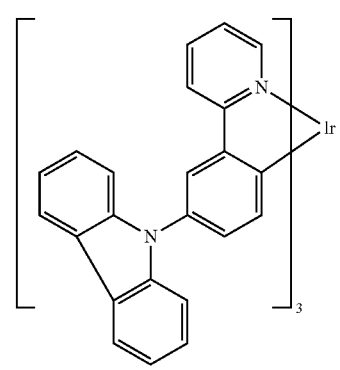
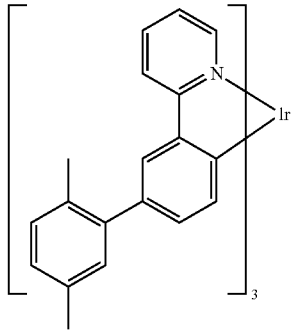
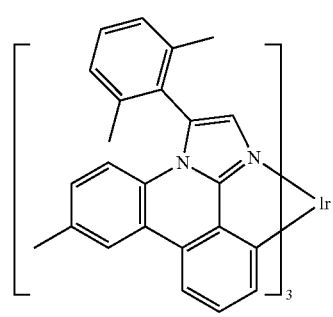
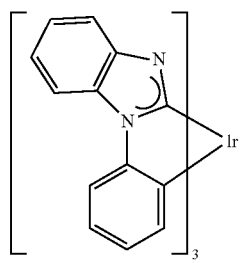
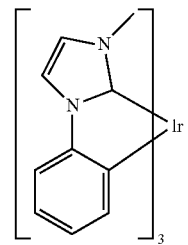
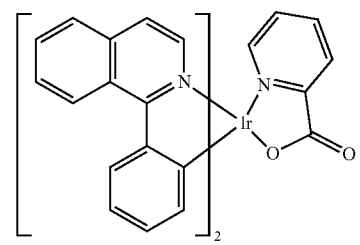

99
-continued

100
-continued

| 101 -continued | 102 -continued |
|---|---|
| 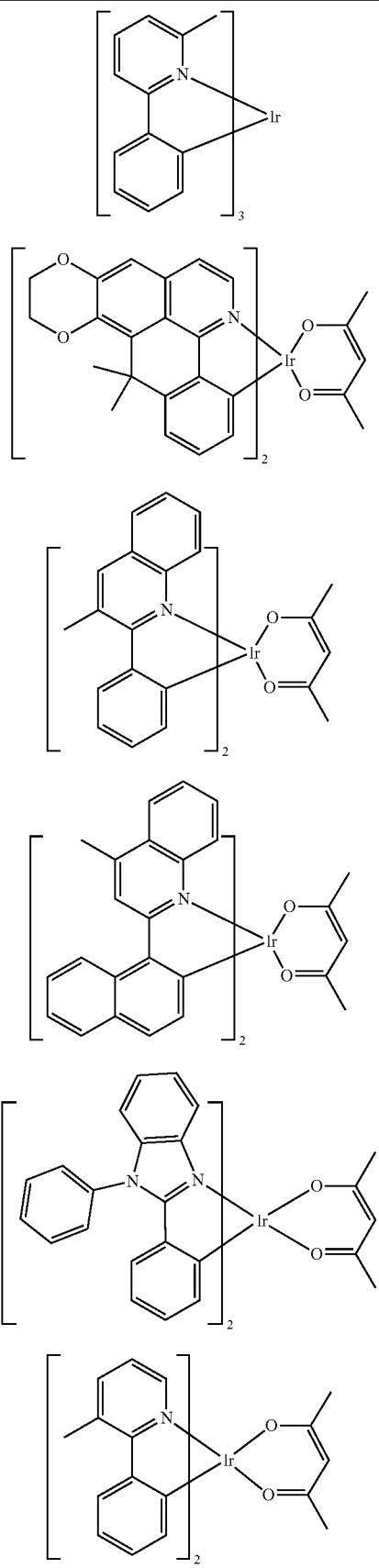 | 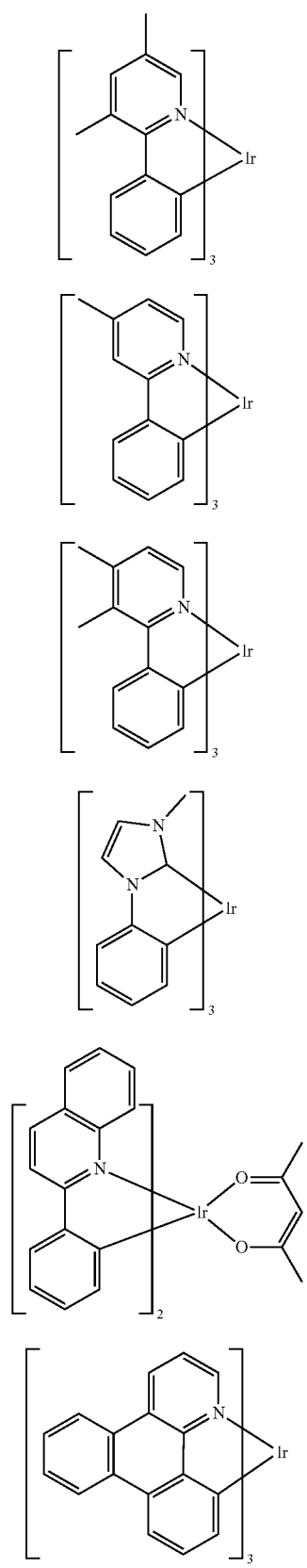 |

-continued

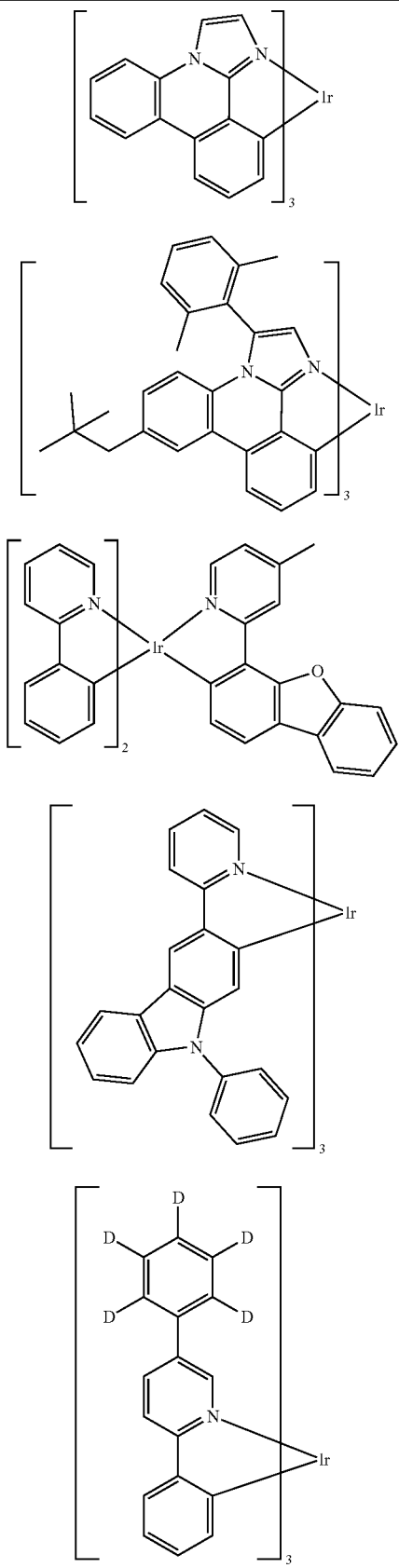

3. Thermally Activated Delayed Fluorescent Material (TADF)

Conventional organic fluorescent materials can only emit light using 25% singlet excitonic luminescence formed by electrical excitation, and the devices have relatively low internal quantum efficiency (up to 25%). A phosphorescent material enhances the intersystem crossing due to the strong spin-orbit coupling of the heavy atom center, the singlet exciton and the triplet exciton luminescence formed by the electric excitation can be effectively utilized, so that the internal quantum efficiency of the device can reach 100%. However, the phosphor materials are expensive, the material stability is poor, and the device efficiency roll-off is a serious problem, which limits its application in OLED. Thermally activated delayed fluorescent materials are the third generation of organic light-emitting materials developed after organic fluorescent materials and organic phosphorescent materials. This type of material generally has a small singlet-triplet excited state energy level difference ($\Delta Est$), and triplet excitons can be converted to singlet excitons by anti-intersystem crossing. This can make full use of the singlet excitons and triplet excitons formed under electric excitation. The device can achieve 100% quantum efficiency. At the same time, the material structure is controllable, the property is stable, the price is cheap, no noble metal is needed, and the application prospect in the OLED field is broad.

The TADF material needs to have a small singlet-triplet excited state energy level difference, generally $\Delta Est<0.3$ eV, further $\Delta Est<0.2$ eV, and still further $\Delta Est<0.1$ eV. In an embodiment, the TADF material has a small $\Delta Est$, and in another embodiment, the TADF has a good fluorescence quantum efficiency. Some TADF light-emitting materials can be found in the following patent documents: CN103483332(A), TW201309696(A), TW201309778(A), TW201343874(A), TW201350558(A), US20120217869 (A1), WO2013133359(A1), WO2013154064(A1), Adachi, et. al. Adv. Mater., 21, 2009, 4802, Adachi, et. al. Appl. Phys. Lett., 98, 2011, 083302, Adachi, et. al. Appl. Phys. Lett., 101, 2012, 093306, Adachi, et. al. Chem. Commun., 48, 2012, 11392, Adachi, et. al. Nature Photonics, 6, 2012, 253, Adachi, et. al. Nature, 492, 2012, 234, Adachi, et. al. J. Am. Chem. Soc, 134, 2012, 14706, Adachi, et. al. Angew. Chem. Int. Ed, 51, 2012, 11311, Adachi, et. al. Chem. Commun., 48, 2012, 9580, Adachi, et. al. Chem. Commun., 48, 2013, 10385, Adachi, et. al. Adv. Mater., 25, 2013, 3319, Adachi, et. al. Adv. Mater., 25, 2013, 3707, Adachi, et. al. Chem. Mater., 25, 2013, 3038, Adachi, et. al. Chem. Mater., 25, 2013, 3766, Adachi, et. al. J. Mater. Chem. C., 1, 2013, 4599, Adachi, et. al. J. Phys. Chem. A., 117, 2013, 5607, and the entire contents of the above-listed patent or literature documents are hereby incorporated by reference.

Some examples of suitable TADF light-emitting materials are listed in the following table:

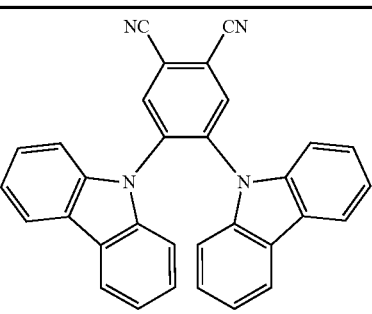

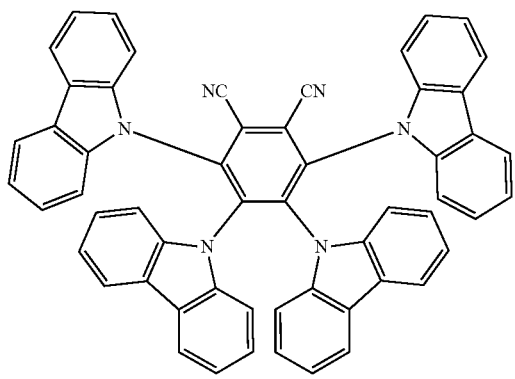 [SMILES: N#Cc1c(C#N)c(-n2c3ccccc3c3ccccc32)c(-n2c3ccccc3c3ccccc32)c(-n2c3ccccc3c3ccccc32)c1-n1c2ccccc2c2ccccc21]
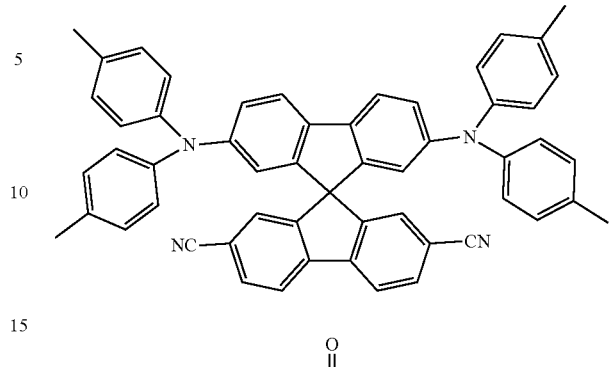
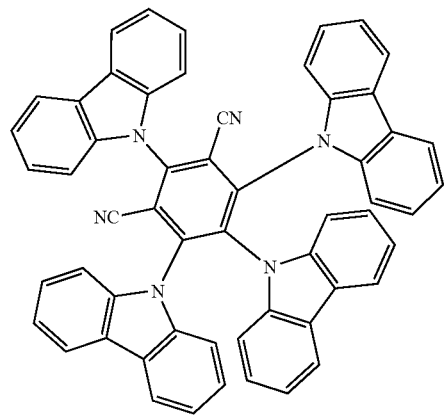 [SMILES: N#Cc1c(-n2c3ccccc3c3ccccc32)c(C#N)c(-n2c3ccccc3c3ccccc32)c(-n2c3ccccc3c3ccccc32)c1-n1c2ccccc2c2ccccc21]
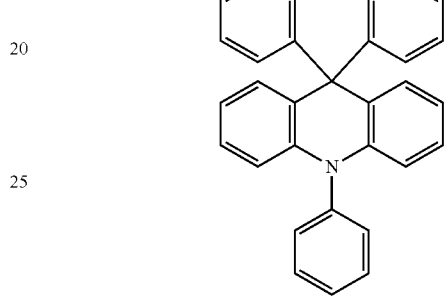
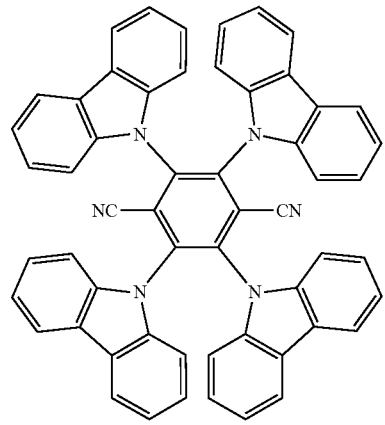 [SMILES: N#Cc1c(-n2c3ccccc3c3ccccc32)c(-n2c3ccccc3c3ccccc32)c(C#N)c(-n2c3ccccc3c3ccccc32)c1-n1c2ccccc2c2ccccc21]
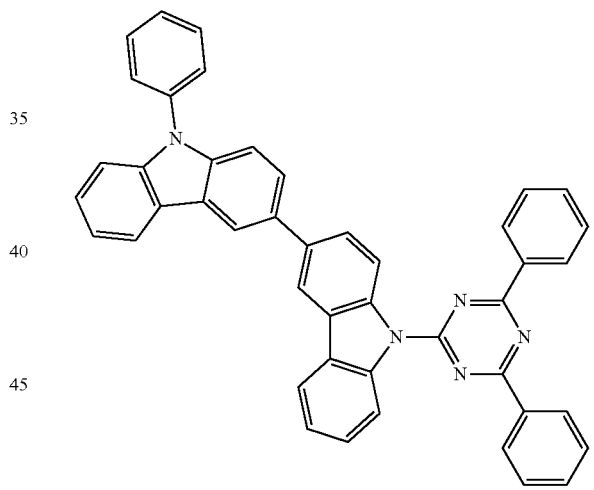
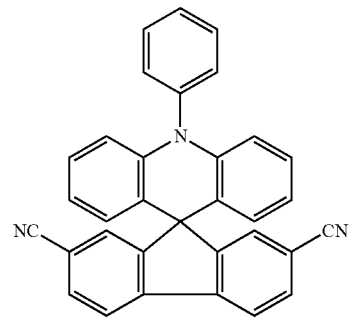 [SMILES: N#Cc1ccc2c(c1)C1(c3cc(C#N)ccc3-2)c2ccccc2N(c2ccccc2)c2ccccc21]
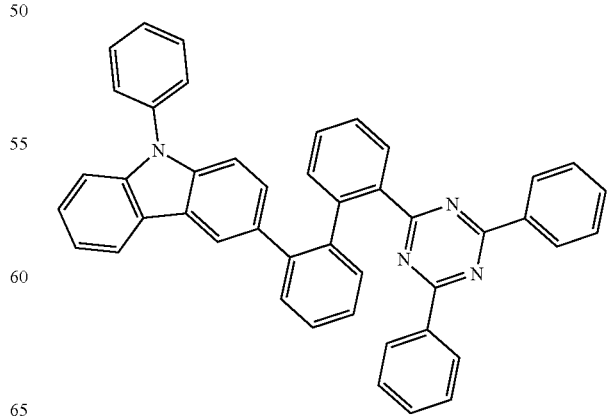

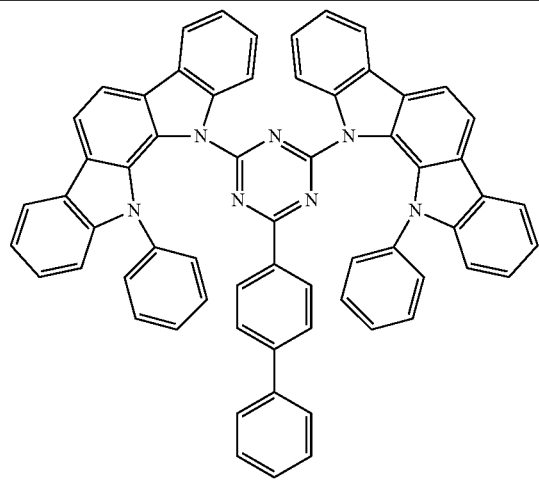
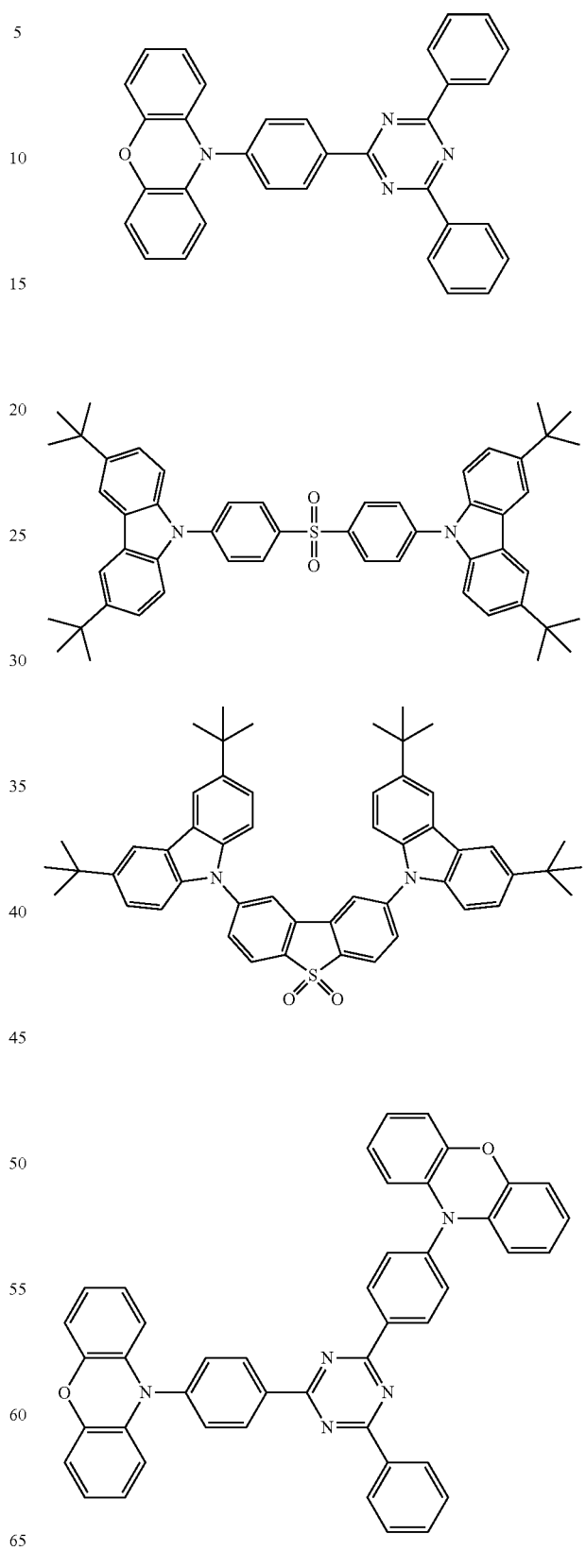

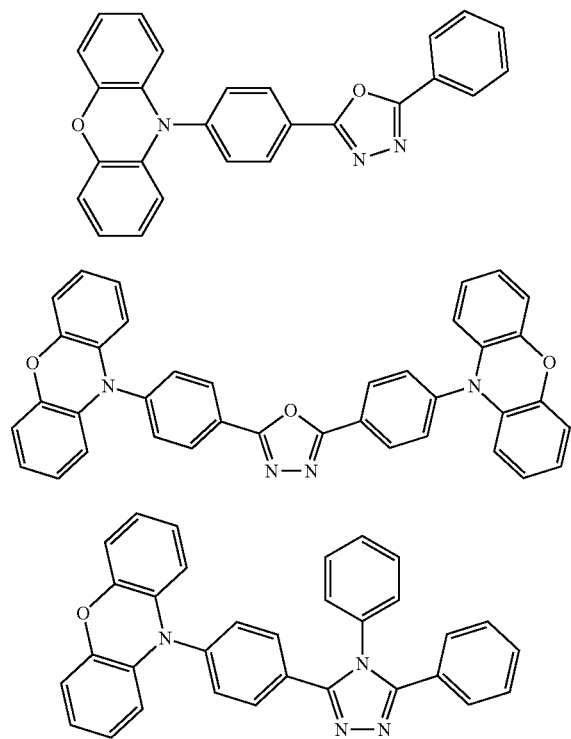
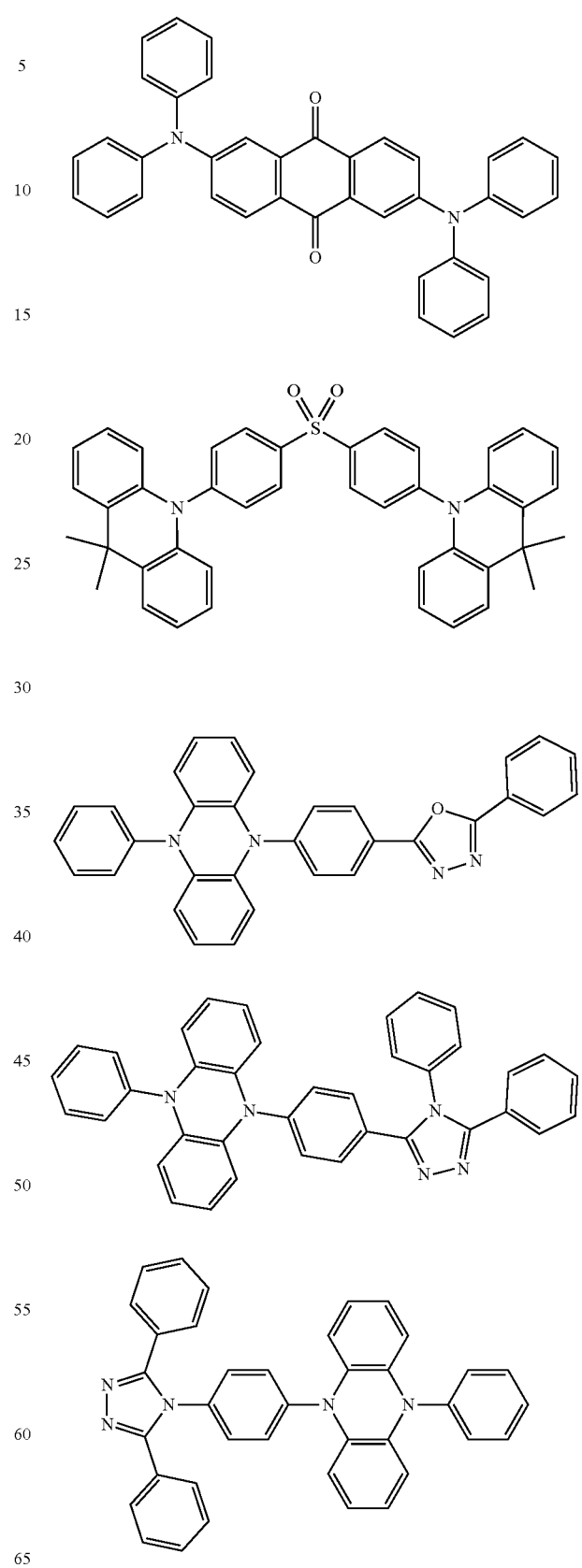

111
-continued
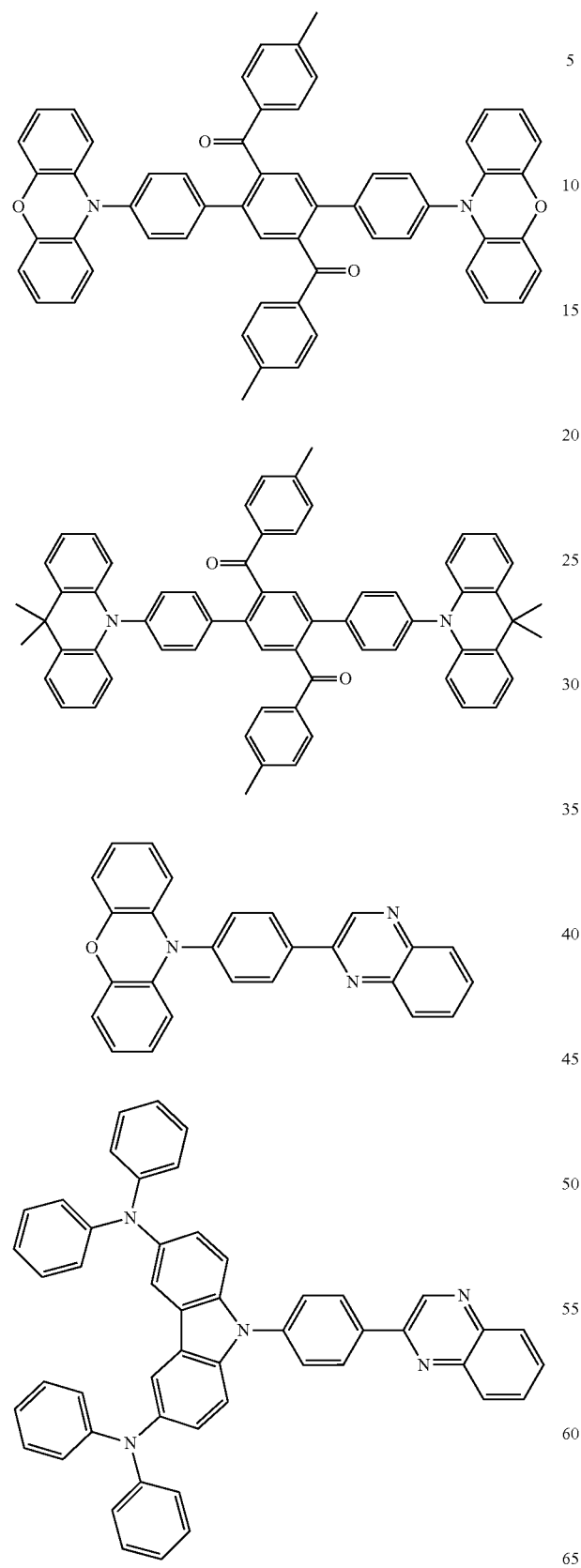
112
-continued
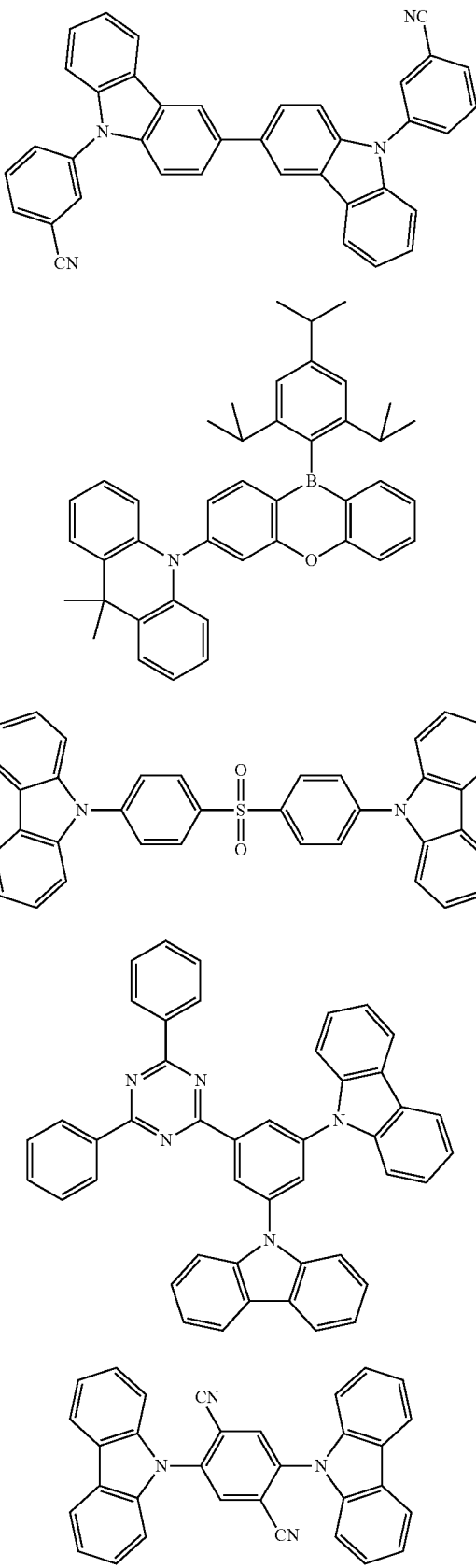

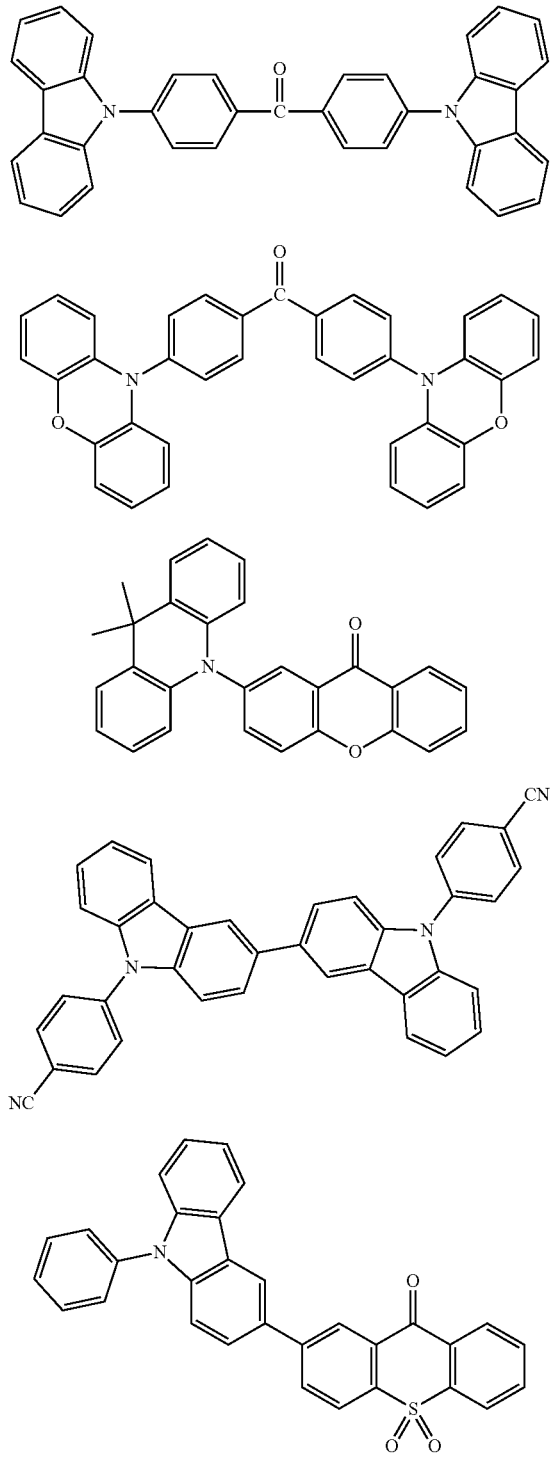

The publications of organic functional material for the organic functional structural units described above are hereby incorporated by reference for the purpose of disclosure.

Another object of the present disclosure is to provide a material solution for printing OLEDs.

In certain embodiments, the foregoing conjugated polymer has a molecular weight greater than or equal to 100 kg/mol. In certain embodiments, the foregoing conjugated polymer has a molecular weight greater than or equal to 150 kg/mol. In certain embodiments, the foregoing conjugated polymer has a molecular weight greater than or equal to 180 kg/mol. In certain embodiments, the foregoing conjugated polymer has a molecular weight greater than or equal to 200 kg/mol.

In other embodiments, the foregoing conjugated compound has a solubility in toluene greater than or equal to 5 mg/ml, further greater than or equal to 7 mg/ml, and still further greater than or equal to 10 mg/ml at 25° C.

The present disclosure further relates to a formulation or an ink including the polymer according to the present disclosure or a mixture thereof, and at least one organic solvent. The present disclosure further provides a thin film including the polymer according to the present disclosure prepared from a solution.

In a printing process, the viscosity and surface tension of an ink is important parameters. Suitable surface tension parameters of an ink are suitable for a particular substrate and a particular printing method.

In an embodiment, the ink according to the present disclosure has a surface tension at an operating temperature or at 25° C. in the range of about 19 dyne/cm to 50 dyne/cm; further in the range of 22 dyne/cm to 35 dyne/cm; and still further in the range of 25 dyne/cm to 33 dyne/cm.

In another embodiment, the ink according to the present disclosure has a viscosity at the working temperature or at 25° C. in the range of about 1 cps to 100 cps, further in the range of 1 cps to 50 cps, still further in the range of 1.5 cps to 20 cps, and even further in the range of 4.0 cps to 20 cps. The formulation thus formulated will be suitable for inkjet printing.

The viscosity can be adjusted by different methods, such as by selecting a suitable solvent and the concentration of the functional material in the ink. The ink including the foregoing polymer according to the present disclosure can facilitate the adjustment of the printing ink in an appropriate range according to the printing method used. Generally, the functional material in the formulation according the present disclosure has a weight ratio in the range of 0.3 wt % to 30 wt %, further in the range of 0.5 wt % to 20 wt %, still further in the range of 0.5 wt % to 15 wt %, still further in the range of 0.5 wt % to 10 wt %, and even further in the range of 1 wt % to 5 wt %.

In some embodiments, in the ink according to the present disclosure, the at least one organic solvent is selected from the solvents based on aromatics or heteroaromatics, especially aliphatic chain/ring substituted aromatic solvents, or aromatic ketone solvents, or aromatic ether solvents.

Examples of the solvents suitable for the present disclosure are, but are not limited to, solvents based on aromatics or heteroaromatics: p-diisopropylbenzene, pentylbenzene, tetrahydronaphthalene, cyclohexyl benzene, chloronaphthalene, 1,4-dimethylnaphthalene, 3-isopropylbiphenyl, p-cymene, dipentylbenzene, tripentylbenzene, pentyltoluene, o-xylene, m-xylene, p-xylene, o-diethylbenzene, m-diethylbenzene, p-diethylbenzene, 1,2,3,4-tetramethylbenzene, 1,2,3,5-tetramethylbenzene, 1,2,4,5-tetramethylbenzene, butylbenzene, dodecylbenzene, dihexylbenzene, dibutylbenzene, p-diisopropylbenzene, 1-methoxynaphthalene, cyclohexylbenzene, dimethylnaphthalene, 3-isopropylbiphenyl, p-cymene, 1-methylnaphthalene, 1,2,4-trichlorobenzene, 1,3-dipropoxybenzene, 4,4-difluorodiphenylmethane, 1,2-dimethoxy-4-(1-propenyl)benzene, diphenylmethane, 2-phenylpyridine, 3-phenylpyridine, N-methyldiphenylamine 4-isopropylbiphenyl, α,α-dichlorodiphenylmethane, 4-(3-phenylpropyl)pyridine, benzylbenzoate, 1,1-di(3,4-dimethylphenyl)ethane, 2-isopropylnaphthalene, dibenzylether, and the like; solvents based on ketones: 1-tetralone, 2-tetralone, 2-(phenylepoxy)tetralone, 6-(methoxyl)tetralone, acetophenone, phenylacetone, benzophenone, and derivatives thereof, such as 4-methylacetophenone, 3-methylacetophenone, 2-methylacetophenone, 4-methylphenylacetone, 3-methylphenylacetone, 2-methylphenylacetone, isophorone, 2,6,8-trimethyl-4-nonanone, fenchone, 2-nonanone, 3-nonanone, 5-nonanone, 2-decanone, 2,5-hexanedione, phorone, di-n-amyl ketone; aromatic ether solvents: 3-phenoxytoluene, butoxybenzene, benzylbutylbenzene, p-anisaldehyde dimethyl acetal, tetrahydro-2-phenoxy-2H-pyran, 1,2-dimethoxy-4-(1-propenyl) benzene, 1,4-benzodioxane, 1,3-dipropylbenzene, 2,5-dimethoxytoluene, 4-ethylphenetole, 1,2,4-trimethoxybenzene, 4-(1-propenyl)-1,2-dimethoxybenzene, 1,3-dimethoxybenzene, glycidyl phenyl ether, dibenzyl ether, 4-tert-butylanisole, trans-p-propenylanisole, 1,2-dimethoxybenzene, 1-methoxynaphthalene, diphenyl ether, 2-phenoxymethyl ether, 2-phenoxytetrahydrofuran, ethyl-2-naphthyl ether, pentyl ether, hexyl ether, dioctyl ether, ethylene glycol dibutyl ether, diethylene glycol diethyl ether, diethylene glycol butyl methyl ether, diethylene glycol dibutyl ether, triethylene glycol dimethyl ether, triethylene glycol ethyl methyl ether, triethylene glycol butyl methyl ether, tripropylene glycol dimethyl ether, tetraethylene glycol dimethyl ether; and ester solvents: alkyl octoate, alkyl sebacate, alkyl stearate, alkyl benzoate, alkyl phenylacetate, alkyl cinnamate, alkyl oxalate, alkyl maleate, alkyl lactone, alkyl oleate, and the like.

Further, in the ink according to the present disclosure, the at least one organic solvent can be selected from aliphatic ketones, such as 2-nonanone, 3-nonanone, 5-nonanone, 2-decanone, 2,5-hexanedione, 2,6,8-trimethyl-4-nonanone, phorone, di-n-pentyl ketone, and the like; or aliphatic ethers, such as amyl ether, hexyl ether, dioctyl ether, ethylene glycol dibutyl ether, diethylene glycol diethyl ether, diethylene glycol butyl methyl ether, diethylene glycol dibutyl ether, triethylene glycol dimethyl ether, triethylene glycol ethyl methyl ether, triethylene glycol butyl methyl ether, tripropylene glycol dimethyl ether, tetraethylene glycol dimethyl ether.

In other embodiments, the foregoing printing ink further includes another organic solvent. Examples of the other organic solvents include, but are not limited to, methanol, ethanol, 2-methoxyethanol, dichloromethane, trichloromethane, chlorobenzene, o-dichlorobenzene, tetrahydrofuran, anisole, morpholine, toluene, o-xylene, m-xylene, p-xylene, 1,4-dioxahexane, acetone, methyl ethyl ketone, 1,2-dichloroethane, 3-phenoxytoluene, 1,1,1-trichloroethane, 1,1,2,2-tetrachloroethane, ethyl acetate, butyl acetate, dimethylformamide, dimethylacetamide, dimethyl sulfoxide, tetrahydronaphthalene, naphthane, indene and/or their mixtures.

In an embodiment, the foregoing formulation is a solution.

In another embodiment, the foregoing formulation is a suspension.

The present disclosure further relates to use of the foregoing formulation as a printing ink in the preparation of an organic electronic device, and particularly by a preparation method of printing or coating.

Suitable printing or coating techniques include, but are not limited to, inkjet printing, nozzle printing, typography, screen printing, dip coating, spin coating, blade coating, roller printing, twist roller printing, lithography, flexography, rotary printing, spray coating, brush coating or transfer printing, nozzle printing, slot die coating, and the like. The first preference is inkjet printing, slot die coating, nozzle printing, and gravure printing.

The solution or suspension may additionally include one or more components such as a surface active compound, a lubricant, a wetting agent, a dispersing agent, a hydrophobic agent, a binder, and the like, for adjusting viscosity, film-forming properties and improving adhesion. The detailed information relevant to the printing technology and requirements of the printing technology to the solution, such as solvent, concentration, and viscosity, may be referred to Handbook of Print Media: Technologies and Production Methods, Helmut Kipphan, ISBN 3-540-67326-1.

Based on the foregoing polymers, the present disclosure further provides use of the foregoing polymer in an organic electronic device. The organic electronic device may be selected from, but not limited to, an organic light-emitting diode (OLED), an organic photovoltaic (OPV), an organic light-emitting electrochemical cell (OLEEC), an organic field effect transistor (OFET), an organic light-emitting field effector, an organic laser, an organic spintronic device, an organic sensor, and an organic plasmon emitting diode, especially an OLED. In the embodiments of the present disclosure, the foregoing polymer is particularly used in a hole transporting layer or a hole injection layer or a light-emitting layer in an OLED.

The present disclosure further relates to an organic electronic device including a functional layer prepared from the foregoing conjugated polymer, the foregoing mixture or the foregoing formulation. Generally, this type of organic electronic device includes a cathode, an anode and a functional layer located between the cathode and the anode, wherein the functional layer includes at least the foregoing conjugated polymer, the foregoing mixture or prepared from the foregoing formulation.

In one embodiment, the organic electronic device is an organic light-emitting diode (OLED), an organic photovoltaic cell (OPV), an organic light-emitting electrochemical cell (OLEEC), an organic field effect transistor (OFET), an organic light-emitting field effector, an organic laser, an organic spintronic device, an organic sensor, and an organic plasmon emitting diode.

In an embodiment, the foregoing organic electronic device is an electroluminescent device, especially an OLED (as shown FIG. 1), wherein a substrate 101, an anode 102, at least a light-emitting layer 104, and a cathode 106 are included.

The substrate 101 can be opaque or transparent. A transparent substrate may be used to make a transparent light-emitting device. For example, please refer to Bulovic et al., Nature, 1996, 380, page 29 and Gu et al., Appl. Phys. Lett., 1996, 68, p 2606. The substrate may be rigid or elastic. The substrate may be plastic, metal, semiconductor wafer or glass. Particularly, the substrate has a smooth surface. The substrate without any surface defects is a particular ideal selection. In an embodiment, the substrate is flexible and may be selected from a polymer thin film or a plastic which have a glass transition temperature Tg greater than 150° C., further greater than 200° C., still further greater than 250° C., and even further greater than 300° C. Suitable examples of the flexible substrate are polyethylene terephthalate (PET) and polyethylene 2,6-naphthalate (PEN).

The anode 102 may include a conductive metal, metallic oxide, or conductive polymer. The anode can inject holes easily into a hole injection layer (HIL), a hole transporting layer (HTL), or a light-emitting layer. In an embodiment, the absolute value of the difference between the work function of the anode and the HOMO energy level or the valence band energy level of the emitter in the light-emitting layer or of the p-type semiconductor material of the HIL or HTL or the electron blocking layer (EBL) is smaller than 0.5 eV, further smaller than 0.3 eV, and still further smaller than 0.2 eV. Examples of the anode material include, but are not limited to Al, Cu, Au, Ag, Mg, Fe, Co, Ni, Mn, Pd, Pt, ITO, aluminum-doped zinc oxide (AZO), and the like. Other suitable anode materials are known and may be easily selected by those skilled in the art. The anode material may be deposited by any suitable technologies, such as a suitable physical vapor deposition method which includes a radio frequency magnetron sputtering, a vacuum thermal evaporation, an electron beam (e-beam), and the like. In some embodiments, the anode is patterned and structured. A patterned ITO conductive substrate may be purchased from market to prepare the device according to the present disclosure.

The cathode 106 may include a conductive metal or metal oxide. The cathode can inject electrons easily into the EIL or the ETL, or directly injected into the light-emitting layer. In an embodiment, the absolute value of the difference between the work function of the cathode and the LUMO energy level or the valence band energy level of the emitter in the light-emitting layer or of the n-type semiconductor material as the electron injection layer (EIL) or the electron transport layer (ETL) or the hole blocking layer (HBL) is smaller than 0.5 eV, further smaller than 0.3 eV, and still further smaller than 0.2 eV. In principle, all materials that can be used as a cathode for an OLED can be used as a cathode material for the devices of the disclosure. Examples of the cathode materials include, but not limited to Al, Au, Ag, Ca, Ba, Mg, LiF/Al, MgAg alloy, BaF2/Al, Cu, Fe, Co, Ni, Mn, Pd, Pt, and ITO. The cathode material may be deposited by any suitable technologies, such as a suitable physical vapor deposition method which includes a radio frequency magnetron sputtering, a vacuum thermal evaporation, an electron beam (e-beam), and the like.

The OLED may further include other functional layers such as a hole injection layer (HIL) or a hole transporting layer (HTL) 103, an electron blocking layer (EBL), an electron injection layer (EIL) or an electron transporting layer (ETL) (105), a hole blocking layer (HBL). Materials suitable for use in these functional layers are described in detail in WO2010135519A1, US20090134784A1 and WO2011110277A1, the entire contents of which three patent documents are incorporated herein by reference.

In an embodiment, in the foregoing light-emitting device, the hole injection layer (HIL) or the hole transporting layer (HTL) 103 is prepared from the foregoing formulation by printing.

In an embodiment, in the foregoing light-emitting device, the light-emitting layer 104 is prepared from the formulation according to the present disclosure by printing.

In an embodiment, in the foregoing light-emitting device, the hole transporting layer (HTL) 103 includes the polymer according to the present disclosure, and the light-emitting layer 104 includes a small molecular host material and a small molecular light-emitting material. The small molecular light-emitting material may be selected from a fluorescent light-emitting material and a phosphorescent light-emitting material.

In another embodiment, in the light-emitting device according to the present disclosure, the hole transporting layer (HTL) 103 includes the foregoing conjugated polymer, and the light-emitting layer 104 includes a high molecular light-emitting material.

The electroluminescence device according to the present disclosure has a light emission wavelength between 300 and 1000 nm, further between 350 and 900 nm, and still further between 400 and 800 nm.

The present disclosure further provides use of the organic electronic device according to the present disclosure in a variety of electronic equipment including, but not limited to, display equipment, lighting equipment, light sources, sensors, and the like.

The present disclosure further relates to organic electronic equipment including the organic electronic device according to the present disclosure, including, but not limited to, display equipment, lighting equipment, a light source, a sensor, and the like.

The disclosure will now be described with reference to the preferred embodiments, but the disclosure is not to be construed as being limited to the following examples. It should be understood that the appended claims are intended to cover the scope of the disclosure. Those skilled in the art will understand that modifications can be made to various embodiments of the disclosure with the teaching of the present disclosure, which will be covered by the spirit and scope of the claims of the disclosure.

Examples

The preparation method of the series of polymers and the preparation method of the corresponding OLED devices will be described below by taking five polymers as examples.

Synthesis of Monomer 1:

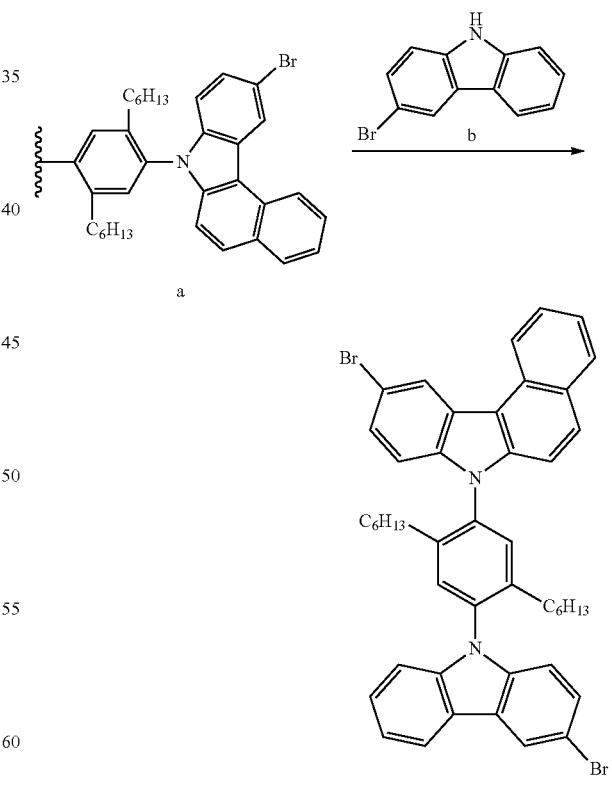

Monomer 1

Compound a (12.00 g, 18 mmol), compound b (4.43 g, 18 mmol), CuI (0.34 g, 1.8 mmol), $K_2CO_3$ (7.45 g, 54 mmol) were dissolved in anhydrous DMF (100 ml), and reacted at 160° C. for 24 hours; after the reaction, the reaction solution was poured into water while it was hot, and the solid was collected and separated by silica gel column with PE:DCM=5:1. White solid (8.5 g) was obtained with a yield rate of 61%.

Synthesis of Monomer 2:

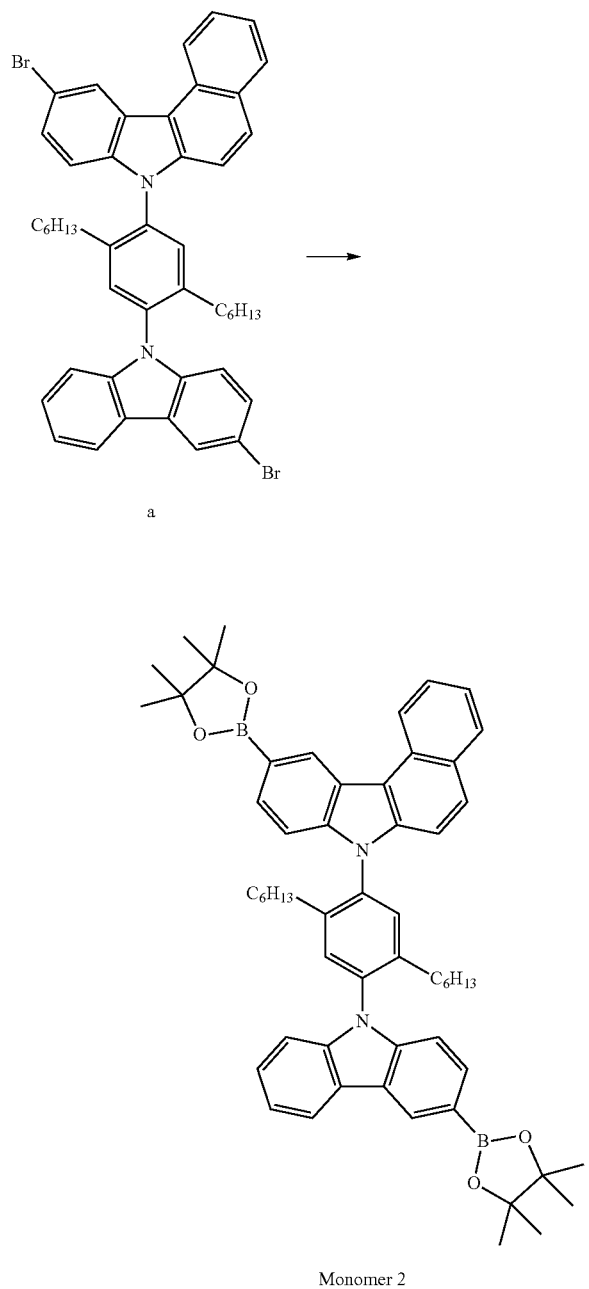

Monomer 2

Compound a (1.77 g, 2.26 mmol), diboronic acid pinacol ester (1.72 g, 6.78 mmol), Pd(dppf)Cl$_2$ (0.05 g, 0.0678 mmol), KOAc (1.33 g, 13.56 mmol) were dissolved in dioxane (50 ml) and reacted at 100° C. for 24 hours. After the reaction, the reaction solution was poured into water, and the solid was collected. After drying, the solid was separated by column with PE:DCM=1:1. White solid (1.57 g) was obtained with a yield rate of 79%.

Synthesis of Monomer 3:

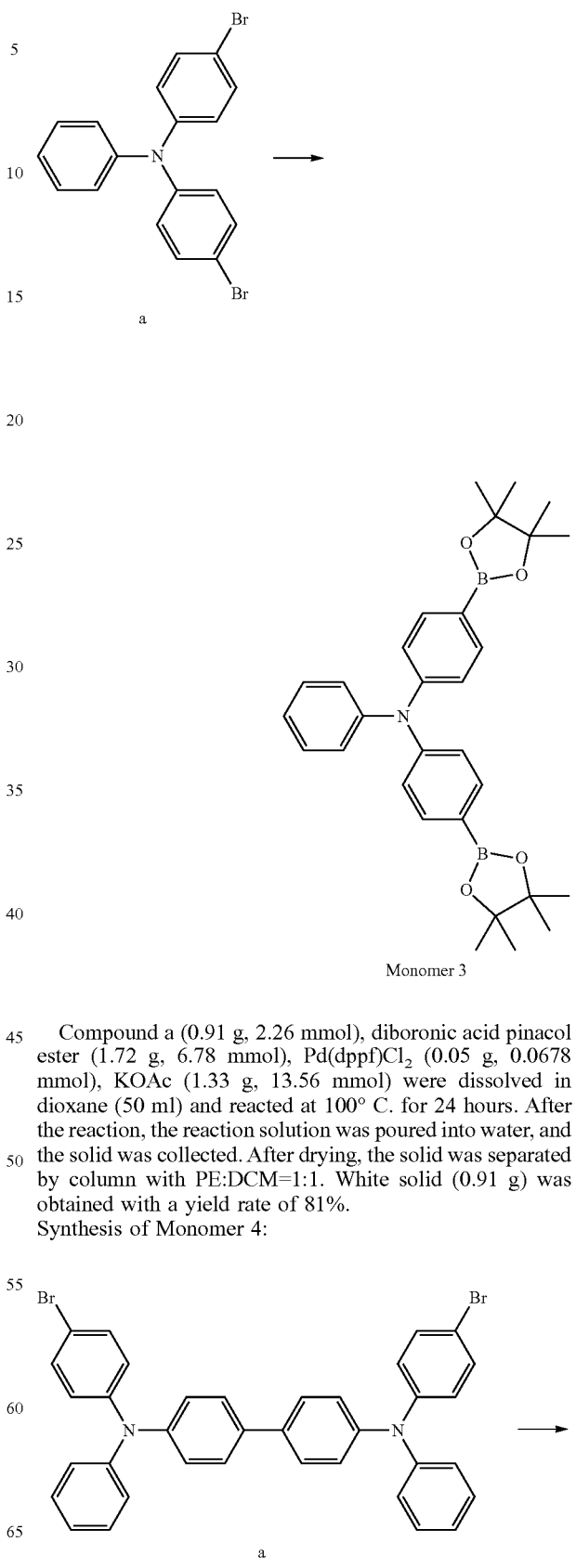

Monomer 3

Compound a (0.91 g, 2.26 mmol), diboronic acid pinacol ester (1.72 g, 6.78 mmol), Pd(dppf)Cl$_2$ (0.05 g, 0.0678 mmol), KOAc (1.33 g, 13.56 mmol) were dissolved in dioxane (50 ml) and reacted at 100° C. for 24 hours. After the reaction, the reaction solution was poured into water, and the solid was collected. After drying, the solid was separated by column with PE:DCM=1:1. White solid (0.91 g) was obtained with a yield rate of 81%.

Synthesis of Monomer 4:

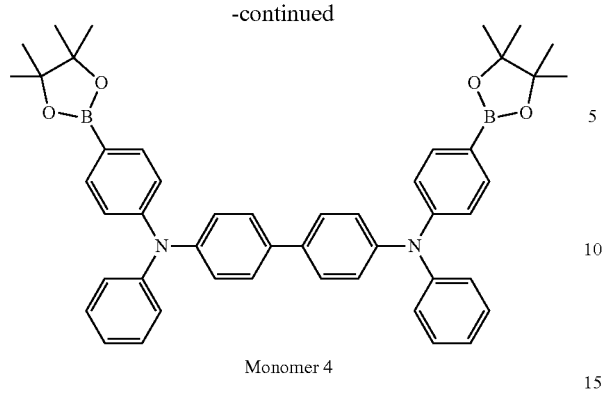

Monomer 4

Compound a (1.46 g, 2.26 mmol), diboronic acid pinacol ester (1.72 g, 6.78 mmol), Pd(dppf)Cl$_2$ (0.05 g, 0.0678 mmol), KOAc (1.33 g, 13.56 mmol) were dissolved in dioxane (50 ml) and reacted at 100° C. for 24 hours. After the reaction, the reaction solution was poured into water, and the solid was collected. After drying, the solid was separated by column with PE:DCM=1:1. Pale yellow solid (1.34 g) was obtained with a yield rate of 80%.

Synthesis of Monomer 5:

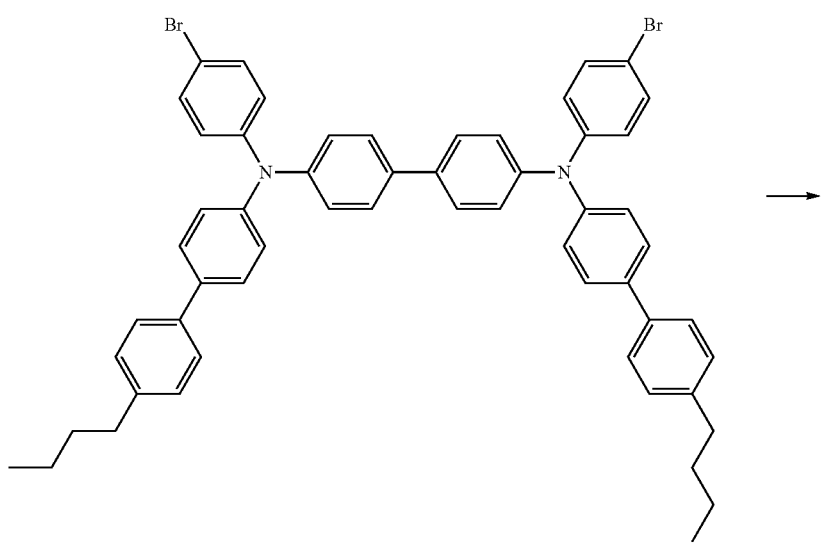

a

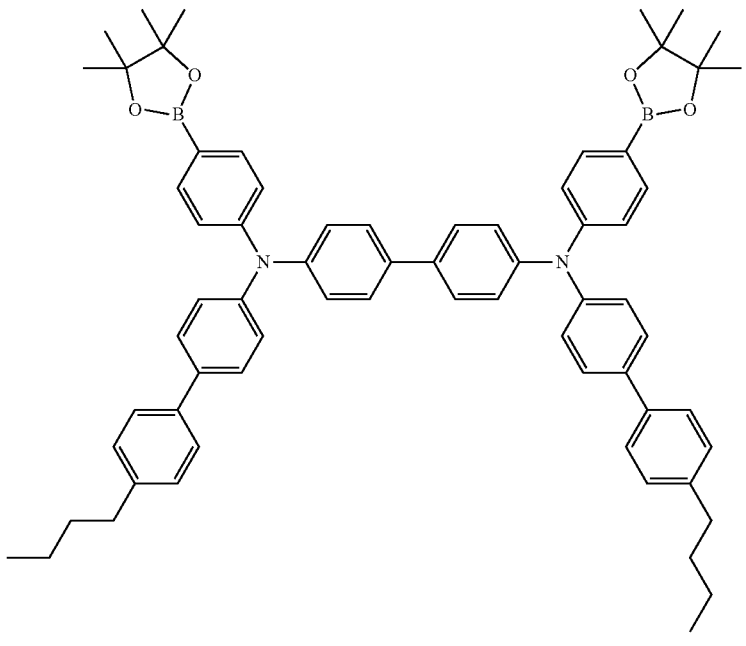

Monomer 5

Compound a (2.06 g, 2.26 mmol), diboronic acid pinacol ester (1.72 g, 6.78 mmol), Pd(dppf)Cl$_2$ (0.05 g, 0.0678 mmol), KOAc (1.33 g, 13.56 mmol) were dissolved in dioxane (50 ml) and reacted at 100° C. for 24 hours. After the reaction, the reaction solution was poured into water, and the solid was collected. After drying, the solid was separated by column with PE:DCM=1:1. Pale yellow solid (1.70 g) was obtained with a yield rate of 75%.

Synthesis of Monomer 6:

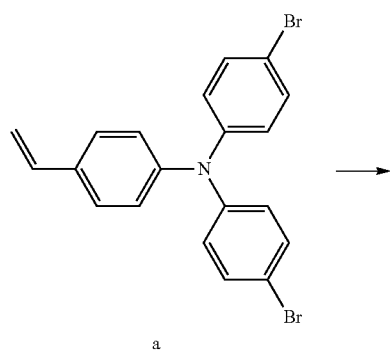

a

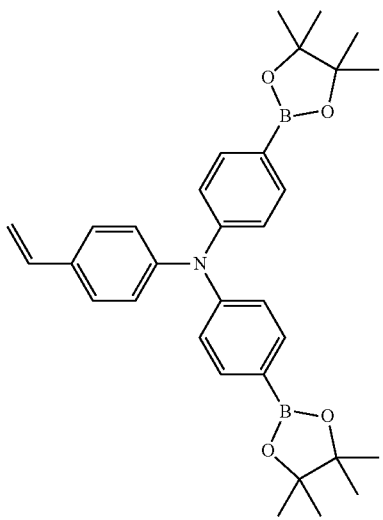

Monomer 6

Compound a (1.04 g, 2.26 mmol), diboronic acid pinacol ester (1.72 g, 6.78 mmol), Pd(dppf)Cl$_2$ (0.05 g, 0.0678 mmol), KOAc (1.33 g, 13.56 mmol) were dissolved in dioxane (50 ml) and reacted at 100° C. for 24 hours. After the reaction, the reaction solution was poured into water, and the solid was collected. After drying, the solid was separated by column with PE:DCM=1:1. White solid (0.91 g) was obtained with a yield rate of 79%.

Synthesis of Monomer 7:

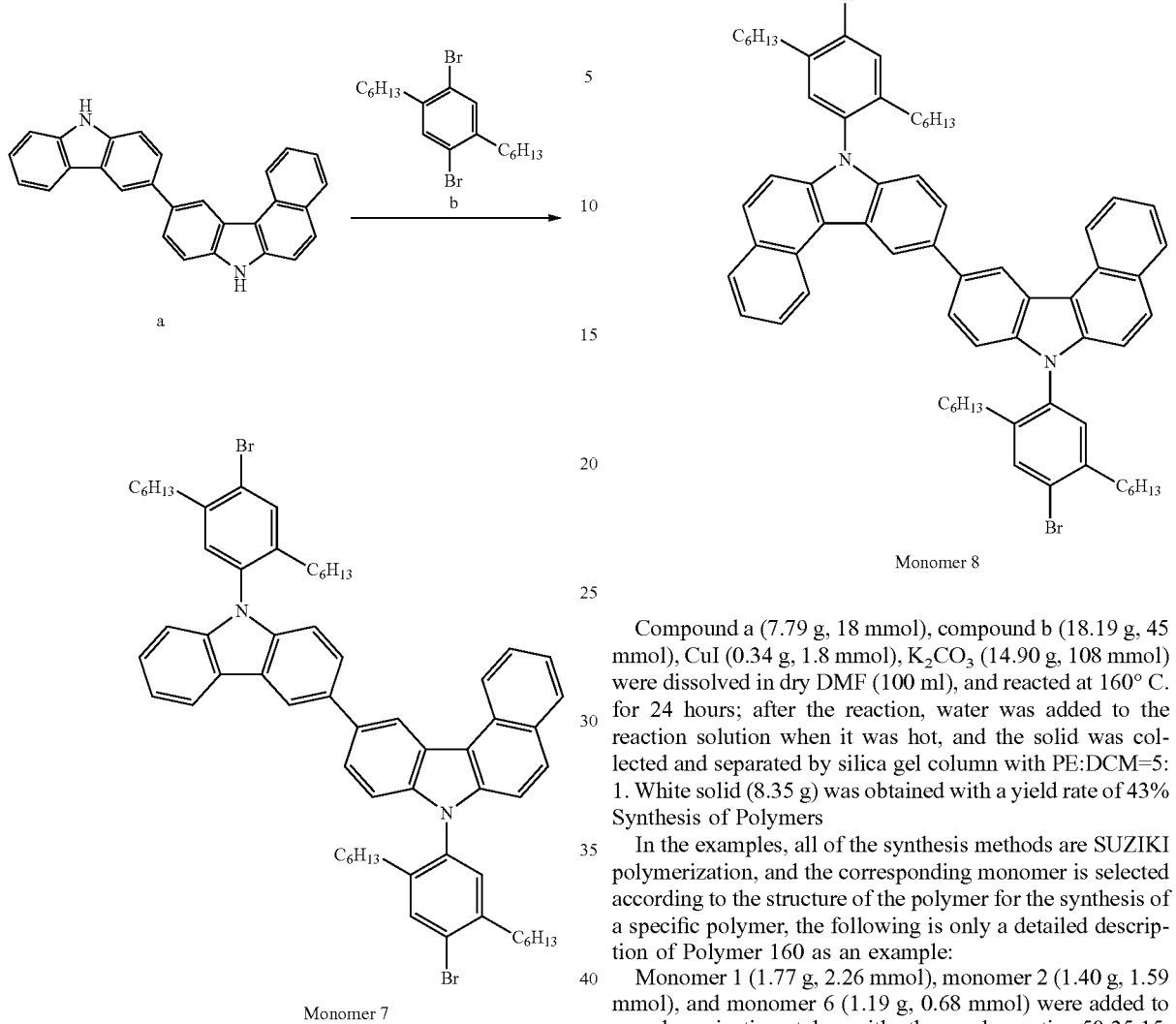

Monomer 7

Compound a (6.88 g, 18 mmol), compound b (18.19 g, 45 mmol), CuI (0.34 g, 1.8 mmol), K$_2$CO$_3$ (14.90 g, 108 mmol) were dissolved in dry DMF (100 ml), and reacted at 160° C. for 24 hours; after the reaction, water was added to the reaction solution when it was hot, and the solid was collected and separated by silica gel column with PE:DCM=5:1. White solid (10.56 g) was obtained with a yield rate of 54%

Synthesis of Monomer 8:

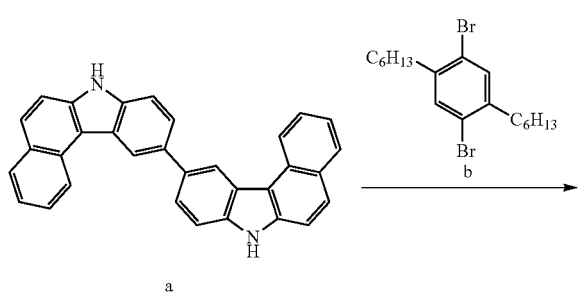

Monomer 8

Compound a (7.79 g, 18 mmol), compound b (18.19 g, 45 mmol), CuI (0.34 g, 1.8 mmol), K$_2$CO$_3$ (14.90 g, 108 mmol) were dissolved in dry DMF (100 ml), and reacted at 160° C. for 24 hours; after the reaction, water was added to the reaction solution when it was hot, and the solid was collected and separated by silica gel column with PE:DCM=5:1. White solid (8.35 g) was obtained with a yield rate of 43%

Synthesis of Polymers

In the examples, all of the synthesis methods are SUZIKI polymerization, and the corresponding monomer is selected according to the structure of the polymer for the synthesis of a specific polymer, the following is only a detailed description of Polymer 160 as an example:

Monomer 1 (1.77 g, 2.26 mmol), monomer 2 (1.40 g, 1.59 mmol), and monomer 6 (1.19 g, 0.68 mmol) were added to a polymerization tube with the molar ratio 50:35:15, Pd(dba)2 (0.026 g, 0.045 mmol), Sphos (0.037 g, 0.090 mmol), potassium carbonate aqueous solution (3.39 ml, 2 M) and toluene (5 ml) were simultaneously added. After a full gas exchange, nitrogen protection was applied. The reaction was carried out in dark at 100° C. for 24 hours. Thereafter, bromobenzene (0.1 ml) was added, and the reaction was carried out for 6 hours, and then phenylboronic acid (0.2 g) was added, followed by reaction for 6 hours. The reaction solution was cooled and washed with deionized water for 3 times. The organic phase was dried and quickly subjected to short silica gel column with PE:DCM=2:1 polarity. The polymer was dissolved in DCM (50 ml) and slowly poured into methanol (200 ml) to form silk. The polymer was extracted with acetone for 24 h and the silk formation-extraction process was repeated for 3 times. Polymer P1 was obtained (1.73 g, a yield rate of 67%, Mw=139376, PDI=1.89).

Example 1: Synthesis of Polymer P1 as described previously;

Example 2: Synthesis of Polymer P2: except that the polymeric monomers were monomer 7, monomer 3, and monomer 6, the other conditions were the same as that of Example 1, and Mw of Polymer 156 is 14476, PDI=1.91.

Example 3: Synthesis of Polymer P3: except that the polymeric monomers were monomer 7, monomer 4, and monomer 6, the other conditions were the same as that of Example 1, and Mw of Polymer 157 is 136305, PDI=2.31

Example 4: Synthesis of Polymer P4: except that the polymeric monomers were monomer 7, monomer 5, and monomer 6, the other conditions were the same as that of Example 1, and Mw of Polymer 158 is 122470, PDI=2.25.

Example 5: Synthesis of Polymer P5: except that the polymeric monomers were monomer 8, monomer 3, and monomer 6, the other conditions were the same as that of Example 1, and Mw of Polymer 159 is 147485, PDI=2.79.

Example 6: Preparation of OLED devices

Other materials are as follows:

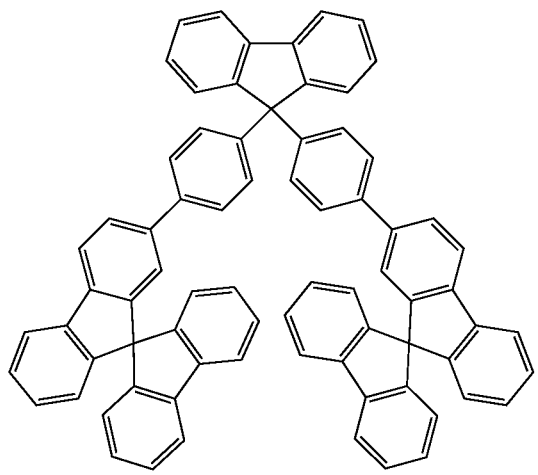

H1

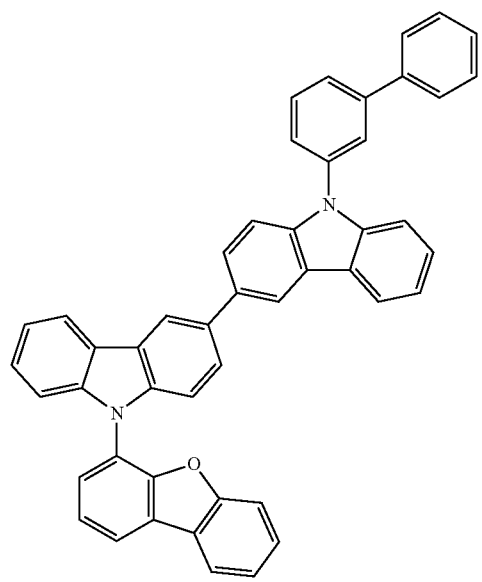

H2

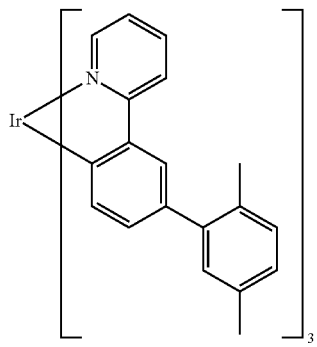

E1 wherein H1 is a co-host material and synthesis of which is referred to the Chinese Patent NO. CN201510889328.8; H2 is a co-host material and synthesis of which is referred to the Patent NO. WO201034125A1; E1 is a phosphorescent guest, and synthesis of which is referred to the Patent NO. CN102668152;

The preparation steps of the OLED device (OLED-Ref) were as follows:

1) Cleaning of an ITO transparent electrode (anode) glass substrate: the substrate was subjected to ultrasonic treatment with an aqueous solution of 5% Decon90 cleaning solution for 30 minutes, followed by ultrasonic cleaning with deionized water for several times, then subjected to ultrasonic cleaning with isopropanol and nitrogen drying. The substrate was treated under oxygen plasma for 5 minutes to clean the ITO surface and to improve the work function of the ITO electrode.

2) Preparation of an HIL and an HTL: PEDOT:PSS (Clevios™ PEDOT:PSS A14083) was spin-coated on the oxygen plasma-treated glass substrate to obtain an 80-nm thin film, the film was annealed in air at 150° C. for 20 minutes, and a 20-nm Poly-TFB thin film (CAS: 223569-31-1, purchased from Lumtec. Corp; 5 mg/mL toluene solution) was spin-coated on the PEDOT:PSS layer, followed by treatment on a hot plate at 180° C. for 60 minutes.

3) Preparation of a light-emitting layer: H1, H2, E1 were dissolved in toluene at a weight ratio of 40:40:20, and the concentration of the solution is 20 mg/mL. This solution was spin-coated in a nitrogen glove box to obtain a 60-nm thin film and was then annealed at 120° C. for 10 minutes.

4) Preparation of a cathode: the spin-coated device was placed in a vacuum evaporation chamber, and 2-nm barium and 100-nm aluminum were sequentially deposited to yield a light-emitting device.

5) The device was encapsulated in a nitrogen glove box using an ultraviolet curing resin and a glass cover.

The preparation steps of the OLED devices (OLED-1 to OLED-4) were the same as above, but when the HTL layer was prepared, P1 to P4 were respectively used instead of Poly-TFB.

Current-voltage (I-V) property, luminous intensity and external quantum efficiency of the OLED devices were measured by a Keithley 236 current and voltage-measurement system and a calibrated silicon photodiode.

| | Efficiency (cd/A) @1000 nits related to OLED-Ref |
|---|---|
| OLED-Ref | 1 |
| OLED-1 | 1.75 |
| OLED-2 | 1.43 |
| OLED-3 | 2.41 |
| OLED-4 | 3.12 |
| OLED-5 | 2.74 |

When the polymer according to the present disclosure is used in the HTL, the performance, especially the efficiency has been greatly improved compared to that of the conventional Poly-TFB device. This may be due to the polymer according to the present disclosure has a higher triplet excited state energy level and thereby has a better blocking effect on the triplet state.

It should be understood that the application of the disclosure is not limited to the above-described examples and that those skilled in the art would understand that it may be modified or changed in accordance with the above description, all of which are within the scope of the claims appended hereto.

What is claimed is:

1. A conjugated polymer comprising a repeating unit represented by a general formula (IV):

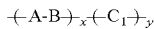  (IV)

wherein x, y are molar percentages of the repeating units of the general formula (IV), x>0, y>0, and x+y=1;

$C_1$ is selected from the following formulas:

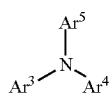 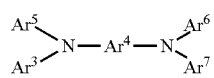

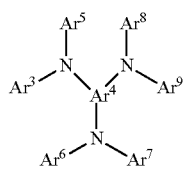 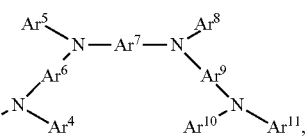

or 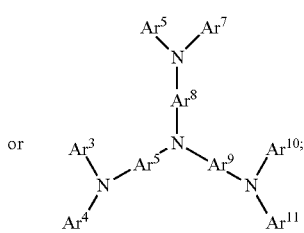

$-(A-B)_x$ is represented by the following formula (I-9) or (I-10):

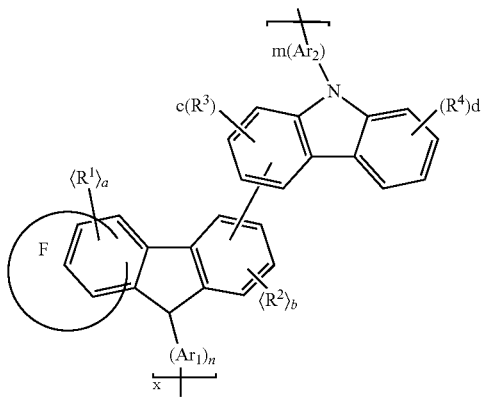 (I-9)

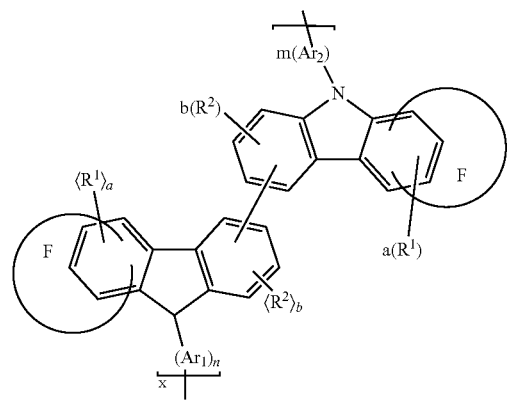 (I-10)

wherein ring F is an aromatic ring system containing 5 to 20 ring atoms or a heteroaromatic ring system containing 5 to 20 ring atoms and is fused with phenyl;

$Ar_1$, $Ar_2$ are each independently an aromatic ring system containing 5 to 40 ring atoms or a heteroaromatic ring system containing 5 to 40 ring atoms;

each of $Ar^3$ to $Ar^{11}$ is independently selected from the group consisting of benzene, biphenyl, triphenyl, benzo, naphthalene, anthracene, phenalene, phenanthrene, fluorene, pyrene, chrysene, perylene, azulene, dibenzothiophene, dibenzofuran, benzofuran, benzothiophene, carbazole, pyrazole, imidazole, triazole, isoxazole, thiazole, oxadiazole, oxytriazole, dioxazole, thiadiazole, pyridine, pyridazine, pyrimidine, pyrazine, triazine, oxazine, oxathiazine, oxadiazine, indole, benzimidazole, indazole, indolizine, benzoxazole, benzisoxazole, benzothiazole, quinoline, isoquinoline, cinnoline, quinazoline, quinoxaline, naphthalene, phthalein, pteridine, xanthene, acridine, phenazine, phenothiazine, phenoxazine, dibenzoselenophene, benzoselenophene, benzofurapyridine, indolocarbazole, pyridine indole, dipyridinipyrrole, dipyridine furan, benzothienopyridine, thiophene pyridine, benzoselenophen pyridine, and dipyridyl selenophene;

$R^1$, $R^2$, $R^3$, and $R^4$ are each independently selected from the group consisting of hydrogen, deuterium, fluorine, cyanide, an alkyl chain, a fluoroalkyl chain, an aromatic ring, a heteroaromatic ring, an amino group, a silicon group, and a methyl germanium group;

the adjacent $R^1$, $R^2$, $R^3$, $R^4$ may form a monocyclic or polycyclic aliphatic or aromatic ring system with each other or with a ring bonded to the groups;

a is 0, 1, 2, 3, 4, 5, 6, 7, 8, 9 or 10;
b, c, and d are each independently 0, 1, 2, 3 or 4;
m and n are each independently 0 or 1,
wherein the conjugated polymer has a molecular weight greater than or equal to 100 kg/mol.
2. The conjugated polymer according to claim 1, wherein A is selected from the group consisting of the following structures:
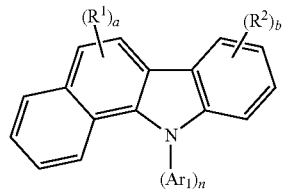
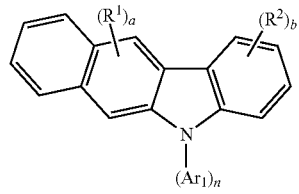
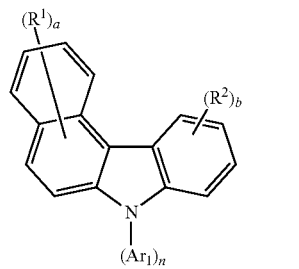
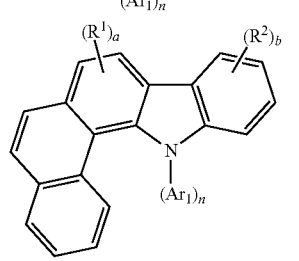
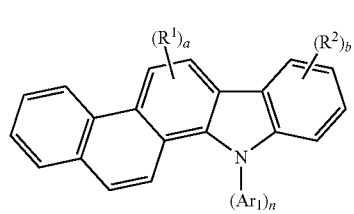
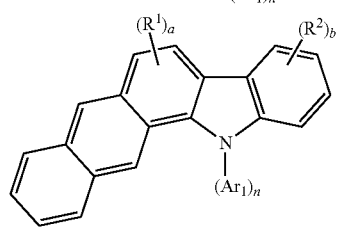
-continued
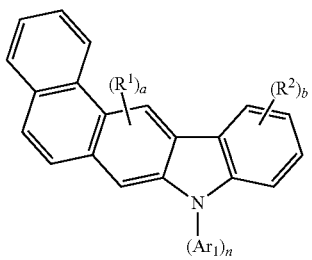
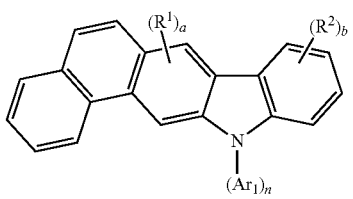
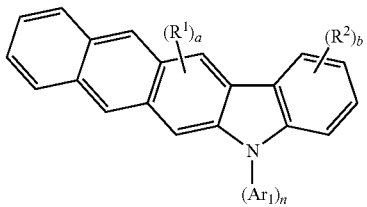

-continued

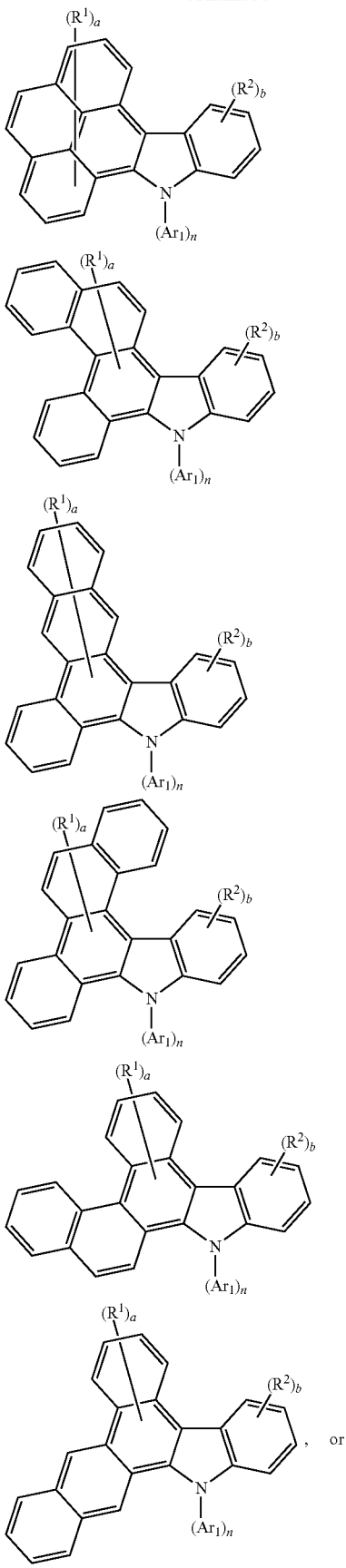

, or

-continued

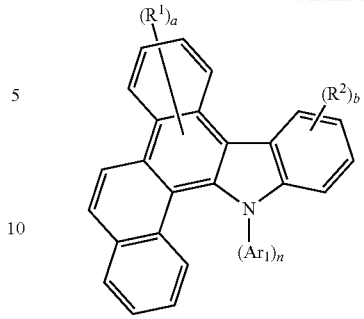

wherein a, b, $R^1$, $R^2$, $Ar^1$, and n are defined as in claim 1.

3. The conjugated polymer according to claim 1, wherein the conjugated polymer contains at least one deuterium atom.

4. A mixture comprising a conjugated polymer according to claim 1, and an organic solvent or an organic functional material selected from the group consisting of a hole injection or transporting material, a hole blocking material, an electron injection or transporting material, an electron blocking material, an organic matrix material, a singlet emitter, a triplet emitter, a thermally activated delayed fluorescent material, and an organic dye.

5. The conjugated polymer according to claim 1, ring F is one selected from the following structural groups:

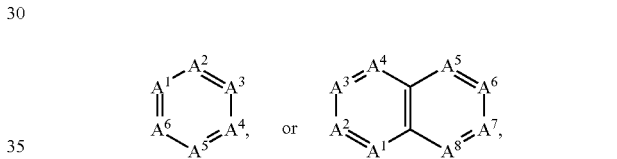

wherein
$A^1$, $A^2$, $A^3$, $A^4$, $A^5$, $A^6$, $A^7$, $A^8$ independently represent $CR^5$ or N;
$R^5$ is selected from H, D, or a linear alkyl group containing 1 to 20 C atoms, or an alkoxy group containing 1 to 20 C atoms, or a thioalkoxy group containing 1 to 20 C atoms, or a branched or a cyclic alkyl group containing 3 to 20 C atoms, or a silyl group, or a substituted keto group containing 1 to 20 C atoms, or an alkoxycarbonyl group containing 2 to 20 C atoms, or an aryloxycarbonyl group containing 7 to 20 C atom, a cyano group, a carbamoyl group, a haloformyl group, a formyl group, an isocyano group, an isocyanate group, a thiocyanate group, an isothiocyanate group, a hydroxyl group, a nitryl group, a $CF_3$ group, Cl, Br, F, a crosslinkable group, or a substituted or unsubstituted aromatic ring system containing 5 to 20 ring atoms or a substituted or unsubstituted heteroaromatic ring system containing 5 to 20 ring atoms, or an aryloxy group containing 5 to 40 ring atoms or a heteroaryloxy group containing 5 to 40 ring atoms.

6. The conjugated polymer according to claim 1, wherein ring F is

.

7. The conjugated polymer according to claim 1, wherein at least one of n and m is 1.
8. The conjugated polymer according to claim 1, wherein $C_1$ is
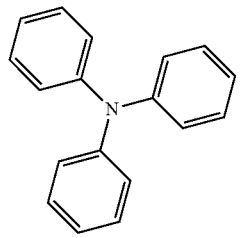 [SMILES: c1ccc(N(c2ccccc2)c2ccccc2)cc1]
* * * * *